US008188063B2

(12) United States Patent
Li et al.

(10) Patent No.: US 8,188,063 B2
(45) Date of Patent: May 29, 2012

(54) USE OF ADENOSINE $A_{2A}$ MODULATORS TO TREAT SPINAL CORD INJURY

(75) Inventors: Yuesheng Jason Li, Charlottesville, VA (US); Joel M. Linden, Charlottesville, VA (US); Jayson M. Rieger, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1028 days.

(21) Appl. No.: 11/765,320

(22) Filed: Jun. 19, 2007

(65) Prior Publication Data

US 2008/0064653 A1    Mar. 13, 2008

Related U.S. Application Data

(60) Provisional application No. 60/814,713, filed on Jun. 19, 2006.

(51) Int. Cl.
*A01N 43/04* (2006.01)
*A61K 31/70* (2006.01)

(52) U.S. Cl. .......................................... 514/46; 514/42
(58) Field of Classification Search .................. None
See application file for complete search history.

(56) References Cited

U.S. PATENT DOCUMENTS

| | | | |
|---|---|---|---|
| 3,892,777 A | 7/1975 | Gruenman et al. |
| 4,012,495 A | 3/1977 | Schmeichen et al. |
| 4,193,926 A | 3/1980 | Schmiechen et al. |
| 4,242,345 A | 12/1980 | Brenner et al. |
| 4,448,721 A | 5/1984 | DeLuca et al. |
| 4,559,157 A | 12/1985 | Smith et al. |
| 4,608,392 A | 8/1986 | Jacquet et al. |
| 4,665,074 A | 5/1987 | Amschler |
| 4,695,660 A | 9/1987 | Otte et al. |
| 4,820,508 A | 4/1989 | Wortzman |
| 4,824,660 A | 4/1989 | Angello et al. |
| 4,879,296 A | 11/1989 | Daluge et al. |
| 4,938,949 A | 7/1990 | Borch et al. |
| 4,956,345 A | 9/1990 | Miyasaka et al. |
| 4,965,271 A | 10/1990 | Mandell et al. |
| 4,968,697 A | 11/1990 | Hutchison |
| 4,992,478 A | 2/1991 | Geria |
| 5,070,877 A | 12/1991 | Mohiuddin et al. |
| 5,096,906 A | 3/1992 | Mandell et al. |
| 5,124,455 A | 6/1992 | Lombardo et al. |
| 5,140,015 A | 8/1992 | Olsson et al. |
| 5,189,027 A | 2/1993 | Miyashita et al. |
| 5,272,153 A | 12/1993 | Mandell et al. |
| 5,278,150 A | 1/1994 | Olsson et al. |
| 5,298,508 A | 3/1994 | Jacobson et al. |
| 5,364,862 A | 11/1994 | Spada et al. |
| 5,561,111 A | 10/1996 | Guerrant et al. |
| 5,561,134 A | 10/1996 | Spada et al. |
| 5,565,462 A | 10/1996 | Eitan et al. |
| 5,593,973 A | 1/1997 | Carter |
| 5,593,975 A | 1/1997 | Cristalli |
| 5,593,976 A | 1/1997 | Mongelli et al. |
| 5,665,754 A | 9/1997 | Feldman et al. |
| 5,668,139 A | 9/1997 | Belardinelli et al. |
| 5,696,254 A | 12/1997 | Mansour et al. |
| 5,731,296 A | 3/1998 | Sollevi |
| 5,756,706 A | 5/1998 | Mansour et al. |
| 5,776,940 A | 7/1998 | Daluge et al. |
| 5,854,081 A | 12/1998 | Linden et al. |
| 5,877,180 A | 3/1999 | Linden et al. |
| 5,877,190 A | 3/1999 | Dhainaut et al. |
| 5,932,558 A | 8/1999 | Cronstein et al. |
| 5,998,386 A | 12/1999 | Feldman |
| 6,004,945 A | 12/1999 | Fukunaga |
| RE36,494 E | 1/2000 | Olsson et al. |
| 6,020,321 A | 2/2000 | Cronstein et al. |
| 6,020,339 A | 2/2000 | Perrier et al. |
| 6,034,089 A | 3/2000 | Han et al. |
| 6,060,481 A | 5/2000 | LaNoue et al. |
| 6,117,878 A | 9/2000 | Linden et al. |
| 6,232,297 B1 | 5/2001 | Linden et al. |
| 6,303,619 B1 | 10/2001 | Linden et al. |
| 6,322,771 B1 | 11/2001 | Linden et al. |
| 6,326,359 B1 | 12/2001 | Monaghan et al. |
| 6,332,771 B1 | 12/2001 | Adams et al. |
| 6,339,072 B2 | 1/2002 | Martin et al. |
| 6,350,735 B1 | 2/2002 | Monaghan |
| 6,387,889 B1 | 5/2002 | Endo et al. |
| 6,407,076 B1 | 6/2002 | Box et al. |
| 6,448,235 B1 | 9/2002 | Linden et al. |
| 6,455,510 B1 | 9/2002 | Charles et al. |
| 6,514,949 B1 | 2/2003 | Linden et al. |
| 6,525,032 B2 | 2/2003 | Mantrell et al. |
| 6,531,457 B2 | 3/2003 | Linden et al. |
| 6,545,002 B1 | 4/2003 | Linden et al. |
| 6,624,158 B2 | 9/2003 | Mantell et al. |
| 6,670,334 B2 | 12/2003 | Linden |
| 6,936,596 B2 | 8/2005 | Konno et al. |
| 7,160,890 B2 | 1/2007 | Castelhano et al. |
| 7,214,665 B2 | 5/2007 | Linden et al. |
| 7,217,702 B2 | 5/2007 | Beauglehole et al. |
| 7,226,913 B2 | 6/2007 | Linden et al. |
| 7,307,079 B2 | 12/2007 | Den Hartog et al. |
| 7,378,400 B2 | 5/2008 | Rieger et al. |
| 7,396,825 B2 | 7/2008 | Okusa et al. |
| 7,427,606 B2 | 9/2008 | Linden et al. |
| 7,442,687 B2 | 10/2008 | Rieger et al. |
| 7,553,823 B2 | 6/2009 | Zablocki et al. |
| 7,576,069 B2 | 8/2009 | Rieger et al. |
| 7,589,076 B2 | 9/2009 | Rieger et al. |
| 7,605,143 B2 * | 10/2009 | Rieger et al. ..................... 514/46 |
| 7,737,127 B2 | 6/2010 | Linden et al. |
| 7,875,595 B2 | 1/2011 | Rieger et al. |
| 7,888,329 B2 | 2/2011 | Rieger et al. |
| 7,989,431 B2 | 8/2011 | Rieger et al. |

(Continued)

FOREIGN PATENT DOCUMENTS

BR          0007864 A      6/2001

(Continued)

OTHER PUBLICATIONS

Cassada et al. (Ann Thorac Surg., 2002; 74:846-50).*

(Continued)

*Primary Examiner* — Traviss C McIntosh, III
(74) *Attorney, Agent, or Firm* — Schwegman, Lundberg & Woessner, P.A.

(57) ABSTRACT

The present invention is a method for treatment or prevention of injury to nerve cells. The method can use at least one $A_{2A}$ receptor modulator to prevent injury to or enhance the healing of the injured cells.

21 Claims, 15 Drawing Sheets

U.S. PATENT DOCUMENTS

| | | | |
|---|---|---|---|
| 2001/0027185 A1 | 10/2001 | Linden et al. |
| 2002/0032168 A1 | 3/2002 | Mantrell et al. |
| 2002/0058641 A1 | 5/2002 | Mantell et al. |
| 2002/0072597 A1 | 6/2002 | Mantell et al. |
| 2002/0111327 A1 | 8/2002 | Linden et al. |
| 2003/0013675 A1 | 1/2003 | Yeadon et al. |
| 2003/0162742 A1 | 8/2003 | Linden et al. |
| 2003/0186925 A1 | 10/2003 | Palmer et al. |
| 2003/0186926 A1 | 10/2003 | Linden et al. |
| 2004/0229246 A1 | 11/2004 | Fishman et al. |
| 2005/0004221 A1 | 1/2005 | Hildebrand et al. |
| 2005/0020532 A1 | 1/2005 | Elzein et al. |
| 2005/0065341 A1 | 3/2005 | Wang et al. |
| 2005/0182018 A1 | 8/2005 | Linden et al. |
| 2005/0261236 A1 | 11/2005 | Okusa et al. |
| 2005/0282831 A1 | 12/2005 | Beauglehole et al. |
| 2006/0030889 A1 | 2/2006 | Ben-Haim et al. |
| 2006/0040888 A1 | 2/2006 | Rieger et al. |
| 2006/0040889 A1 | 2/2006 | Rieger et al. |
| 2006/0052298 A1 | 3/2006 | Guerrant et al. |
| 2006/0100169 A1 | 5/2006 | Rieger et al. |
| 2006/0128652 A1 | 6/2006 | Jagtap et al. |
| 2006/0128708 A1 | 6/2006 | Diamond et al. |
| 2006/0217343 A1 | 9/2006 | Rieger et al. |
| 2007/0027073 A1 | 2/2007 | Rubinstein et al. |
| 2007/0032450 A1 | 2/2007 | Rieger |
| 2007/0072843 A1 | 3/2007 | Wang et al. |
| 2007/0232559 A1 | 10/2007 | Linden et al. |
| 2007/0265440 A1 | 11/2007 | Linden et al. |
| 2008/0009460 A1 | 1/2008 | Linden et al. |
| 2008/0027022 A1 | 1/2008 | Linden et al. |
| 2008/0214581 A1 | 9/2008 | Allen et al. |
| 2008/0262001 A1 | 10/2008 | Kranenburg et al. |
| 2008/0312160 A1 | 12/2008 | Guerrant et al. |
| 2009/0012035 A1 | 1/2009 | Jacobson et al. |
| 2009/0081764 A1 | 3/2009 | Pausch et al. |
| 2009/0118309 A1 | 5/2009 | Beauglehole et al. |
| 2009/0123510 A1 | 5/2009 | Cronstein et al. |
| 2009/0162282 A1 | 6/2009 | Thompson et al. |
| 2009/0162292 A1 | 6/2009 | Thompson et al. |
| 2009/0170803 A1 | 7/2009 | Linden et al. |
| 2009/0181920 A1 | 7/2009 | Watkins et al. |
| 2009/0253647 A1 | 10/2009 | Rieger et al. |
| 2009/0280059 A1 | 11/2009 | Rieger et al. |
| 2009/0298788 A1 | 12/2009 | Rieger et al. |
| 2009/0325967 A1 | 12/2009 | Fairhurst et al. |
| 2010/0152127 A1 | 6/2010 | Linden et al. |
| 2010/0166698 A1 | 7/2010 | Rieger |
| 2011/0136755 A1 | 6/2011 | Rieger et al. |

FOREIGN PATENT DOCUMENTS

| | | |
|---|---|---|
| EP | 0488331 A1 | 6/1992 |
| EP | 0488336 A1 | 6/1992 |
| EP | 0488336 B1 | 5/1995 |
| EP | 0700908 A1 | 3/1996 |
| EP | 1110554 A1 | 6/2001 |
| EP | 1150991 B1 | 11/2001 |
| EP | 1194440 A2 | 4/2002 |
| EP | 1194440 B1 | 2/2005 |
| IL | 144188 A | 5/2002 |
| JP | 6299330 A | 5/1987 |
| JP | 06299335 A | 5/1987 |
| JP | 03287537 A | 12/1991 |
| JP | 59197 A | 1/1993 |
| JP | 59198 A | 1/1993 |
| JP | 05025195 A | 2/1993 |
| JP | 05163294 A2 | 6/1993 |
| JP | 07-508718 | 9/1995 |
| JP | 11335302 A | 12/1999 |
| JP | 20007695 A | 1/2000 |
| JP | 2002536300 | 10/2002 |
| NZ | 530976 | 7/2005 |
| WO | WO-9005526 A1 | 5/1990 |
| WO | WO-9015812 A1 | 12/1990 |
| WO | WO-9109864 A1 | 7/1991 |
| WO | WO-93/22328 A1 | 11/1993 |
| WO | WO-96/02553 A2 | 2/1996 |
| WO | WO-96/04280 A1 | 2/1996 |
| WO | WO-98/47509 A1 | 10/1998 |
| WO | WO-9852611 A1 | 11/1998 |
| WO | WO-98/57651 A1 | 12/1998 |
| WO | WO-98/57661 A1 | 12/1998 |
| WO | WO-99/34804 A1 | 7/1999 |
| WO | WO-99/38877 A2 | 8/1999 |
| WO | WO-99/41267 A1 | 8/1999 |
| WO | WO-99/62518 A1 | 12/1999 |
| WO | WO-99/63938 A2 | 12/1999 |
| WO | WO-99/67263 A1 | 12/1999 |
| WO | WO-99/67264 A1 | 12/1999 |
| WO | WO-99/67265 A1 | 12/1999 |
| WO | WO-99/67266 A1 | 12/1999 |
| WO | WO-0012098 A1 | 3/2000 |
| WO | WO-00/23457 A1 | 4/2000 |
| WO | WO-00/44763 A2 | 8/2000 |
| WO | WO-0044763 A3 | 8/2000 |
| WO | WO-00/72799 A2 | 12/2000 |
| WO | WO-00/78774 A2 | 12/2000 |
| WO | WO-00/78777 A1 | 12/2000 |
| WO | WO-00/78779 A2 | 12/2000 |
| WO | WO-01/94368 A1 | 12/2001 |
| WO | WO-02/09701 A1 | 2/2002 |
| WO | WO-02/22630 A1 | 3/2002 |
| WO | WO-02/096462 A1 | 12/2002 |
| WO | WO-03/014137 A1 | 2/2003 |
| WO | WO-03/029264 A2 | 4/2003 |
| WO | WO-03029264 A2 | 4/2003 |
| WO | WO-03/086408 A1 | 10/2003 |
| WO | WO-03086408 A1 | 10/2003 |
| WO | WO-03/090733 A1 | 11/2003 |
| WO | WO-2005084653 A2 | 9/2005 |
| WO | WO-2005/097140 A2 | 10/2005 |
| WO | WO-2005/107463 A1 | 11/2005 |
| WO | WO-2006/015357 A2 | 2/2006 |
| WO | WO-2006/023272 A1 | 3/2006 |
| WO | WO-2006/028618 A1 | 3/2006 |
| WO | WO-2007/092936 A2 | 8/2007 |
| WO | WO-2007/092936 C2 | 8/2007 |
| WO | WO-2007/120972 A2 | 10/2007 |
| WO | WO-2008/124150 A1 | 10/2008 |

OTHER PUBLICATIONS

Li, Y., et al., "Mouse Spinal Cord Compression Injury is Reduced by Either Activation of the Adenosine $A_{2A}$ Receptor on Bone Marrow-Derived Cells or Deletion of the $A_{2A}$ Receptor on Non-Bone Marrow-Derived Cells", *Neuroscience*, 141, (2006), 2029-2039.

Vu, C. B., et al., "Piperazine Derivatives of [1,2,4] Triazolo [1,5-a][1,3,5]triazine as Potent and Selective Adenosine $A_{2A}$ Receptor Antagonists", *J. Med. Chem.*, 47, (2004), 4291-4299.

*The Merck Manual of Diagnosis and Therapy*, Beers, M.A., et al. (eds.), Merck and Company, (Jan. 1999), 924-925.

*Taber's Cyclopedic Medical Dictionary, 19th Edition*, Venes, et al. (eds.), F. A. Davis, Philadelphia, (2001), 960-961.

"STN Database Descriptions", *Chemical Abstracts Catalog*, (2006), p. 52.

Abiru, T., et al., "Nucleosides and nucleotides. 107. 2-(cycloalkylalkynyl)adenosines: adenosine $A_2$ receptor agonists with potent antihypertensive effects", *Journal of Medicinal Chemistry*, 35(12), (Jun. 12, 1992), 6747-6754.

Adah, S. A., "Synthesis of Complex Ethynyladenosines Using Organic Triflic Enolates in Palladium-Catalyzed Reactions: Potential Agonists for the Adenosine $A_2$ Receptor", *Tetrahedron*, 53(20), (1997), 6747-6754.

Ali, H., et al., "Methylxanthines Block Antigen-induced Responses in RBL-2H3 Cells Independently of Adenosine Receptors or Cyclic AMP: Evidence for Inhibition of Antigen Binding to IgE", *Journal of Pharmacology and Experimental Therapeutics*, 258, (1991), 954-962.

Andersson, P., et al., "Anti-anaphylactic and anti-inflammatory effects of xanthines in the lung", *Curr. Clin. Pract. Ser.*, (1985), 187-192.

Andrews, F. J., et al., "Effect of Nonsteroidal Anti-Inflammatory Drugs on LFA-1 and ICAM-1 Expression in Gastric Mucosa", *American Journal of Physiology—Gastrointestinal and Liver Physiology*, 266, (1994), G657-G664.

Appleyard, C. B., et al., "Tumor Necrosis Factor Mediation of NSAID-Induced Gastric Damage: Role of Leukocyte Adherence", *American Journal of Physiology—Gastrointestinal and Liver Physiology*, 33, (1996), G42-G48.

Auchampach, J. A., et al., "$A_3$ adenosine receptor agonist IB-MECA reduces myocardial ischemia-reperfusion injury in dogs", *Am J Physiol Heart Circ Physiol*, vol. 285, (2003), H607-H613.

Ballas, S. K., "Sickle Cell Anaemia: Progress in Pathogenesis and Treatment", *Drugs* vol. 62(8), (2002), 1143-1172.

Baraldi, P. G., et al., "Synthesis and Biological Activity of a New Series of $N^6$-Arylcarbamoyl, 2-(Ar)alkynyl-$N^6$-arylcarbamoyl, and $N^6$-Carboxamido derivatives of adenosine-5'-N-ethyluronamide as $A_1$ and $A_3$ Adenosine receptor agonists", *Journal of Medicinal Chemistry*, 41(17), (Aug. 13, 1998), 3174-3185.

Barold, S. S., et al., "Significance of Transient Electrocardiographic Q Waves in Coronary Artery Diseasse", *Cardiology Clinics*, 5(3), (Aug. 1987), 367-380.

Beck, P. L., et al., "Mechanisms of NSAID-Induced Gastrointestinal Injury Defined Using Mutant Mice", *Gastroenterology*, 119(3), (2000), 699-705.

Beers, M. H, et al., "The Merck Manual of Diagnosis and Therapy", *Merck Research Laboratories*, (1999), 245-256.

Belcher, J. D., et al., "Transgenic Sickle Mice Have Vascular Inflammation", *Blood*, 101(10), (2003), 3953-3959.

Berkich, D. A., et al., "Evidence of Regulated Coupling of $A_1$ Adenosine Receptors by Phosphorylation in Zucker Rats.", *American Journal of Physiology*, 268 (4), (Apr. 1995), E693-E704.

Bhattacharya, S., et al., "Effects of Long-term Treatment With the Allosteric Enhancer, PD81,723, on Chinese Hamster Ovary Cells Expressing Recombitant Human $A_1$ Adenosine Receptors", *Molecular Pharmacology*, 50(1), (Jul. 1996), 104-111.

Bhattacharya, S., et al., "The Allosteric Enhancer, PD 81,723, Stabilizes Human $A_1$ Adenosine Receptor Coupling to G Proteins", *Biochimica et Biophysica Acta*, 1265 (1), (Feb. 1995), 15-21.

Bradford, M. M., "A Rapid and Sensitive Method for the Quantitation of Microgram Quantities of Protein Utilizing the Principle of Protein-Dye Binding", *Analytical Biochemistry*, 72, (1976), 248-254.

Bridges, A. J., et al., "$N^6$-[2-(3,5-Dimethoxyphenyl)-2-(2-Methylphenyl)-Ethyl]Adenosine and Its Uronamide Derivatives. Novel Adenosine Agonists With Both High Affinity and High Selectivity for the Adenosine $A_2$ Receptor", *Journal of Medicinal Chemistry*, 31(7), (Jul. 1988), 1282-1285.

Brito, G. A. C., et al., "*Clostridium difficile* Toxin A Induces Intestinal Epithelial Cell Apoptosis and Damage: Role of Gln and Ala-Gln in Toxin A Effects", *Digestive Diseases and Sciences*, 50(7), (2005), 1271-1278.

Brodie, D. A., et al., "A Study of the Factors Involved in the Production of Gastric Ulcers by the Restraint Technique", *Gastroenterology*, 38(3), (1960), 353-360.

Bruns, R. F., "Adenosine Receptors—Roles and Pharmacology", *Biological Actions of Extracellular ATP*, 603, Annals of The New York Academy of Sciences, (1990), 211-226.

Bruns, R. F., et al., "Characterization of the $A_2$ Adenosine Receptor Labeled by [$^3$H]NECA in Rat Striatal Membranes", *Molecular Pharmacology*, 29, (1986), 331-346.

Buchanan, G. R., et al., "Sickle Cell Disease", *Hematology 2004*, 35-47.

Buster, B., et al., "The Effect of Adenosine Receptor Agonists on Neutrophil Pleocytosis and Blood-Brain Barrier Pathophysiology in Experimental Bacterial Meningitis", *Abstract of the Interscience Conference on Antimicrobial Agents and Chemotherapy*, 37, Abstract No. B-72, (1997), p. 39.

Camaioni, E, et al., "Adenosine receptor agonists: synthesis and bilogical evaluation of the diastereoisomers of 2-(3-Hydroxy-3-phenyl-1-propyn-1-yl)NECA", *Bioorganic & Medicinal Chemistry*, 5(12), (Dec. 1997), 2267-75.

Cargnoni, A., et al., "Role of $A_{2A}$ Receptors in the Modulation of Myocardial Reperfusion damage", *Journal of Cardiovascular Pharmacology* vol. 33 No. (6), (1999), pp. 883-893.

Carruthers, A. M., et al., "Hypotensive Responses to the Putative Adenosine $A_3$ Receptor Agonist $N_6$-2-(4-Aminophenyl)-Ethyladenosine in the Rat", *Drug Development Research*, 30, (1993), 147-152.

Cassada, D. C., et al., "Adenosine $A_{2A}$ agonist reduces paralysis after spinal cord ischemia: correlation with $A_{2A}$ receptor expression on motor neurons", *Annals of Thoracic Surgery*, 74(3), (Sep. 2002), 846-9; discussion 849-50.

Cassada, D. C., et al., "Adenosine $A_{2A}$ analogue ATL-146e reduces systemic tumor necrosing factor-alpha and spinal cord capillary platelet-endothelial cell adhesion molecule-1 expression after spinal cord ischemia", *Journal of Vascular Surgery*, 35(5), (May 2002).

Cassada, D C, et al., "Adenosine $A_{2A}$ analogue improves neurologic outcome after spinal cord trauma in the rabbit.", *Journal of Trauma-Injury Infection & Critical Care*, 53(2), (Aug. 2002), 225-9.

Cassada, D C, et al., "Adenosine Analogue Reduces Spinal Cord Reperfusion Injury in a Time-Dependent Fashion", *Surgery*, 130(2), (Aug. 2001), 230-235.

Cassada, D C, et al., "An adenosine $A_{2A}$ agonist, ATL-146e, reduces paralysis and apoptosis during rabbit spinal cord reperfusion.", *Journal of Vascular Surgery*, 34(3), (Sep. 2001), 482-488.

Cassada, D C, et al., "Systemic adenosine $A_{2A}$ agonist ameliorates ischemic reperfusion injury in the rabbit spinal cord", *Annals of Thoracic Surgery*, 72(4), (Oct. 2001), 1245-50.

Cavalcante, I. C, et al., "Effect of Novel $A_{2A}$ adenosine receptor agonist ATL 313 on *Clostridium difficile* toxin A-induced murin Ileal enteritis", *Infection and Immunity* 74(5), (May. 2006), 2606-2612.

Cembrzynska-Nowak, M, et al., "Elevated Release of Tumor Necrosis Factor-alpha and Interferon-gamma by Bronchoalveolar Leukocytes From Patients With Bronchial Asthma.", *American Review of Respiratory Disease*, 147(2), 1993, 291-295.

Charache, S., et al., "Effect of Hydroxyurea on the Frequency of Painful Crisis in Sickle Cell Anemia", *The New England Journal of Medicine*, 332(20), (1995), 1317-1322.

Chies, J. A. B., et al., "Sickle Cell Disease: A Chronic Inflammatory Condition", *Medical Hypothesis*, 57(1), (2001), 46-50.

Chou, T. C., et al., "Quantitative analysis of dose-effect relationships: the combined effects of multiple drugs or enzyme inhibitors", *Adv Enzyme Regul.*, 22, (1984), 27-55.

Cohen, S. B, et al., "Adenosine-2 alpha analogue augments the treatment in experimental infectious arthritis", *Poster presented at the 48th Annual Meeting of the Orthopaedic Research Society*, Dallas, USA, (Feb. 10-13, 2002), (Poster No. 0689), 1 pg.

Cothran, D. L., et al., "Ontogeny of Rat Myocardial $A_1$ Adenosine Receptors", *Biol Neonate*, 68 (2), (1995), 111-118.

Cristalli, G, et al., "2-Alkynyl Derivatives of Adenosine-5'-N-ethyluronamide: Selective A2 Adenosine Receptor Agonists with Potent Inhibitory Activity on Platelet Aggregation", *Journal of Medicinal Chemistry*, 37(11), (1994), 1720-1726.

Cristalli, G., "2-Alkynyl Derivatives of Adenosine an Adenosine-5'-N-ethyluronamide as Selective Agonists at $A_2$ Adenosine Receptors", *Journal of Medicinal Chemistry*, 35 (13), (1992), 2363-2368.

Cristalli, G., et al., "2-Alkynyl derivatives of adenosine-5'-N-ethyluronamide: selective $A_2$ adenosine receptor agonists with potent inhibitory activity on platelet aggregation.", *J Med Chem.*, 37(11), (May 27, 1994), 1720-1726.

Cristalli, G., et al., "2-Aralkynyl and 2-Heteroalkynyl Derivatives of Adenosine-5'-N-ethyluronamide as Selective $A_2$ a Adenosine Receptor Agonists", *J. Med. Chem.*, 38(9), (1995), 1462-1472.

Cristalli, G., et al., "Characterization of Potent Ligands at Human Recombinant Adenosine Receptors", *Drug Development Research*, 45, Research Overview, (1998), 176-181.

Cronstein, B N., et al., "Neutrophil Adherence to Endothelium is Enhanced Via Adenosine A1 Receptors and Inhibited Via Adenosine $A_2$ Receptors", *The Journal of Immunology*, 148 (7), (1992), 2201-2206.

Cronstein, B. N., "Adenosine Modulates the Generation of Superoxide Anion by Stimulated Human Neutrophils Via Interaction With a Specific Cell Surface Receptor", *Annals New York Academy of Science*, 451, (1985), 291-314.

Cronstein, B. N., "Adenosine, an Endogenous Anti-Inflammatory Agent", *Journal of Applied Physiology*, 76(1), (1994), 5-13.

Cronstein, B. N., "Adenosine; A Physiologic Modulator of Superoxide Anion Generated by Human Neutrophils. Adenosine Acts Via an $A_2$ Receptor on Human Neutrophils", *Journal of Immunology*, 135(2), (1985), 1366-1371.

Cronstein, B. N., "Engagement of Adenosine Receptors Inhibits Hydrogen Peroxide ($H_2O_2$) Release by Activated Human Neutrophils", *Clinical Immunology and Immunopathology*, 42(1), (1987), 76-85.

Cronstein, B. N., "Methotrexate Inhibits Leukocyte Influx Into Inflammatory Sites Via The Adenosine (A2) Receptor", *Clinical Research*, 41(2), (1993), p. 244A.

Cronstein, B. N., et al., "Occupancy of Adenosine Receptors Raises Cyclic AMP Alone and in Synergy With Occupancy of Chemoattractant Receptors and Inhibits Membrane Depolarization", *Biochemical Journal*, 252 (3), (1988), 709-715.

Cronstein, B. N., "The Adenosine/Neutrophil Paradox Resolved: Human Neutrophils Possess Both $A_1$ and $A_2$ Receptors That Promote Chemotaxis and Inhibits $O_2$ Generation, Respectively", *Journal of Clinical Investigation*, 85(4), (1990),'1150-1157.

Day, Y., et al., "$A_{2A}$ adenosine receptors on bone marrow-derived cells protect liver from ischemia-reperfusion injury", *The Journal of Immunology*, 174(8), (Apr. 15, 2005), 5040-5046.

Day, Y. J., et al., "Renal Protection from Ischemia Mediated by $A_{2A}$ Adenosine Receptors on Bone Marrow-Derived Cells.", *Journal of Clinical Investigation*, 112(6), (2003), 883-891.

Day, Y.-J., et al., "Protection From Ischemic Liver Injury by Activation of A2A Adenosine Receptors During Reperfusion: Inhibition of Chemokine Induction", *American Journal of Physiology Gastrointestinal and Liver Physiology*, 286, (2004), G285-293.

De La Harpe, J., "Adenosine Regulates the Respiratory Burst of Cytokine—Triggered Human Neutrophils Adherent to Biological Surfaces", *Journal of Immunology*, 143(2), (1989), 596-602.

De Moraes, V. L., et al., "Effect of Cyclo-Oxygenase Inhibitors and Modulators of Cyclic AMP Formation on Lipopolysaccharide-Induced Neutrophil Infiltration in Mouse Lung", *British Journal of Pharmacology*, 117, (1996), 1792-1796.

De Sarro, G., et al., "Effects of adenosine Receptor Agonists and Antagonists on Audiogenic Seizure-sensible DBA / 2 mice", *European Journal of Pharmacology*, 371, (1999), 137-145.

De Zwart, M, et al., "5-N-Substituted Carboxamidoadenosines as Agonists for Adenosine Receptors", *Journal of Medicinal Chemistry*, 42(8), (Apr. 22, 1999), 1384-1392.

Dechatelet, L R., et al., "Mechanism of the Luminol-Dependent Chemiluminescence of Human Neutrophils", *The Journal of Immunology*, 129(4), (1982), 1589-1593.

Dinarello, C. A., "Interleukin-1 and Tumor Necrosis Factor: Effector Cytokines in Autoimmune Diseases", *Seminars in Immunology*, 4, (1992), 133-145.

Doyle, M. P., et al., "Nucleoside-induced Arteriolar Constriction: a Mast Cell-dependent Response.", *American Journal of Physiology*, 266(5), (May 1994), H2042-H2050.

Elzein, E., et al., "Design, Synthesis and Biological Evaluation of 2-(4-Substituted-N-Pyrazolyl)-Adenosine Derivatives As Novel Short Acting Adenosine $A_{2A}$ Receptor Agonists", *Drug Development Research*, 50 (1), Abstracts From Purines 2000: Biochemical, Pharmacological, and Clinical Perspectives: Abstract No. 061, (May 2000), p. 64.

Entman, M. L., et al., "Inflammation in the course of early myocardial ischemia", *FASEB Journal*, vol. 5, (1991), 2529-2537.

"U.S. Appl. No. 12/487,235, Response filed Feb. 18, 2011 to Final Office Action mailed Sep. 20, 2010", 11 pgs.

"U.S. Appl. No. 12/712,022, Response filed Feb. 7, 2011 to Non Final Office Action mailed Nov. 9, 2010", 27 pgs.

"Canadian Application Serial No. 2460911, Notice of Allowance mailed Dec. 21, 2010", 1 pg.

"European Application Serial No. 02800432.3, Office Action mailed Dec. 29, 2010", 3 pgs.

"European Application Serial No. 05756108.6, Office Action mailed Feb. 3, 2011", 7 pgs.

"European Application Serial No. 05803845.6, Response filed Feb. 9, 2011 to Non Final Office Action mailed Oct. 18, 2010", 3 pgs.

"Japanese Application Serial No. 2001-504969, Response filed Jan. 7, 2011 to Office Action mailed Jul. 1, 2010", 3 pgs.

"Japanese Application Serial No. 2007-511486, Office Action mailed Feb. 8, 2011", 4 pgs.

Okusa, M. D, et al., "Enhanced protection from renal ischemic-reperfusion injury with A(2A)-adenosine receptor activation and PDE 4 inhibition.", Kidney Int., 59(6), (Jun. 2001), 2114-25.

Okusa, M. D, et al., "Selective A2A adenosine receptor activation reduces ischemia-reperfusion injury in rat kidney", Am J Physiol., 277(3 Pt 2), (Sep. 1999), F404-12.

"U.S. Appl. No. 08/272,821, Non Final Office Action mailed Mar. 9, 1998", 6 pgs.

"U.S. Appl. No. 08/272,821, Preliminary Amendment filed Jun. 20, 1997", 5 pgs.

"U.S. Appl. No. 08/272,821, Response filed Jun. 9, 2008 to Non Final Office Action mailed Mar. 9, 2008", 8 pgs.

"U.S. Appl. No. 08/272,821, Response filed Nov. 3, 1997 to Restriction Requirement mailed Oct. 2, 1997", 5 pgs.

"U.S. Appl. No. 08/272,821, Restriction Requirement mailed Oct. 2, 1997", 5 pgs.

"U.S. Appl. No. 09/543,385, Response filed Jun. 29, 2001 to Restriction Requirement mailed May 29, 2001", 2 pgs.

"U.S. Appl. No. 09/543,385, Restriction Requirement mailed May 29, 2001", 3 pgs.

"U.S. Appl. No. 10/412,726, Examiner Interview Summary mailed Nov. 30, 2010", 2 pgs.

"U.S. Appl. No. 11/222,664, Preliminary Amendment mailed Jun. 17, 2006", 4 pgs.

"U.S. Appl. No. 11/497,280, Examiner Interview Summary mailed Dec. 16, 2009", 2 pgs.

"U.S. Appl. No. 11/673,360, Non Final Office Action mailed Nov. 26, 2010", 26 pgs.

"U.S. Appl. No. 11/673,360, Response filed Jun. 17, 2010 to Final Office Action mailed Dec. 17, 2009", 25 pgs.

"U.S. Appl. No. 11/691,374, Received Jun. 17, 2010", 73 pgs.

"U.S. Appl. No. 12/338,599, Preliminary Amendment filed Feb. 20, 2009", 7 pgs.

"U.S. Appl. No. 12/338,599, Supplemental Preliminary Amendment filed Oct. 15, 2010", 3 pgs.

"U.S. Appl. No. 12/487,235 Final Office Action mailed Sep. 20, 2010", 15 pgs.

"U.S. Appl. No. 12/487,235, Examiner Interview Summary Dec. 7, 2010", 3 pgs.

"U.S. Appl. No. 12/487,235, Response filed Jun. 28, 2010 to Non Final Office Action mailed Dec. 28, 2009", 12 pgs.

"U.S. Appl. No. 12/487,265, Notice of Allowance mailed Sep. 7, 2010", 6 pgs.

"U.S. Appl. No. 12/712,022, Non-Final Office Action mailed Nov. 9, 2010", 53 pgs.

"Australian Application Serial No. 2005267706, Examiner Report mailed on Sep. 16, 2010", 2 Pgs.

"Canadian Application Serial No. 2,361,614, Notice of Allowance mailed Mar. 26, 2008", 1 pg.

"Canadian Application Serial No. 2,460,911, Office Action mailed Apr. 16, 2010", 2 pgs.

"Canadian Application Serial No. 2,460,911, Office Action Response Filed Oct. 14, 2010", 4 pgs.

"Canadian Application Serial No. 2,460,911, Response filed Dec. 14, 2009 to Non Final Office Action mailed Jun. 12, 2009", 35 pgs.

"European Application Serial No. 02800432.3, Office Action mailed Apr. 22, 2010", 3 Pgs.

"European Application Serial No. 02800432.3, Office Action Response Filed Jun. 23, 2010", 2 pgs.

"European Application Serial No. 03728372.8, Office Action mailed Apr. 11, 2005", 4 pgs.

"European Application Serial No. 03728372.8, Office Action mailed Nov. 24, 2005", 3 pgs.

"European Application Serial No. 03728372.8, Response filed Feb. 22, 2006 to Office Action mailed Nov. 24, 2005", 10 pgs.

"European Application Serial No. 03728372.8, Response filed Oct. 21, 2005 to Office Action mailed Apr. 11, 2005", 14 pgs.

"European Application Serial No. 05756108.6, Office Action mailed Aug. 6, 2010", 9 pgs.

"European Application Serial No. 05803845.6, Communication mailed Oct. 18, 2010", 4 pages.

"European Application Serial No. 10181920.9, Extended European Search Report mailed Nov. 30, 2010", 11 pgs.

"International Application Serial No. PCT/US00/14548, International Search Report mailed Feb. 1, 2001", 4 pgs.
"International Application Serial No. PCT/US00/14548, Response filed May 20, 2001 to Written Opinion mailed Feb. 27, 2001", 13 pgs.
"International Application Serial No. PCT/US00/14548, Response filed Jul. 23, 2001 to Written Opinion mailed Jun. 25, 2001", 2 pgs.
"International Application Serial No. PCT/US00/14548, Written Opinion mailed Feb. 27, 2001", 7 pgs.
"International Application Serial No. PCT/US00/14548, Written Opinion mailed Jun. 25, 2001", 4 pgs.
"International Application Serial No. PCT/US09/30565, International Search Report and Written Opinion mailed Apr. 6, 2009", 7 pgs.
"International Application Serial No. PCT/US2005/015241, International Preliminary Examination Report mailed Nov. 16, 2006", 6 pgs.
"International Application Serial No. PCT/US2005/015241, International Search Report and Written Opinion mailed Sep. 14, 2005", 10 pgs.
"International Application Serial No. PCT/US2005/027474, International Preliminary Examination Report mailed Feb. 15, 2007", 10 pgs.
"International Application Serial No. PCT/US2005/027474, International Search Report and Written Opinion mailed Jan. 25, 2006", 16 pgs.
"International Application Serial No. PCT/US2005/027475, International Preliminary Examination Report mailed Feb. 15, 2007", 7 pgs.
"International Application Serial No. PCT/US2005/027479, International Preliminary Examination Report mailed Feb. 15, 2007", 12 pgs.
"International Application Serial No. PCT/US2007/061867, International Preliminary Examination Report mailed Aug. 21, 2008", 8 pgs.
"International Application Serial No. PCT/US2007/061919, International Preliminary Examination Report mailed Aug. 21, 2008", 8 pgs.
"Japanese Application Serial No. 2000-596019, Office Action Response filed Nov. 15, 2010", 23 pgs.
"Singapore Application Serial No. 200706337-3, Response to Written Opinion Filed: Dec. 13, 2010", 15 pgs.
Abiru, T., et al., "Differential vasodilatory action of 2-octynyladenosine (YT-146), an adenosine A2 receptor agonist, in the isolated rat femoral artery and vein.", Eur J Pharmacol., 281(1), (Jul. 25, 1995), 9-15.
Adah, S. A., "Synthesis of Complex Ethynyladenosines Using Organic Triflic Enolates in Palladium-Catalyzed Reactions: Potential Agonists for the Adenosine A2 Receptor", Tetrahedron, 53, (1997), 6747-6754.
Cavalcante, I. C, et al., "Effect of Novel A2A Adenosine Receptor Agonist ATL 313 on Clostridium difficile Toxin A-Induced Murine Ileal Enteritis", Infection and Immunity, vol. 74, No. 5, (May 2006), 2606-2612.
Chow, F., et al., "Macrophages in mouse type 2 diabetic nephropathy: correlation with diabetic state and progressive renal injury", Kidney Int., 65(1), XP002593910, ISSN: 0085-2538, (Jan. 2004), 116-28.
Cristalli, G, et al., "Platelet aggregation inhibitory activity of selective A2 Adenosine Receptor Agonists", Nucleosides & Nucleotides, vol. 14 No. 3-5, (1995), 449-453.
Harada, N., et al., "Adenosine reduces ischemia/reperfusion injury of rat liver by inhibiting leukocyte activation: Involvement of adenosine A2a receptor", Jpn. J. Pharmacol., 79(Suppl), Abstract No. O-214, (1999), 89P.
Okusa, M. D, "A(2A) adenosine receptor: a novel therapeutic target in renal disease", Am J Physiol Renal Physiol., 282(1), XP002593908; ISSN : 0002-9513, (Jan. 2002), F10-8.
Okusa, Mark D, "Attenuation of renal inflammation by adenosine 2A receptor (A2A-AR) activation in ischemia-reperfusion injury (I/R) Regulation adhesion molecule and cytokine expression", 33RD Annual Meeting of the American Society of Nephrology vol. 11, No . Program and A, XP008124542; ISSN : 1046-6673, (Sep. 1, 2000), 132A.
Rieger, J. M, et al., "Design, Synthesis, and Evaluation of Novel A2A Adenosine Receptor Agonists", J. Med. Chem., 44, (2001), 531-539.
Sullivan, G. W., et al., "Neutrophil A2A Adenosine Receptor Inhibits Inflammation in a Rat Model of Meningitis: Synergy with the Type IV Phosphodiesterase Inhibitor, Rolipram", The Journal of Infectious Diseases, 180, No. 5, (1999), pp. 1550-1560.
Takahashi, T., et al., "Increased spontaneous adherence of neutrophils from type 2 diabetic patients with overt proteinuria: possible role of the progression of diabetic nephropathy.", Diabetes Care, 23(3), XP002593909; ISSN: 0149-5992, (Mar. 2000), 417-8.
"U.S. Appl. No. 11/673,360, Response filed Oct. 7, 2011 to Final Office Action mailed May 3, 2011", 19 pgs.
"U.S. Appl. No. 11/673,360, Final Office Action mailed May 3, 2011", 18 pgs.
"U.S. Appl. No. 11/673,360, Response filed Mar. 25, 2011 to Non Final Office Action mailed Nov. 26, 2010", 27 pgs.
"U.S. Appl. No. 12/338,599, Notice of Allowance mailed Jun. 28, 2011", 9 pgs.
"U.S. Appl. No. 12/487,235, Notice of Allowance mailed Mar. 25, 2011", 7 pgs.
"U.S. Appl. No. 12/712,022, Final Office Action mailed Aug. 24, 2011", 10 pgs.
"U.S. Appl. No. 12/712,022, Non Final Office Action mailed Mar. 23, 2011", 53 pgs.
"U.S. Appl. No. 12/712,022, Response filed Jun. 23, 2011 to Non Final Office Action mailed Mar. 23, 2011", 19 pgs.
"U.S. Appl. No. 13/027,901, Non Final Office Action mailed Mar. 31, 2011", 15 pgs.
"U.S. Appl. No. 13/027,901, Non Final Office Action mailed Jul. 6, 2011", 8 pgs.
"Brazil Application Serial No. PI 0007864-6,Office Action mailed May 18, 2011", 5 pgs.
"Brazil Application Serial No. PI0011725-0, Office Action mailed Jun. 9, 2011", 4 pgs.
"Brazilian Application Serial No. PI 0007864-6, Response filed Sep. 26, 2011 to Office Action mailed May 18, 2011", 12 pgs.
"Canadian Application Serial No. 2,576,826, Office Action mailed Sep. 22, 2011", 4 pgs.
"Chilean Application Serial No. 1609-00, Office Action mailed Sep. 23, 2011", 1 pg.
"Chinese Application Serial No. 200580033215.2, Non Final Office Action dated Jul. 4, 2011", 7 pgs.
"European Application Serial No. 02800432.3, Response filed Mar. 17, 2011 to Non Final Office Action mailed Dec. 29, 2010", 40 pgs.
"European Application Serial No. 05756108.6, Response filed Jul. 20, 2011 to Non Final Office Action dated Feb. 3, 2011", 22 pgs.
"European Application Serial No. 10181920.9, Office Action mailed Jul. 21, 2011", 4 pgs.
"European Divisional Application Serial No. 10181920.9, Response filed Jun. 29, 2011 to EP Search Report dated Nov. 30, 2010", 53 pgs.
"Japanese Application Serial No. 2001-504939, Final Office Action mailed Jul. 28, 2011", 6 pgs.
"Japanese Application Serial No. 2007-511486, Office Action Response filed Aug. 5, 2011 to Office Action mailed Feb. 23, 2011", 29 pgs.
"Japanese Application Serial No. 2007-524924, Office Action mailed Sep. 16, 2011", 3 pgs.
"New Zealand Application Serial No. 585697, Non Final Office Action dated Aug. 29, 2011", 2 pgs.
"New Zealand Application Serial No. 585697, Response filed Aug. 11, 2011 to Examination Report dated Jun. 3, 2010", 3 pgs.
"New Zealand Application Serial No. 585697, Response filed Sep. 28, 2011 to Office Action mailed Aug. 31, 2011", 13 pgs.
"Singapore Application Serial No. 200706337-3, Response to Written Opinion filed Oct. 3, 2011", 13 pgs.
"Singapore Application Serial No. 200706337-3, Office Action mailed May 3, 2011", 10 pgs.
Clerici, C., et al., "Effect of Intraduodenal Administrative of 23-Methyl-UDCA Diastereoisomers on Bile Flow in Hamsters", Digestive Diseases and Sciences, vol. 37, No. 5, (May 1992), 791-798.
Cristalli, Gloria, et al., "Characterization of Potent Ligands at Human Recombinant Adenosine Receptors", Characterization of Potent Ligands at Human Recombinant Adenosine Receptors. Drug Development Research 45:176-181 (1998), 176-181.

Goodwin, Jay T, et al., "Physicochemical Determinants of Passive Membrane Permeability: Role of Solute Hydrogen-Bonding Potential and Volume", J Med Chem, 44, (2001), 3721-3729.

Kerns, Edward, et al., "Drug-Like Properties: Concepts, Structure Design and Methods: From ADME to Toxicity Optimization", Elsevier, (2008), 92:96.

Nogrady, Thomas, et al., "Medicinal Chemistry: A Molecular and Biochemical Approach", Oxford University Press, 3rd Edition, (2005), 135.

Remuzon, Philippe, et al., "Fluoronaphthyridines as Antibacterial Agents. 6. Synthesis and Structure-Activity Relationships of New Chiral 7-(1-, 3-, 4-, and 6-Methyl-2, 5-Diazabicyclo [2.2.1] heptan-2-yl]-1-(1,1-dimethylethyl)-6-fluoro-1,4-di-hydro-4-oxo1, 8-naphthyridine-3- . . .", J Med Chem, 35, (1992), 2898-2909.

Silverman, R., et al., "The Organic Chemistry of Drug Design and Drug Action", Academic Press, (1992), 16-17.

Volpini, R., et al., "Synthesis of Di- and Tri-substituted Adenosine Derivatives and their Affinities at Human Adenosine Receptor Subtypes", Nucleosides & Nucleotides, 18(11&12), 2511-2520 (1999), 2511-2520.

Fabry, M. E., et al., "High Expression of Human $\beta^S$- and $\alpha$-globins in Transgenic Mice: Hemoglobin Composition and Hematological Consequences", Proc. Natl. Acad. Sci. USA, 89, (1992), 12150-12154.

Fabry, M. E., et al., "High Expression of Human $\beta^S$- and $\alpha$-globins in Transgenic Mice: Erythrocyte Abnormalities, Organ Damage, and the Effect of Hypoxia", Proc. Natl. Acad. Sci. USA, 89, (1992), 12155-12159.

Fang, G. D, et al., "ATL 146e (ATL), a Selective A[2A] Adenosine Receptor Agonist, Combined with Ceftriaxone, Markedly Improves Survival in a Mouse Model of E. coli 026:B6 Sepsis", Meeting Abstract B-1110, Presented at the 41st Interscience Conference on Antimicrobial Agents and Chemotherapy, Chicago, USA, (Dec. 16-19, 2001), 5 pgs.

Fang, G. D., et al., "DWH146e (DWH), A New Selective Adenosine $A_{2\alpha}$ Receptor Agonist, Improves Survival in E. coli O26:B6 Lipopolysaccharide (LPS)-Induced Experimental Murine Endotoxemia", Journal of Investigative Medicine, Abstract No. 797, (2000), p. 148A.

Fenster, M. S., et al., "Activation of adenosine $A_{2\alpha}$ receptors inhibits mast cell degranulation and mast cell-dependent vasoconstriction", Microcirculation, 7(2), (Apr. 2000), 129-135.

Feoktistov, I., et al., "Adenosine $A_{2B}$ receptors", The American Society for Pharmacological and Experimental Therapeutics, 49(4), (1997), 381-402.

Feoktistov, I., et al., "Role of Adenosine in Asthma", Drug Development Research, 39, (1996), 333-336.

Ferrante, A., "Optimal Conditions for Simultaneous Purification of Mononuclear and Polymorphonuclear Leucocytes From Human Blood by the Hypaque-Ficoll Method", Journal of Immunological Methods, 36(2), (1980), 109-117.

Figler, R. A., et al., "Reconstitution of Bovine $A_1$ Adenosine Receptors and G Proteins in Phospholipid Vesicles: .Beta..Gamma.-Subunit Composition Influences Guanine Nucleotide Exchange and Agonist Binding", Biochemistry, 36(51), (1997), 6288-16299.

Figler, R. A., et al., "Reconstitution of Recombinant Bovine $A_1$ Adenosine Receptors in Sf9 Cell Membranes with Recombinant G Proteins of Defined Composition.", Molecular Pharmcology, 50(6), (Dec. 1996), 1587-1595.

Firestein, G. S., "Adenosine Regulating Agents: A Novel Approach to Inflammation and Inflammatory Arthritis", Clinical Research, 41(2), (Abstract Only), (1993), p. 170A.

Fiser, S M, et al., "Adenosine $A_{2A}$ receptor activation decreases reperfusion injury associated with high-flow reperfusion.", Journal of Thoracic & Cardiovascular Surgery, 124(5), (Nov. 2002), 973-978.

Fozard, J. R., et al., "Adenosine $A_3$ Receptors Mediate Hypotension in the Angiotensin II-supported Circulation of the Pithed Rat", British Journal of Pharmacology, 109(1), (1993), 3-5.

Francis, J. E., "Highly Selective Adenosine $A_2$ Receptor Agonists in a Series of N-Alkylated 2-Aminoadenosines", Journal of Medicinal Chemistry, 34 (8), (1991), 2570-2579.

Frangogiannis, N G, et al., "The Role of the Neutrophil in Myocardial Ischemia and Reperfusion", Myocardial Iscehmia: Mechanisms, Reperfusion, Protection, M. Karmazyn, Editor, Birkhauser Verlag Basel, (1996), 236-284.

Frenette, P. S., "Sickle Cell Vasoocclusion: Heterotypic, Multicellular Aggregations Driven by Leukocyte Adhesion", Microcirculation, 11, (2004), 167-177.

Gao, Z, et al., "Purification of $A_1$ Adenosine Receptor-G-protein Complexes: Effects of Receptor Down-regulation and Phosphorylation on Coupling", Biochemical Journal, 338 (Pt3), (1999), 729-736.

Gao, Z., et al., "$A_{2B}$ Adenosine and $P2Y_2$ Receptors Stimulate Mitogen-activated Protein Kinase in Human Embryonic Kidney-293 Cells. Cross-talk Between Cyclic AMP and Protein Kinase c Pathways", Journal of Biological Chemistry, 274(9), (Feb. 26, 1999), 5972-5980.

Gilchrist, A., et al., "Antagonists of the Receptor-G Protein Interface Block Gi-coupled Signal Transduction", Journal of Biological Chemistry, 273 (24), (Jun. 12, 1998), 14912-14919.

Girardi, N, et al., "Inflammatory Aneurysm of the Ascending Aorta and Aortic Arch", Ann. Thor. Surg., 64, (1997), 251-253.

Glover, D K, et al., "Pharmacological stress myocardial perfusion imaging with the potent and selective $A_{2A}$ adenosine receptor agonists ATL193 and ATL146e administered by either intravenous infusion or bolus injection", Circulation, 104(10), (Sep. 4, 2001), 1181-1187.

Glover, D. K., et al., "Bolus Injection of DWH-146E, A Novel Adenosine $A_{2A}$ Receptor Agonist for Use in Vasodilator Stress Imaging", (Abstract No. 44.20), Journal of Nuclear Cardiology, 7 (4),, (Sep. 23, 2000), 1 pg.

Glover, D. K., et al., "Characterization of a New, Highly Selective Adenosine A2A Receptor Agonist with Potential Use in Pharmacologic Stress Perfusion Imaging", (Abstract), Circulation 100, (1999), 1 pg.

Glover, D. K., et al., "Pharmacological stress thallium scintigraphy with 2-cyclohexylmethylidenehydrazinoadenosine (WRC-0470). A novel, short-acting adenosine $A_{2A}$ receptor agonist.", Circulation, 94(7), (Oct. 1, 1996), 1726-1732.

Glover, D. K., et al., "Vasodilator Stress Imaging Using New Adenosine $A_{2A}$ Receptor Agonists Administered by Bolus Injection", J. Am. Coll. Cardiol., 35, (Abstract), (2000), 1 pg.

Griswold, D. E., et al., "Effect of Selective Phosphodieasterase Type IV Inhibitor, Rolipram, on Fluid and Cellular Phases of Inflammatory Response", Inflammation, 17(3), (1993), 333-344.

Hall, J., et al., "Abnormal Hypothalamic-Pituitary-Adrenal Axis Function in Rheumatoid Arthritis", Arthritis & Rheumatism, 37(8), (1994), 1132-1137.

Hamaguchi, M., et al., "Mechanisms and Roles of Neutrophil Infiltration in Stress-Induced Gastric Injury in Rats", Digestive Diseases and Sciences, 46(12), (2001), 2708-2715.

Hamajima, E., et al., "Effects of FK506, An Immunosuppressive Agent, on Genesis of Water-Immersion Stress-Induced Gastric Lesions in Rats", Digestive Diseases and Sciences, 39(4), (1994), 713-720.

Hanlon, W. A., "rTNFα Facilitate Human Polymorphonuclear Leukocyte Adherence to Fibrinogen Matrices With Mobilization of Specific and Tertiary But Not Azurophilic Granule Markers", Journal of Leukocyte Biology, 50 (1), (1991), 43-48.

Harada, N., et al., "Adenosine and Selective $A_{2a}$ Receptor Agonists Reduce lschemia/Reperfusion Injury of Rat Liver Mainly by Inhibiting Leukocyte Activation", The Journal of Pharmacology and Experimental Therapeutics, 294(3), (2000), 1034-1042.

Hartung, H. P., "Immune-Mediated Demyelination", Annals of Neurology, 33 (6), (Jun. 1993), 563-567.

Hasko, G., et al., "Adenosine Inhibits IL-12 and TNF-α Production via Adenosine $A_{2a}$ Receptor-Dependent and Independent Mechanisms", The FASEB Journal, 14, (2000), 2065-2074.

Hatley, M. E., et al., "Increased Production of 12/15 Lipoxygenase Eicosanoids Accelerates Monocyte/Endothelial Interactions in Diabetic db/db Mice", The Journal of Biological Chemistry, 278(28), (2003), 25369-25375.

Hebbel, R. P., "Special Issue of Microcirculation: Examination of the Vascular Pathobiology of Sickle Cell Anemia", Microcirculation, 11, (2004), 99-100.

Hebbel, R. P., et al., "The Endothelial Biology of Sickle Cell Disease: Inflammation and a Chronic Vasculopathy", *Microcirculation*, 11, (2004), 129-151.

Heller, L. J., et al., "Effect of Adenosine on Histamine Release and Atrioventricular Conduction During Guinea Pig Cardiac Anaphylaxis", *Circulation Research*, 62(6), (Jun. 1988), 1147-1158.

Hogan, C. J., et al., "Inhibiting the inflammatory response in joint sepsis", *Arthroscopy*, 17(3), (Mar. 2001), 311-315.

Holmes, Jr., D, R., et al., "Restenosis After Percutaneous Transluminal Coronary Angioplasty (PTCA): A Report From the PTCA Registry of the National Heart, Lung, and Blood Institute", *American Journal of Cardiology*, 53, (1984), 77C-81C.

Homma, H, et al., "Nucleosides and nucleotides. 112. 2-(1-Hexyn-1-yl)adenosine-5'-uronamides: a new entry of selective A2 adenosine receptor agonists with potent antihypertensive activity.", *Journal of Medicinal Chemistry*, 35(15), (Jul. 1992), 2881-90.

Hussain, T., et al., "$^{125}$I-APE Binding to Adenosine Receptors in Coronary Artery: Photoaffinity Labeling With $^{125}$I-azidoAPE", *The Journal of Pharmacology and Experimental Therapeutics*, 276 (1), (Jan. 1996), 284-288.

Hutchison, A. J., "2-(Arylalkylamino)Adenosine-5'-Uronamides: A New Class of Highly Selective Adenosine $A_2$ Receptor Ligands", *Journal of Medicinal Chemistry*, 33(7), (1990), 1919-1924.

Hutchison, A. J., "CGS 21680C, an $A_2$ Selective Adenosine Receptor Agonist With Preferential Hypotensive Activity", *The Journal of Pharmacology and Experimental Therapeutics*, 251 (1), (1989), 47-55.

Iannone, M. A., "Effects of Adenosine on Human Neutrophil Function and Cyclic AMP Content", *In: Topics and Perspectives in Adenosine Research*, Eds. E. Gerlach et al., Springer-Verlag, Berlin, Germany, (1986), 286-298.

Imagawa, D. K., et al., "The Role of Tumor Necrosis Factor in Allograft Rejection", *Transplantation*, 51, (Jan. 1991), 57-62.

Ishiwata, K., et al., "Further Characterization of a CNS Adenosine $A_{2a}$ Receptor Ligand [11C]KF18446 with in vitro Autoradiography and in vivo Tissue Uptake", *Annals of Nuclear Medicine*, 14 (2), Abstract Only, Obtained from Chemicals Abstracts, 133, (Abstract No. 346544), HCAPlus Accession No. 480897 (2000), 81-89.

Ito, B. R., et al., "Role of Cardiac Mast Cells In Complement C5a-induced Myocardial Ischemia", *American Journal of Physiology—Heart and Circulatory Physiology*, 264(5), (May 1993), H1346-H1354.

Jarvis, M. F., "[$^3$H]CGS 21680, A Selective A2 Adenosine Receptor Agonist Directly Labels $A_2$ Receptors in Rat Brain.", *Journal of Pharmacology and Experimental Therapeutics*, 251(3), (Dec. 1989), 888-893.

Jolly, S. R., "Effects of Lodoxamide on Ischemic Reperfused Myocardium", *Journal of Cardiovascular Pharmacology*, 4(3), (1982), 441-448.

Jordan, J. E., et al., "Adenosine $A_2$ Receptor Activation Attenuates Reperfusion Injury by Inhibiting Neutrophil Accumulation, Superoxide Generation and Coronary Endothelial Adherence", *The Journal of Pharmacology and Experimental Therapeutics*, 280(1), (1997), 301-309.

Kahky, M. P., et al., "Portal Infusion of Tumor Necrosis Factor Increases Mortality in Rats", *Journal of Surgical Research*, 49(2), (1990), 138-145.

Kaminuma, O., et al., "Effect of T-440, a Novel Type IV Phosphodiesterase Inhibitor, on Allergen-Induced Immediate and Late Asthmatic Reaction and Leukocyte Infiltration into the Airways of Guinea Pigs", *International Archives of Allergy & Immunology*, 112(4), (1997), 406-411.

Kanko, et al., "Protective Effects of Clopidogrel on Oxidant Damage in a Rat Model of Acute Ischemia", *Tohoku J. Exp. Med.*, 205, (2005), 133-139.

Kaul, D. K., et al., "Anti-Inflammatory Therapy Ameliorates Leukocyte Adhesion and Microvascular Flow Abnormalities in Transgenic Sickle Mice", *American Journal of Physiology—Heart and Circulatory Physiology*, 287, (2004), H293-H301.

Kaul, D. K., et al., "Hypoxia/Reoxygenation Causes Inflammatory Response in Transgenic Sickle Mice but Not in Normal Mice", *The Journal of Clinical Investigation*, 106(3), (2000), 411-420.

Keller, A. M., "Acute Reoxygeneration Injury in the Isolated Rat Heart: Role of Resident Cardiac Mast Cells", *Circulation Research*, 63(6), (Dec. 1988), 1044-1052.

Kennedy, A. P., et al., "Covalent Modification of Transmembrane Span III of the $A_1$ Adenosine Receptor With an antagonist Photoaffinity Probe.", *Molecular Pharmacology*, 50, (Oct. 1996), 789-798.

Klotz, Karl-Norbert, et al., "2-Substituted N-ethylcarboxamidoadenosine derivatives as high-affinity agonists at human $A_3$ adenosine receptors", *Naunyn-Schmiedebergs Archives of Pharmacology*, 360(2), (Aug. 1999), 103-108.

Knapp, C. M., et al., "The Type IV Phosphodiester Inhibitors, Ro 20-1724 and Rolipram,Block the Initiation of Cocaine Self Administration", *Pharmocology, Biochemistry and Behavior*,62(1), (Jan. 1999), 151-158.

Kokura, S., et al., "T-Lymphocyte-Derived Tumor Necrosis Factor Exacerbates Anoxia-Reoxygenation-Induced Neutrophil-Endothelial Cell Adhesion", *Circulation Research*, 86, (2000), 205-213.

Kollias-Baker, C., et al., "Allosteric Enhancer PD 81,723 Acts by Novel Mechanism to Potentiate Cardiac Actions of Adenosine", *Circulation Research*, 75(6), (Dec. 1994), 961-971.

Koshiba, M, et al., "Patterns of $A_{2A}$ Extracellular Adenosine Receptor Expression in Different Functional Subsets of Human Peripheral T Cells. Flow Cytometry Studies With Anti-$A_{2A}$ Receptors Monoclonal Antibodies.", *Molecular Pharmacology*, 55(3), (Mar. 1999), 614-624.

Koshiba, M., "Patterns of $A_{2A}$ Extracellular Adenosine Receptor Expression in Different Functional Subsets of Human Peripheral T Cells", (Abstract No. 703.38), *The FASEB Journal*, (1999), p. A944.

Krawisz, J. E., et al., "Quantitative Assay for Acute Intestinal Inflammation Based on Myeloperoxidase Activity", *Gastroenterology*, 87(6), (1984), 1344-1350.

Lappas, C. M, et al., "$A_{2A}$ adenosine receptor induction inhibits IFN-gamma production in murine CD4$^+$ T cells", *Journal of Immunology*, 174(2), (Jan. 15, 2005), 1073-1080.

Lard, L. R., "Neutrophil Activation in Sickle Cell Disease", *Journal of Leukocyte Biology*, 66, (1999), 411-415.

Leclerc, G., et al., "Percutaneous Arterial Gene Transfer in a Rabbit Model", *Journal of Clinical Investigation*, 90(3), (1992), 936-944.

Legrand-Poels, S., et al., "Activation of Human Immunodeficiency Virus Type 1 by Oxidative Stress", *AIDS Research and Human Retroviruses*, 6(12), (1990), 1389-1397.

Lette, J., et al., "Safety of Dipyridamole Testing in 73,806 Patients: The Multicenter Dipyridamole Safety Study", *Journal of Nuclear Cardiology*, 2(1), (1995), 3-17.

Linden, J, "Cloned Adenosine $A_3$ Receptors: Pharmacological Properties, Species Differences and Receptor Functions.", *Trends in Pharmacological Sciences*, 15(8), (Aug. 1994), 298-306.

Linden, J, et al., "The Structure and Function of $A_1$ and $A_{2B}$ Adenosine Receptors", *Life Science*, 62 (17/18),, (1998), pp. 1519-1524.

Linden, J., et al., "[$^{125}$I]Aminobenzyladenosine, a New Radioligand with Improved Specific Binding to Adenosine Receptors in Heart", *Circulation Research*, 56(2), (Feb. 1985), 279-284.

Linden, J., "Calculating the Dissociation Constant of an Unlabeled Compound from the Concentration Required to Displace Radiolabel Binding by 50%", *Journal of Cyclic Nucleotide Research*, 8(3), (1982), 163-172.

Linden, J., et al., "Chapter 2—Adenosine Receptors", *In: Handbook of Receptors and Channels—G Protein Coupled Receptors*, Peroutka, S. J., Editor CRC Press, Boca Raton, FL, (1994), 29-44.

Linden, J., "Chapter 2—Recombinant Techniques as Applied to the Study of A1 Adenosine Receptors", *In: Adenosine and Adenine Nucleotides: From Molecular Biology to Integrative Physiology*, Belardinelli, L., Editor, Kluwer Academic Publishers, Boston, (1995), 15-19.

Linden, J., "Chapter 5—Allosteric Enhancement of Adenosine Receptors", *In: Purinergic Approaches in Experimental Therapeutics*, Edited by K.A. Jacobson et al., and Published by Wiley-Liss, Inc., (1997), 85-97.

Linden, J., "Molecular Approach to Adenosine Receptors: Receptor-Mediated Mechanisms of Tissue Protection", *Annual Review of Pharmacology and Toxicology*, 41, (2001), 775-787.

Inden, J., et al., "Molecular Cloning and Functional Expression of a Sheep $A_3$ Adenosine Receptor with Widespread Tissue Distribution", *Molecular Pharmacology*, 44(3), (1993) 524-532.

Link, A. A., et al., "Ligand-Activation of the Adenosine A2a Receptors Inhibits IL-12 Production by Human Monocytes", *The Journal of Immunology*, 164, (2000), 436-442.

Lum, A. F. H., et al., "Inflammatory Potential of Neutrophils Detected in Sickle Cell Disease", *American Journal of Hematology*, 76, (2004), 126-133.

Luthin, D. R., et al., "Adenosine Receptors", *Biomembranes*, 2B, (1996), 321-347.

Luthin, D. R., "Characterization of Two Affinity States of Adenosine $A_{2a}$ Receptors With a New Radioligand, 2-[2-(4-amino-3-[$^{125}$I]iodophenyl) Ethylamino]Adenosine.", *Molecular Pharmacology*, 47(2), (Feb. 1995), 307-313.

Luthin, D. R., et al., "Comparison of $A_4$ and $A_{2a}$ Binding Sites in Striatum and COS Cells Transfected With Adesosine $A_{2a}$ Receptors.", *The Journal of Pharmacology and Experimental Therapeutics*, 272, (Feb. 1995), 511-518.

Luthin, D. R., et al., "Photoaffinity Labeling With 2(−)[2-(4-azido-3(−)[125I]-iodophenyl)ethylamino]Adenosine and Autoradiography With 2(−)[2-(4-amino-3(−)[$^{125}$I]iodophenyl)ethylamino]Adenosine of $A_{2a}$ Adenosine Receptor in Rat Brain.", *Journal of Neurochemistry*, 65(5), (Nov. 1995), 2072-2079.

Mager, P. P., "Neural network approaches applied to selective $A_{2a}$ adenosine receptor agonists", *Med. Chem. Res.*, 8(6), (1998), 277-290.

Mahan, L. C., et al., "Cloning and Expression of an $A_1$ Adenosine Receptor from Rat Brain", *Molecular Pharmacology*, 40(1), (Jul. 1991), 1-7.

Mannel, D. N., et al., "Tumor Necrosis Factor: A Cytokine Involved in Toxic Effects of Endotoxin", *Reviews of Infectious Diseases*, 9(Suppl. 5), (1987), S602-S606.

March, J.,"", *In: Advanced Organic Chemistry: Reactions, Mechanisms, and Structure*, Fourth Edition, John Wiley & Sons, (1992), p. 400.

Martin, P. L., et al., "Characterization of 8-(N-Methylisopropyl)Amino-$N^6$-(5'-Endohydroxyendonorbornyl)-9-methyladenine (WRC-0571), a Highly Potent and Selective, Nonxanthine Antagonist of $A_1$ Adenosine Receptors.", *The Journal of Pharmacology and Experimental Therapeutics*, 276(2), (Feb. 1996), 490-499.

Martin, P. L., et al., "Pharmacology of 2-cyclohexylmethylidenehydrazinoadenosine (WRC-0470), a Novel, Short-acting Adenosine $A_{2A}$ Receptor Agonist That Produces Selective Coronary Vasodilation.", *Drug Development Research*, 40(4), (1997), 313-324.

Matherne, G. P., et al., "Transgenic $A_1$ Adenosine Receptor Overexpression Increases Myocardial Resistance to Ischemia", *Proc. Natl. Acad. Sci. USA*, 94, (Jun. 1997), 6541-6546.

Matsuyama, T., "Cytokines and HIV Infection: is AIDS a Tumor Necrosis Factor Disease?", *AIDS*, 5(12), (1991), 1405-1417.

McGarrity, S. T., "Inhibition of Neutrophil Superoxide Anion Generation by Platelet Products: Role of Adenine Nucleotides", *Journal of Leukocyte Biology*, 44(5), (1988), 411-421.

McGarrity, S. T., "Regulation of Human Neutrophil Function by Adenine Nucleotides", *Journal of Immunology*, 142(6), (1989), 1986-1994.

McLaughlin, D. P., et al., "Hemodynamic and Metabolic Correlates of Dipyridamole-induced Myocardial Thallium-201 Perfusion Abnormalities in Multivessel Coronary Artery Disease.", *American Journal of Cardiology*, 73(16), (Jun. 1994), 1159-1164.

McPherson, J A, "Adenosine $A_{2A}$ receptor stimulation reduces inflammation and neointimal growth in a murine carotid ligation model", *Arteriosclerosis, Thrombosis & Vascular Biology*, 21(5), (May 2001), 791-796.

McPherson, J. A., et al., "Effect of Prolonged Adenosine A2A Receptor Activation on Neointimal Formation in the Injured Mouse Carotid Artery", (Abstract No. 299,2), *The FASEB Journal*, (1999), p. A367.

McPherson, J. A., et al., "Prolonged Adenosine A2a Receptor Stimulation Reduces Inflammation and Neointima Formation in a Murine Carotoid Ligation Model", (Abstract No. 3652), *Supplement to Circulation*, 100 (18), (Nov. 2, 1999), 1 pg.

Miyamoto, F, et al., "Retinal Cytokine Response in Mouse Alkali-Burned Eye", *Opthalmic Research*, 30, (1997), 168-171.

Mizumura, T., et al., "PD 81,723, an Allosteric Enhancer of the $A_1$ Adenosine Receptor, Lowers the Threshold for Ischemic Preconditioning in Dogs.", *Circulation Research*, 79(3), (Sep. 1996), 415-423.

Molnar-Kimber, K. L., et al., "Modulation of TNFα and IL-1 β From Endotoxin-Stimulated Monocytes by Selective PDE Isozyme Inhibitors", *Agents & Actions* 39, (1993), C77-C79.

Moore, C. C., et al., "$A_{2A}$ Adenosine Receptor Agonists Modify Inflammatory Responses in an *E. coli* Peritonitis Murine Septic Shock Model", (Abstract No. 52), *Proceedings of the 43rd Annual Meeting of the Infectious Disease Society of America*, (Oct. 6-9, 2005), p. 43.

Morabito, L., et al., "Methotrexate and Sulfasalazine Promote Adenosine Release by a Mechanism that Requires Ecto-5'-Nucleotidase-mediated Conversion of Adenine Nucleotides", *Journal of Clinical Investigation*, 101(2), (1998), 295-300.

Mumby, S. M., et al., "G-protein α-subunit expression, myristoylation, and membrane association in COS cells", *Proc. Natl. Acad. Sci. USA*. 87(2), (Jan. 1990), 728-732.

Murphree, L. J., et al., "Human $A_{2A}$ Adenosine Receptors: High-Affinity Agonist Binding to Receptor-G Protein Complexes Containing Gβ4", *Molecular Pharmacology*, 61(2), (2002), 455-462.

Nabel, E. G., "Site-Specific Gene Expression in Vivo by Direct Gene Transfer into the Arterial Wall", *Science*, 249, (1990), 1285-1288.

Nagel, R. L., et al., "Review—The Panoply of Animal Models for Sickle Cell Anaemia", British Journal of Haematology, 112, (2001), 19-25.

Needleman, J. P., et al., "Breathing Patterns During Vaso-occlusive Crisis of Sickle Cell Disease", *Chest*, 122(1), (2002), 43-46.

Newman, K. D., "Adenovirus-mediated Gene Transfer into Normal Rabbit Arteries Results in Prolonged Vascular Cell Activation, Inflammation and Neointimal Hyperplasia", *Journal of Clinical Investigation*, 96(6), (1995), 2955-2965.

Nielson, C. P., "Effects of Adenosine on Polymorphonuclear Leucocyte Function, Cyclic 3': 5'-adenosine Monophosphate, and Intracellular Calcium", *British Journal of Pharmacology*, 97(3), (1989), 882-888.

Niiya, K., "2-(N'-Alkylidenehydrazino)Adenosines: Potent and Selective Coronary Vasodilators", *Journal of Medicinal Chemistry*, 35(24), (1992), 4557-4561.

Nolte, D., et al., "Reduction of Postischemic Leukocyte-Endothelium Interaction by Adenosine via $A_2$ Receptor", *Naunyn-Schmiedeberg's Archives of Pharmacology*, 346(2), (1992), 234-237.

Odashima, M., et al., "Attenuation of Gastric Mucosal Inflammation Induced by Aspirin Through the Activation of $A_{2A}$ Adenosine Receptor in Rats", *World Journal of Gastroenterology*, 12(4), (2006), 6 pgs.

Odashima, M., et al., "Selective Adenosine $A_{2A}$ Receptor Agonist, ATL-146e, Attenuates Stress-Induced Gastric Lesions in Rats", *Journal of Gastroenterology and Hepatology*, 20(2), (2005), 275-280.

Okusa, M D, et al., "$A_{2A}$ Adenosine Receptor-Mediated Inhibition of Renal Injury and Neutrophil Adhesion", *American Journal of Physiology—Renal Fluid & Electrolyte Physiology*, 279(5), (2000), F809-F818.

Okusa, M D, et al., "Enhanced Protection from Renal Ischemia: Reperfusion Injury With $A_{2A}$-Adenosine Receptor Activation and PDE 4 Inhibition", *Kidney International*, 59(6), (2001), 2114-2125.

Okusa, M. D., et al., "Selective $A_{2A}$ adenosine receptor activation reduces ischemia-reperfusion injury in rat kidney", *Am. J. Physiol.*, vol. 277 (3, Pt 2), (1999), F404-F412.

Olah, M. E., et al., "Adenosine Receptor Subtypes: Characterization and Therapeutic Regulation", *Annual Review of Pharmacology and Toxicology*, 35, (1995), 581-606.

Olsson, R. A., et al., "$N^6$ Substituted N-Alkyladenosine-5'-Uronamides: Bifunctional Ligands Having Recognition Groups for $A_1$ and $A_2$ Adenosine Receptors", *Journal of Medicinal Chemistry*, 29(9), (1986), 1683-1689.

O'Regan, M. H., et al., "Adenosine Receptor Agonists Inhibit the Release of y-Aminobutyric Acid (GABA) From the Ischemic Rat Cerebral Cortex", *Brain Research*, 582(1), (1992), 22-26.

Orringer, E. P., et al., "Purified Poloxamer 188 for Treatment of Acute Vaso-occlusive Crisis of Sickle Cell Disease", *JAMA*, 286(17), (2001), 2099-2106.

Osuka, M. D, et al., "Enhanced protection from renal ischemia-reperfusion [correction of ischemia:reperfusion] injury with $A_{2A}$-adenosine receptor activation and PDE 4 inhibition", *Kidney Int.*, 59(6), (Jun. 2001), 2114-25.

Pathare, A., et al., "Hemoglobinopathy—Cytokines in Sickle Cell Disease", *Hematology*, 8(5), (2003), 329-337.

Peart, J, et al., "Adenosine-mediated cardioprotection in ischemic-reperfused mouse heart.", *Journal of Cardiovascular Pharmacology*, 39(1), (Jan. 2002), 117-129.

Peet, N. P., et al., "Conformationally Restrained, Chiral (Phenylisopropyl)Amino-Substituted Pyrazolo[3,4-d]Pyrimidines and Purines With Selectivity for Adenosine A1 and $A_2$ Receptors", *Journal of Medicinal Chemistry*, 35 (17), (1992), 3263-3269.

Peirce, S M, "Selective $A_{2A}$ adenosine receptor activation reduces skin pressure ulcer formation and inflammation", *American Journal of Physiology—Heart & Circulatory Physiology*, 281(1), (Jul. 2001), H67-H74.

Peirce, S. M., et al., "Attenuation of I/R Injury in Skin Using A Selective $A_{2A}$ Adenosine Receptor Agonist", *FASEB Journal, 14 (4)*, Abstract No. 333.1, (Mar. 15, 2000), page A466.

Pennell, R L, et al., "Inflammatory abdominal aortic aneurysms: A thirty-year review", *Journal of Vascular Surgery*, 2, (1985), 859-869.

Pfister, J. R., et al., "Synthesis and Biological Evaluation of the Enantiomers of the Potent and Selective $A_1$- adenosine Antagonist 1,3-dipropyl-8-[2-(5,6-epoxynorbonyl)]-xanthine", *Journal of Medicinal Chemistry*, 40 (12), (1997), 1773-1778.

Pflueger, A. C, et al., "Adenosine-Induced Renal Vasoconstriction in Diabestes Mellitus Rats: Role of Nitric Oxide", *Am. J. Physiol. Renal Physiol.*, 276, (1999), F340-F346.

Platt, O. S., et al., "Pain in Sickle Cell Disease—Rates and Risk Factors", *The New England Journal of Medicine*, 325(1), (1991), 11-15.

Platt, O. S., "Sickle Cell Anemia as an Inflammatory Disease", *The Journal of Clinical Investigation*, 106(3), (2000), 337-338.

Pulle, V., et al., "Design, Synthesis and Pharmacological Evaluation of 2(1-Alkyl-Pyrazol-4-YL) Adenosine Derivatives As Short Acting Adenosine $A_{2A}$ Receptor Agonists", (Abstract No. 062), *Drug Development Research*, 50(1), *Abstracts From Purines 2000: Biochemical, Pharmacological and Clinical Perspectives*, (May 2000), p. 64.

Raitt, M. H., et al., "Abnormal Q Waves are Common Early in AMI and Do Not Predict Decreased Myocardial Salvage With Thrombolytic Therapy", *Special Issue Journal of American College of Cardiology*, Abstract No. 895-77, (Feb. 1994), p. 195A.

Ranhosky, A., et al., "The Safety of Intravenous Dipyridamole Thallium Myocardial Perfusion Imaging", *Circulation*, 81(4), (Apr. 1990), 1205-1209.

Rashad, S., et al., "Effect of Non-Steroidal Anti-Inflammatory Drugs on the Course of Osteoarthritis", *The Lancet*, 2(8662), (Sep. 2, 1989), 519-522.

Rieger, J. M., et al., "Design, Synthesis, and Evaluation of Novel $A_{2A}$ Adenosine Receptor Agonists", *Journal of Medicinal Chemistry*, 44(4), (2001), 531-539.

Riou, L. M., et al., "Influence of propranolol, enalaprilat, verapamil, and caffeine on adenosine $A_{2A}$-receptor-mediated coronary vasodilation", *Journal of the American College of Cardiology*, 40(9), (Nov. 6, 2002), 1687-1694.

Roberts, P. A., et al., "Inhibition by Adenosine of Reactive Oxygen Metabolite Production by Human Polymorphonuclear Leucocytes", *Biochemical Journal*, 227(2), (1985), 669-674.

Robeva, A. S., et al., "Double Tagging Recombitant $A_1$- and $A_{2A}$-Adenosine Receptors With Hexahistidine and the FLAG Epitope. Development of an Efficient Generic Protein Purification Procedure.", *Biochemical Pharmacology*, 51(4), (Feb. 1996), 545-555.

Robeva, A. S., et al., "Molecular Characterization of Recombinant Human Adenosine Receptors", *Drug Development Research*, 39, (1996), 243-252.

Rosin, D. L., et al., "Immunohistochemical Localization of Adenosine $A_{2A}$ Receptors in the Rat Central Nervous System", *The Journal of Comparative Neurology*, 401, (1998), 163-186.

Ross, R., "The Pathogenesis of Atherosclerosis: A Perspective for the 1990s", *Nature*, 362, (Apr. 29, 1993), 801-809.

Ross, S. D., et al., "Selective Adenosine-$A_{2A}$ Activation Reduces Lung Reperfusion Injury Following Transplantation", *Journal of Heart & Lung Transplantation*, 18(10), (1999), 994-1002.

Ross, S. D, et al., "Selective Adenosine-A2A Activation Reduces Lung Reperfusion Injury Following Transplantation", *Journal of Heart and lung transplantation*, 18 (1), Abstract Only, Proceedings of the Nineteenth Annual Meeting and Scientific Sessions of the International Society for Heart and Lung Transplantation, San Francisco, CA, (Jan. 1999), p. 72.

Rothe, G. A., et al., "Flow Cytometric Measurement of the Respiratory Burst Activity of Phagocytes Using Dihydrorhodamine 123", *Journal of Immunological Methods*, 138(1), (1991), 133-135.

Santucci, L., et al., "Pentoxifylline Prevents Indomethacin Induced Acute Gastric Mucosal Damage in Rats: Role of Tumour Necrosis Factor Alpha", *Gut*, 35, (1994), 909-915.

Saunthararajah, Y., et al., "Effects of 5-aza-2'-deoxycytidine on Fetal Hemoglobin Levels, Red Cell Adhesion, and Hematopoietic Differentiation in Patients With Sickle Cell Disease", *Blood*, 102(12), (2003), 3865-3870.

Sawmiller, D. R., et al., "Effects of Xanthine Amine Congener on Hypoxic Resistence and Venous and Epicardial Adenosine Concentrations.", *Cardiovascular Research*, 28(5), (May 1994), 604-609.

Schiffmann, S. N., et al., "Distribution of adenosine $A_2$ receptor mRNA in the human brain", *Neuroscience Letters*, 130, (1991), 177-181.

Schlack, W., et al., "Adenosine $A_2$-Receptor Activation at Reperfusion reduces Infarct Size and Improves Myocardial Wall Function in Dog Heart", *Journal of Cardiovascular Pharmacology*, 22, (1993), 89-96.

Schrier, D. J., et al., "The Effects of Adenosine Agonists on Human Neutrophil Function", *Journal of Immunology*, 137(10), (1986), 3284-3289.

Seekamp, A., "Ischemia—Reperfusion Injury", *Agents and Actions Supplements*, 41, (1993), 137-152.

Shapiro, B. S., "The Management of Pain in Sickle Cell Disease", *Pediatric Clinics of North America*, 36(4), (1989), 1029-1041.

Sharief, M. K., et al., "Elevated Serum Levels of Tumor Necrosis Factor-α in Guillain-Barré Syndrome", *Annals of Neurology*, 33, (Jun. 1993), 591-596.

Sharma, H S, et al., "Role of cytokines in myocardial ischemia and reperfusion", *Med. of Inflamm.*, 6, (1987), 175-183.

Shay, H., et al., "A Simple Method for the Uniform Production of Gastric Ulceration in the Rat", *Gastroenterology*, 5(1), (1945), 43-61.

Sheardown, M. J, "Unexpected Neuroprotection Observed with the Adenosine $A_{2A}$ Receptor Agonist CGS 21860", *Drug Development Research*, 39, (1996), 108-114.

Shepherd, R. K., et al., "Adenosine-induced Vasoconstriction in Vivo. Role of the Mast Cell and A3 Adenosine Receptor.", *Circulation Research*, 78 (4), (Apr. 1996), 627-634.

Shi, W., et al., "Endothelial Responses to Oxidized Lipoproteins Determine Genetic Susceptibility to Atherosclerosis in Mice", *Circulation*, 102, (2000), 75-81.

Silverman, R., "Chapter 2, Drug Discovery, Design and Development", *The Organic Chemistry of Drug Design and Drug Action*, San Diego : Academic Press, (1992), 4-47.

Sipka, S., et al., "Adenosine Induced Delay of Expression of AIDS Virus, HIV, in H9T Cells", *Acta. Biochimica et Biophysica Hungarica*, 23(1), (1988), 75-82.

Siragy, H. M., et al., "Sodium Intake Markedly Alters Renal Interstitial Fluid Adenosine", *Hypertension*, 27 (3 Pt 1), (Mar. 1996), 404-407.

Smits, P., et al., "Cardiovascular effects of two xanthines and the relation to adenosine antagonism", *Clinical Pharmacology and Therapeutics*, 45(6), (1989), 593-599.

Solovey, A., "Circulating Activated Endothelial Cells in Sickle Cell Anemia", *The New England Journal of Medicine*, 337(22), (1997), 1584-1590.

Solovey, A., et al., "Tissue Factor Expression by Endothelial Cells in Sickle Cell Anemia", *Journal of Clinical Investigation*, 101(9), (1998), 1899-1904.

Steinberg, M. H., et al., "Effect of Hydroxyurea on Mortality and Morbidity in Adult Sickle Cell Anemia", *JAMA*, 289(13), (2003), 1645-1651; (Correction, published in JAMA, 290(6) (2003) at p. 756).

Stuart, M. J., et al., "Sickle-Cell Disease", *The Lancet*, 364, (2004), 1343-1360.

Sullivan, G. W., et al., "Interactions of Human Neutrophils with Leukotoxic Streptococci", *Infection and Immunity*, 30 (1), (1980), 272-280.

Sullivan, G. W., "$A_{2A}$ Adenosine Receptor Activation Improves Survival in Mouse Models of Endotoxemia and Sepsis", *Journal of Infectious Diseases*, 189(10), (May 15, 2004), 1897-1904.

Sullivan, G. W., "Adenosine (ADO) Modulates Endotoxin and TNF-Induced PMN Activation", *Clinical Research*, 41(2), (1993), p. 172A.

Sullivan, G. W., et al., "Adenosine and Related Compounds Counteract Tumor Necrosis Factor ~a Inhibition of Neutrophil Migration: Implication of a Novel Cyclic AMP-Independent Action on the Cell Surface", *The Journal of Immunology*, 145(5), (1990), 1537-1544.

Sullivan, G. W., et al., "Neutrophil $A_{2A}$ Adenosine Receptor Inhibits Inflammation in a Rat Model of Meningitis: Synergy with the Type IV Phosphodiesterase Inhibitor, Rolipram", *The Journal of Infectious Diseases*, 180(5), (1999), 1550-1560.

Sullivan, G. W., et al., "Role of $A_{2A}$ Adenosine Receptors in Inflammation", *Drug Development Research*, 45 (3/4), (1998), 103-112.

Sullivan, G. W., et al., "The role of inflammation in vascular diseases", *Journal of Leukocyte Bilogy*, 67, (May 2000), 591-602.

Sullivan, G. W., et al., "The Specific Type IV Phosphodiesterase Inhibitor Rolipram Combined with Adenosine Reduces Tumor Necrosis Factor-a-Primed Neutrophil Oxidative Activity", *International Journal of Immunonopharmacology*, 17(10), (1995), 793-803.

Sullivan, G. W., et al., "Cyclic AMP-Dependent Inhibition of Human Neutrophil Oxidative Activity by Substitued 2-Propynylcyclohexyl Adenosine $A_{2A}$ Receptor Agonists", *British Journal of Pharmacology*, 132(5), (2001), 1017-1026.

Takeuchi, K., et al., "Oxygen Free Radicals and Lipid Peroxidation in the Pathogenesis of Gastric Mucosal Lesions Induced by Indomethacin in Rats", *Digestion*, 49(3), (1991), 175-184.

Takiguchi, Y., et al., "Early administration of YT-146, an adenosine $A_2$ receptor agonist, inhibits neointimal thickening after rat femoral artery endothelium injury", *European Journal of Pharmacology 281* (1995), 205-207

Tomer, A., "Platelet Activation as a Marker for in vivo Prothrombotic Activity: Detection by Flow Cytometry", *Journal of Biological Regulators and Homeostatic Agents*, 18, (2004), 172-177.

Topol, E. J., et al., "Randomised Trial of Coronary Intervention With Antibody Against Platelet IIb/IIIa integrin for Reduction of Clinical Restenosis: Results at Six Months", *The Lancet*, 343(8902), (1994), 881-886.

Tracey, K. J., "Cachectin/Tumor Necrosis Factor Induces Cachexia, Anemia, and Inflammation", *Journal of Experimental Medicine*, 167, (Mar. 1988), 1211-1227.

Tucker, A. L., et al., "$A_1$ adenosine receptors. Two amino acids are responsible for species differences in ligand recognition", *Journal of Biological Chemistry*, 269(45), (Nov. 11, 1994), 27900-27906.

Turhan, A., et al., "Primary Role for Adherent Leukocytes in Sickle Cell Vascular Occlusion: A New Paradigm", *Proc. Natl. Acad. Sci. USA*, 99(5), (2002), 3047-3051.

Ueeda, M., et al., "2-Alkoxyadenosines: Potent and Selective Agonists at the Coronary Artery A2 Adenosine Receptor", *Journal of Medicinal Chemistry*, 34(4), (1991), 1334-1339.

Ukena, D., et al., "Species Differences in Structure-Activity Relationships of Adenosine Agonists and Xanthine Antagonists at Brain $A_1$ Adenosine Receptors", *FEBS Letters*, 209 (1), (Dec. 1986), 122-128.

Underwood, D. C., et al., "Inhibition of Antigen-Induced Bronchoconstriction and Eosinophil Infiltration in the Guinea by the Cyclic AMP-Specific Phosphodiesterase Inhibitor, Rolipram", *The Journal of Pharmacology and Experminetal Therapeutics*, 266(1), (1993), 306-313.

Van Calker, D., et al., "Adenosine Regulates via Two Different Types of Receptors, the Accumulation of Cyclic AMP in Cultured Brain Cells", *Journal of Neurochemistry*, 33,, (1979), 999-1005.

Van Calker, D., et al., "Carbamazepine Distinguishes Between Adenosine Receptors That Mediate Different Second Messenger Responses", *European Journal of Pharmacology*, 206 (4), (1991), 285-290.

Venes, et al., "Taber's Cyclopedic Medical Dictionary", *Taber's Cyclopedic Medical Dictionary*, 19, 960-961, 2001.

Vittori, S, et al., "2-alkenyl and 2-alkyl derivatives of adenosine and adenosine-5'-N-ethyluronamide: different affinity and selectivity of E- and Z-diastereomers at A2A adenosine receptors.", *Journal of Medicinal Chemistry*, 39(21), (Oct. 1996), 4211-7.

Volpini, R., et al., "Synthesis of Di- and Tri-Substituted Adenosine Derivatives and Their Affinities at Human Adenosine Receptor Subtypes", *Nucleosides & Nucleotides*, 18 (11,12), (1999), 2511-2520.

Wagner, M. C., "Sickle Cell Adhesion Depends on Hemodynamics and Endothelial Activation", *J. Lab. Clin. Med.*, 144, (2004), 260-267.

Walker, B. A., et al., "Adenosine $A_{2a}$ Receptor Activation Delays Apoptosis in Human Neutrophils", *The Journal of Immunology*, 158, (1997), 2926-2931.

Walker, D I, et al., "Inflammatory Aneurysms of the Abdominal Aorta", *Brit. J. Surg.*, 59, (1972), 609-614.

Wallace, J. L., et al., "Gastric Ulceration Induced by Nonsteroidal Anti-Inflammatory Drugs is a Neutrophil-Dependent Process", *American Journal of Physiology Gastrointestinal and Liver Physiology*, 259, (1990), G462-G467.

Wan, A. A., et al., "Binding of the Adenosine $A_2$ Receptor Ligand ($^3$H)CGS 21680 to Human and Rat Brain: Evidence for Multiple Affinity Sites", *Journal of Neurochemistry*, 55, (1990), 1763-1771.

Webster, M., "Merriam-Webster's Collegiate Dictionary", *Tenth Edition*, (1998), 924 and 935.

Weiner, D. L., "Preliminary Assessment of Inhaled Nitric Oxide for Acute Vaso-occulsive Crisis in Pediatric Patients With Sickle Cell Disease", *JAMA*, 289(9), Correction, published in JAMA, 292(8), (2004) at p. 925, (2003), 1136-1142.

Wolff, A. A., et al., "Ventricular Arrhythmias Parallel Cardiac Histamine Efflux After Coronary Artery Occlusion in the Dog", *Agents and Actions*, 25 (3/4), (1988), 296-306.

Wood, K C., et al., "Endothelial Cell P-Selectin Mediates a Proinflammatory and Prothrombogenic Phenotype in Cerebral Venules of Sickle Cell Transgenic Mice", *American Journal of Physiology—Heart and Circulatory Physiology*, 286, (2004), H1608-H1614.

Wun, T., et al., "Platelet-Erythrocyte Adhesion in Sickle Cell Disease", *Journal of Investigative Medicine*, 47(3), (1999), 121-126.

Yale, S. H., et al., "Approach to the Vaso-Occlusive Crisis in Adults With Sickle Cell Disease", *American Family Physician*, 61(5), Correction, published in American Family Physician, 64(2) (2001), p. 220, (2000), 1349-1356, 1363-1364.

Yoneyama, F., "Vasodepressor Mechanisms of 2-(1-octynyl)-Adenosine (YT-146), a Selective Adenosine $A_2$ Receptor Agonist, Involve the Opening of Glibenclamide-sensitive K+ Channels", *European Journal of Pharmacology*, 213(1), (1992), 199-204.

Yoshida, N., et al., "Role of Neutrophil-Mediated Inflammation in Aspirin-Induced Gastric Mucosal Injury", *Digestive Diseases and Sciences*, 40(11), (1995), 2300-2304.

Yoshikawa, T., et al., "Augmentative Effects of Tumor Necrosis Factor-Alpha (Human, Natural Type) on Polymorphonuclear Leukocyte-Derived Superoxide Generation Induced by Various Stimulants", *International Journal of Immunopharmacology*, 14(8), (1992), 1391-1398.

Yoshikawa, T., et al., "Role of Active Oxygen, Lipid Peroxidation, and Antioxidants in the Pathogenesis of Gastric Mucosal Injury Induced by Indomethacin in Rats", *Gut*, 34(6), (1992), 732-737.

Zablocki, J., et al., "Novel Short Acting Coronary Vasodilators That Are Functionally Selective for the A2A Receptor Based on 2-Heterocyclic Substituted Adenosine Derivatives", *Drug Development Research*, 50(1), Abstracts From Purines 2000: Biochemical, Pharmacological and Clinical Perspectives: Abstract No. 059, (May 2000), p. 63.

Zhang, X., et al., "Cellular Accumulation and Retention of the Technetium-99m-Labelled Hypoxia Markers BRU59-21 and Butylene Amine Oxime", *Nuclear Medicine and Biology*, 28, (2001), 949-957.

Zipursky, A., et al., "Oxygen Therapy in Sickle Cell Disease", *The American Journal of Pediatric Hematology/Oncology*, 14(3), (1992), 222-228.

* cited by examiner

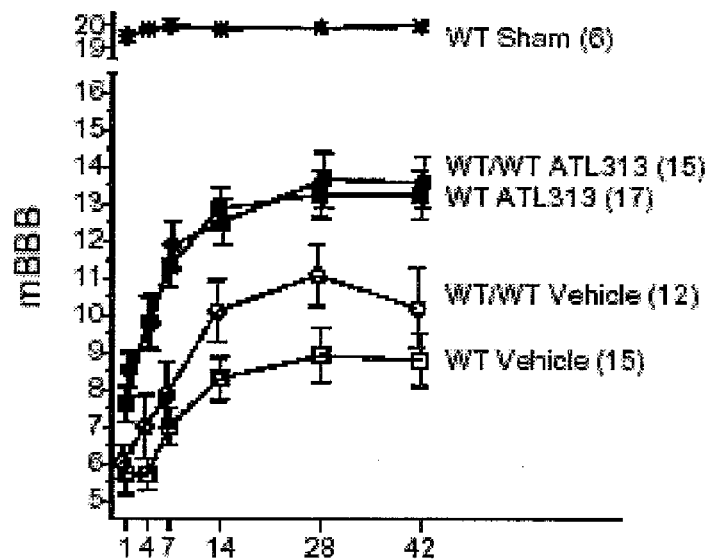
FIG. 5A
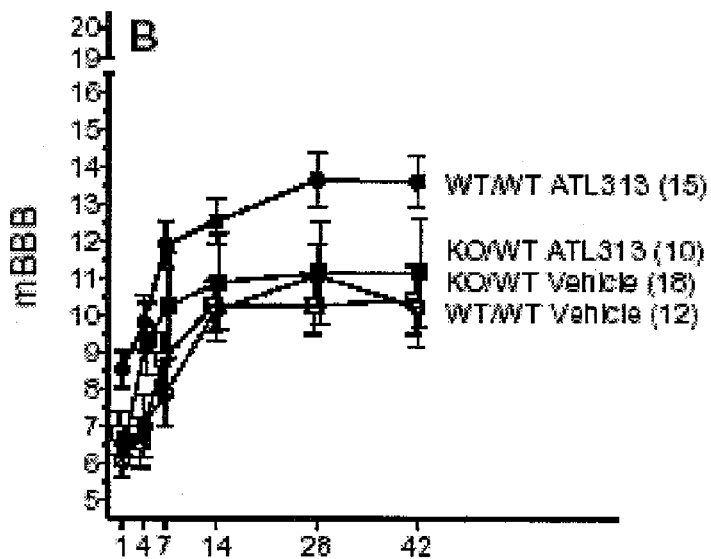
FIB. 5B

USE OF ADENOSINE $A_{2A}$ MODULATORS TO TREAT SPINAL CORD INJURY

PRIORITY OF INVENTION

This application claims priority from U.S. Provisional Application Ser. No. 60/814,713, filed Jun. 19, 2006, the disclosure of which is incorporated by reference.

GOVERNMENT FUNDING

This invention was made with United States Government support under Grant No. R01 HL37942 awarded by the National Institutes of Health. The United States Government has certain rights in this invention.

BACKGROUND

Spinal cord injury can result from trauma, e g., in a car accident or fall from a horse, or from spinal cord ischemia which can occur during surgery that necessitates clamping the aorta, such as repair of vascular tears. Agonists of $A_{2A}$ adenosine receptors have been reported to reduce spinal cord inflammation and injury when administered immediately after spinal cord ischemia or trauma.

Adenosine signals through four G protein-coupled receptors: $A_1$, $A_{2A}$, $A_{2B}$, and $A_3$. Selective activation of $A_{2A}$Rs inhibits pro-inflammatory responses in bone marrow-derived cells including platelets, monocytes, some mast cells, neutrophils and T cells. $A_{2A}$ agonists have been found to protect many tissues, including heart, liver, kidney, and skin from ischemia-reperfusion injury when added during the reperfusion period. $A_{2A}$ agonists also have been found to reduce locomotor dysfunction following ischemia-reperfusion of traumatic injury to rabbit or pig spinal cord. This occurs at low doses that have no cardiovascular effects but that reduce spinal cord inflammation during reperfusion. Consistent with tissue protection mediated by endogenous adenosine acting on $A_{2A}$Rs, deletion of the $A_{2A}$R gene has been shown to exacerbate liver and kidney reperfusion injury.

Currently, there is a need for methods and compounds for treatment or prevention of injuries to cells in the central nervous system (CNS).

SUMMARY

Agonists of the $A_{2A}$ receptors and antagonists of the $A_{2A}$ receptors or deletion of the $A_{2A}$ receptor gene has been found to protect the brain and spinal cord from ischemic injury. The present invention provides a therapeutic method for preventing a CNS injury or treating injured cells in the CNS in a mammal, comprising administering to a mammal in need thereof a therapeutically effective amount of at least one $A_{2A}$ adenosine receptor modulator. In one embodiment, the method includes first administering at least one $A_{2A}$ adenosine receptor agonist, followed by administering at least one $A_{2A}$ adenosine receptor antagonist. The $A_{2A}$ adenosine receptor agonist can be administered before an injury occurs to CNS cells or from about 1 to about 12 hours after an injury to CNS cells. After about 1-2 days the $A_{2A}$ adenosine receptor antagonist can be administered.

The invention also provides for the use of at least one $A_{2A}$ adenosine receptor modulator compound to prepare a medicament for use in preventing or treating CNS injuries in a mammal, such as a human.

The above summary of the present invention is not intended to describe each disclosed embodiment or every implementation of the present invention. Other features, objects, and advantages of the invention will be apparent from the description and drawings, and from the claims. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying drawing and the description below. Other features, objects, and advantages of the invention will be apparent from the description and drawings, and from the claims.

BRIEF DESCRIPTION OF THE FIGURES

FIGS. 3A-3C and FIGS. 3G-3I show low magnification images (10×, 200 µm/bar). FIGS. 3D-3F show medium magnification images (40×, 50 µm/bar) of the boxed areas between the dorsal medial sulcus and central canal of the corresponding panels just above. Panels FIGS. 3G-3I show variable amounts of myelin stained blue with EC. FIGS. 3J-3L show high magnification images (100×, 20 µm/bar) of the boxed areas within the anterior lateral fasciculus of the corresponding panels described above.

FIG. 5A, FIG. 5B and FIG. 5C illustrate the effect of the compound ATL313 on locomotor function in bone marrow chimera mice following spinal cord compression. BMT mice were injured and injected IP with vehicle or ATL313 and evaluated to assess locomotor function as described in methods. A) Effects of ATL313 in WT and WT/WT chimera. B)

ATL313 protects WT/WT but not KO/WT chimera. C) Effect of ATL313 in WT/KO chimera. A statistical analysis of the plateau data is shown in FIGS. 6A and 6B.

Figure 5C:
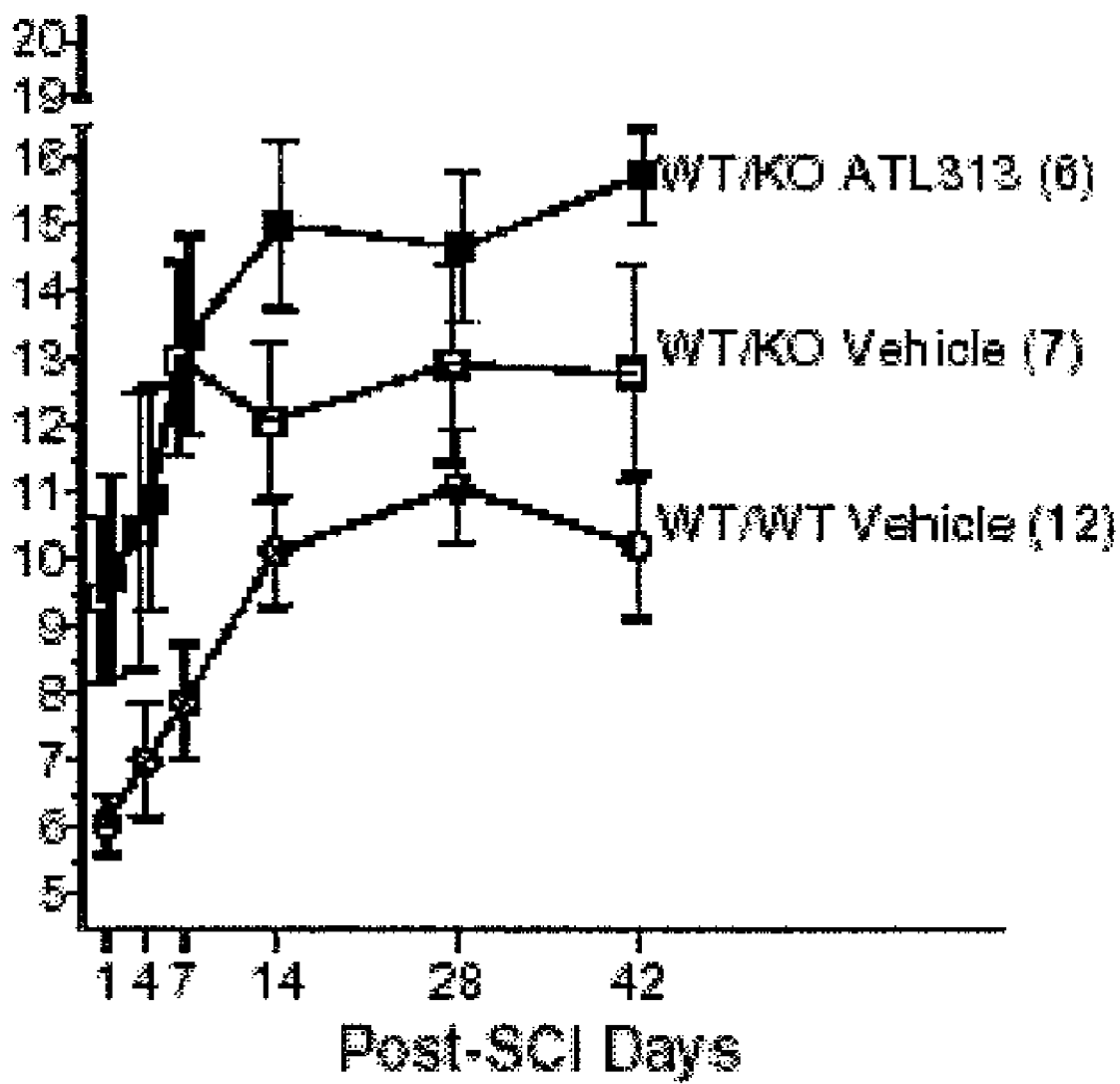
Figure 6A:
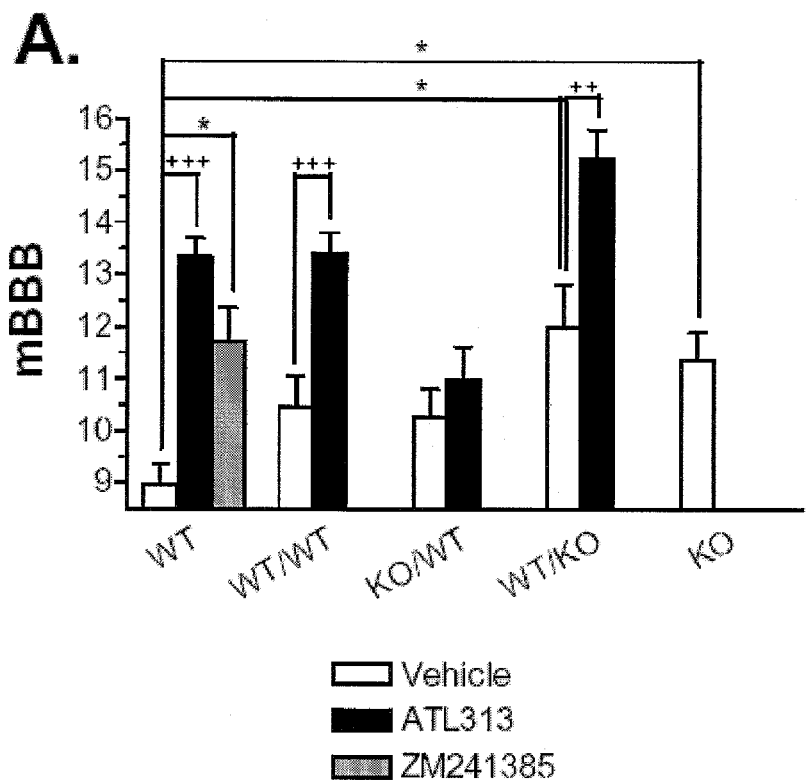
Figure 6B:
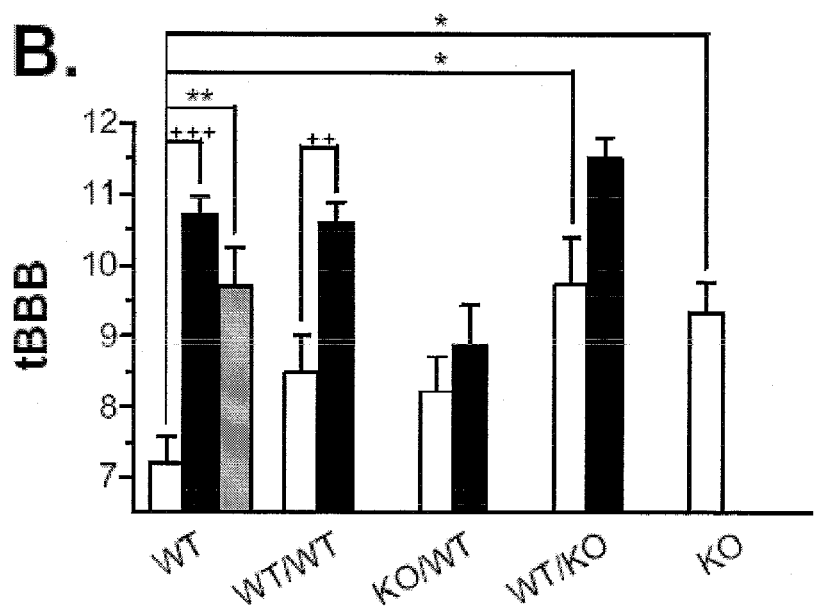

FIG. 6A. and FIG. 6B illustrate a summary of the effects of drugs and mouse genotype on the plateau phase of locomotor function following spinal cord compression. Data from the plateau phase (days 14-42) from FIG. 5 were averaged and plotted as mBBB scores (A) and tBBB scores (B). Bonferroni post-tests were conducted using *one-way or +two-way ANOVA analyses (genotype and drug), *p<0.05, **p<0.01, ++p<0.01, and +++p<0.001.

Figure 7:
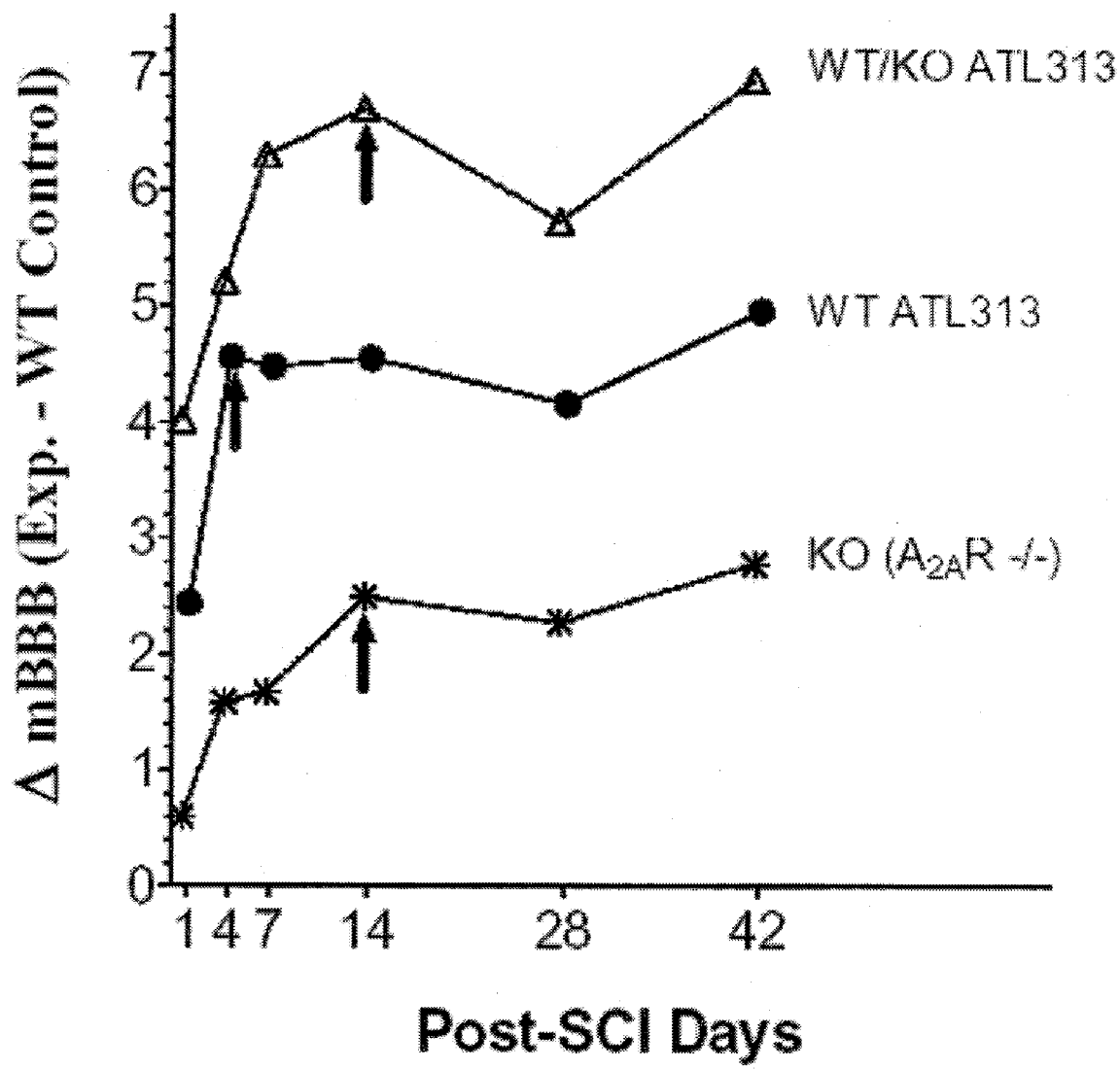

FIG. 7. illustrates a time course of changes in locomotor dysfunction following a spinal cord compression. The average daily mBBB scores from injured WT mice (n=15) were subtracted form ATL313-treated wild type (WT ATL313, n=17), ATL313-treated chimera (WT/KO ATL313, n=6), and KO (n=12) mice as indicated to reveal relative changes in locomotor function. Arrows indicate the time required for locomotor responses to reach a plateau.

Figure 8:
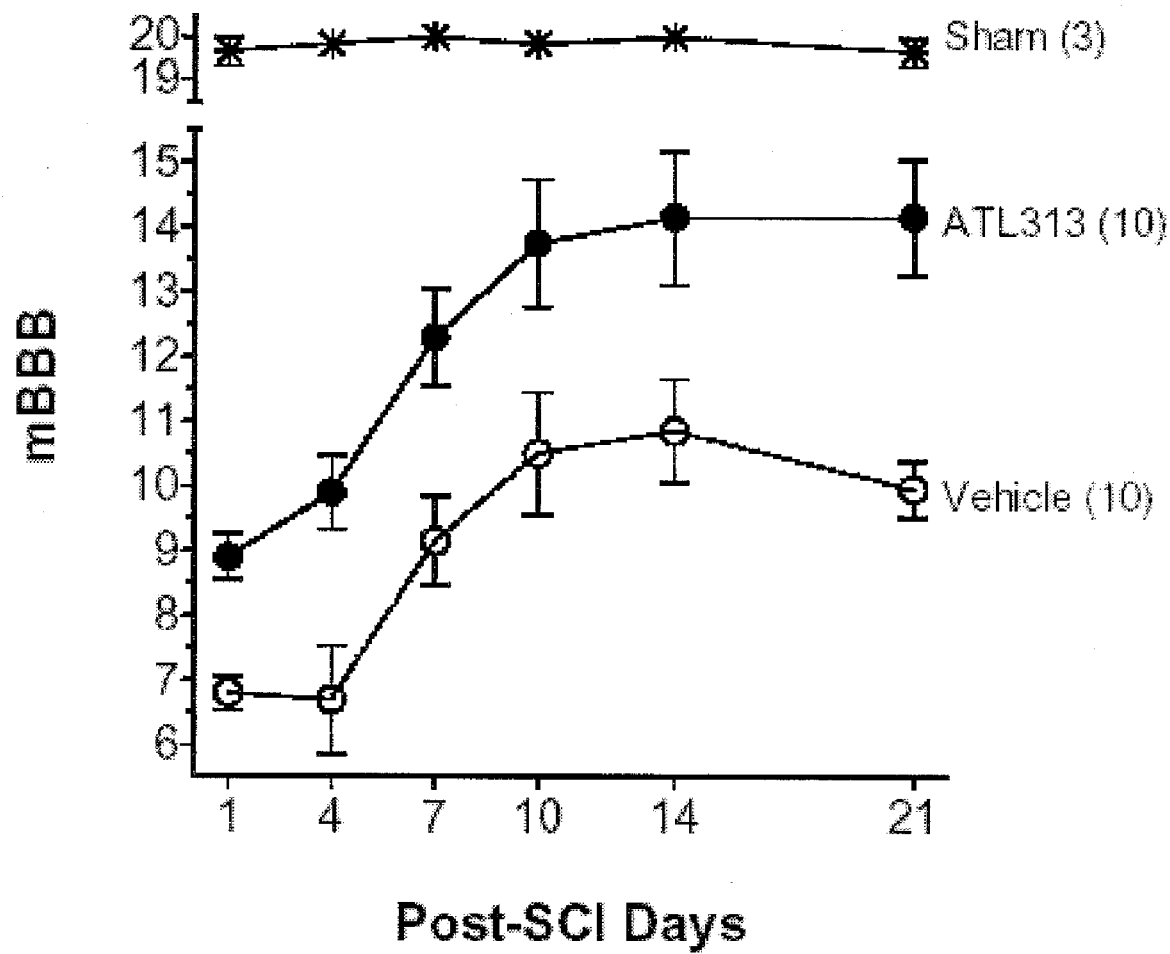

FIG. 8. is an illustration the effect of $A_{2A}$ agonist compound ATL313 on spinal cord compression. ATL313 reduces locomotor dysfunction when administered just after the onset of reperfusion. Mice were injected IP with vehicle (3% DMSO in PBS, n=10) or 6 nmol/kg ATL313 (N=10) 10-15 seconds after terminating spinal cord compression and evaluated to assess locomotor function as described in methods. The resulting protection from locomotor dysfunction is similar to protection observed when the ATL313 treatment was initiated prior to spinal cord compression (see FIG. 2).

Figure 9:
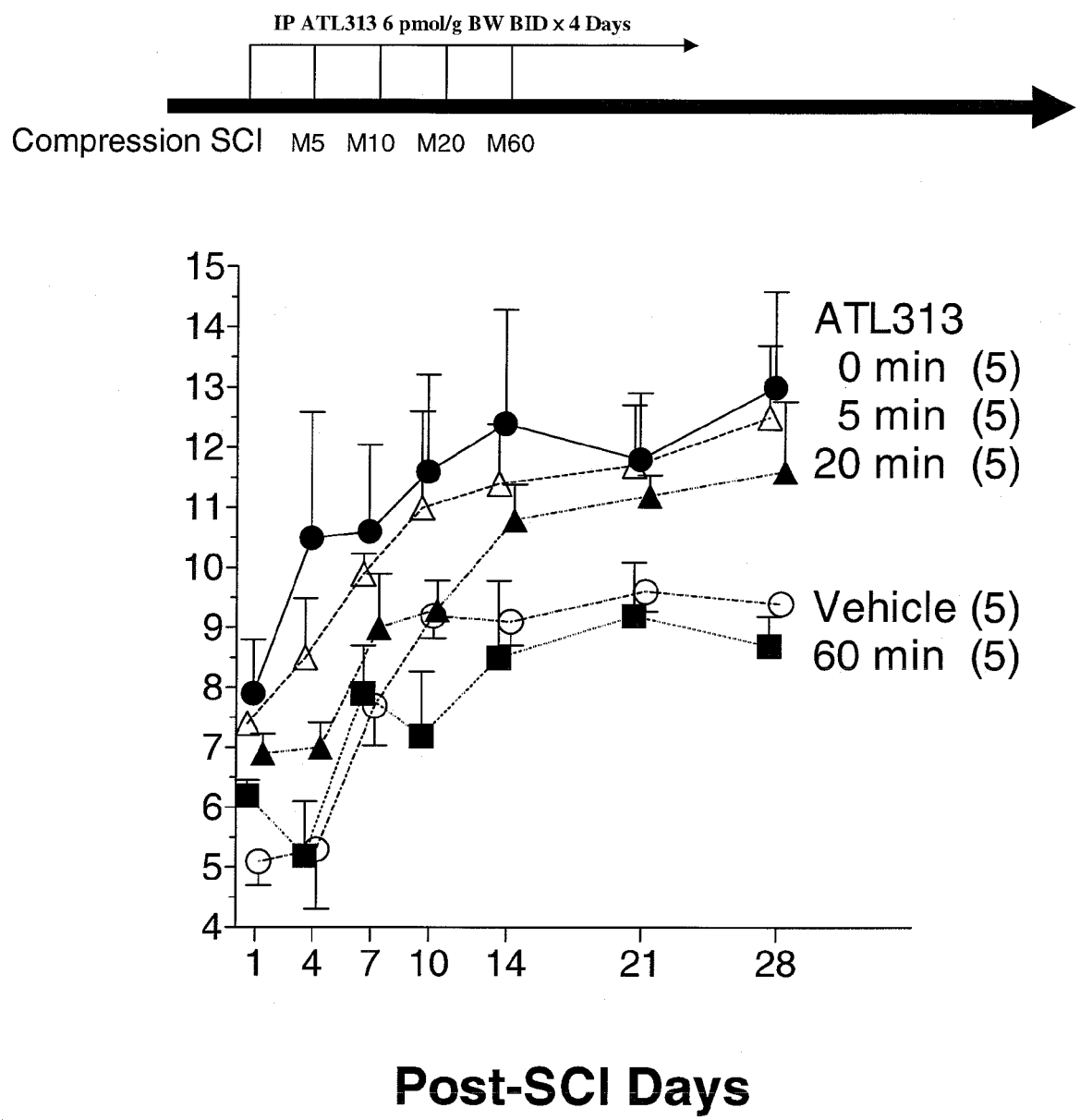

FIG. 9. illustrates the effect of delaying administration of the agonist ATL313 on compressive spinal cord injury. Protection is partially and completely reversed by 20 and 60 minutes of delay, respectively.

Figure 10:
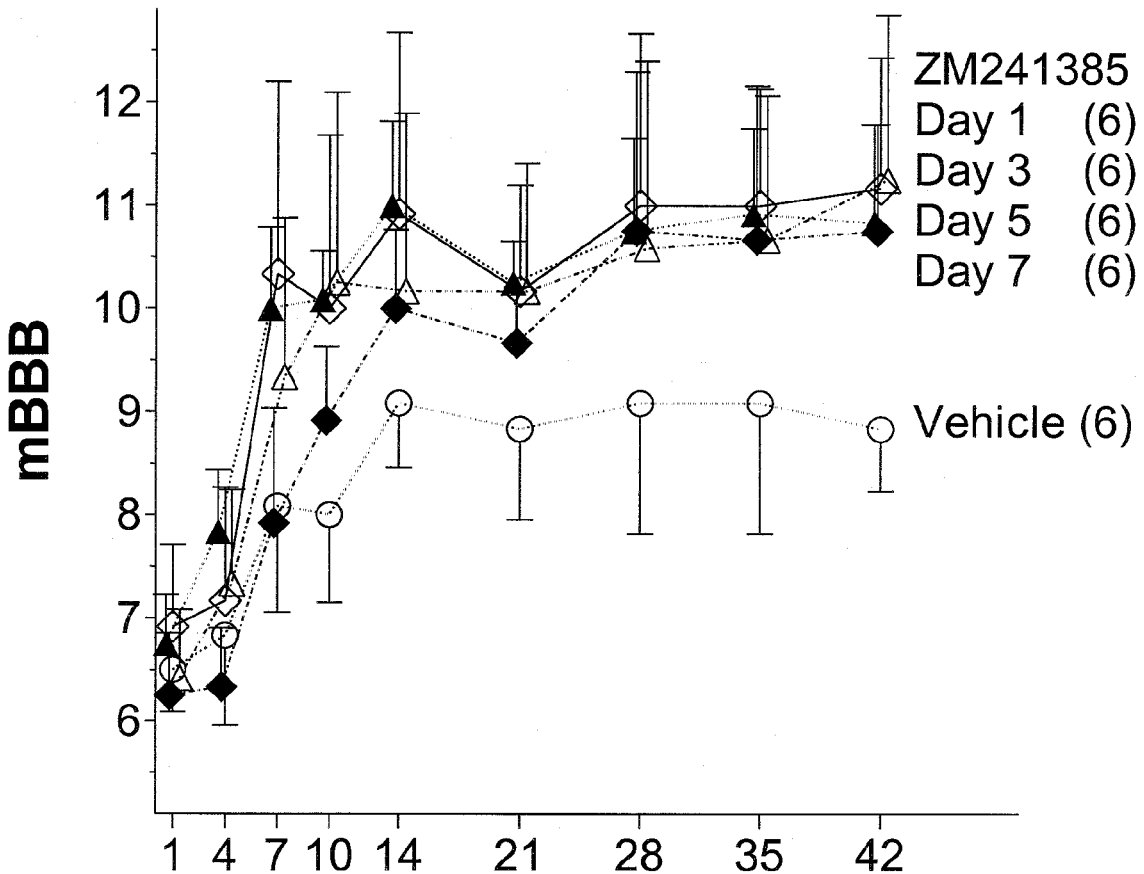

FIG. 10. illustrates the effect of delaying administration of the antagonist ZM241385 on compressive spinal cord injury. Protection is maintained even after delaying treatment for 7 days.

Figures 11A, 11B:
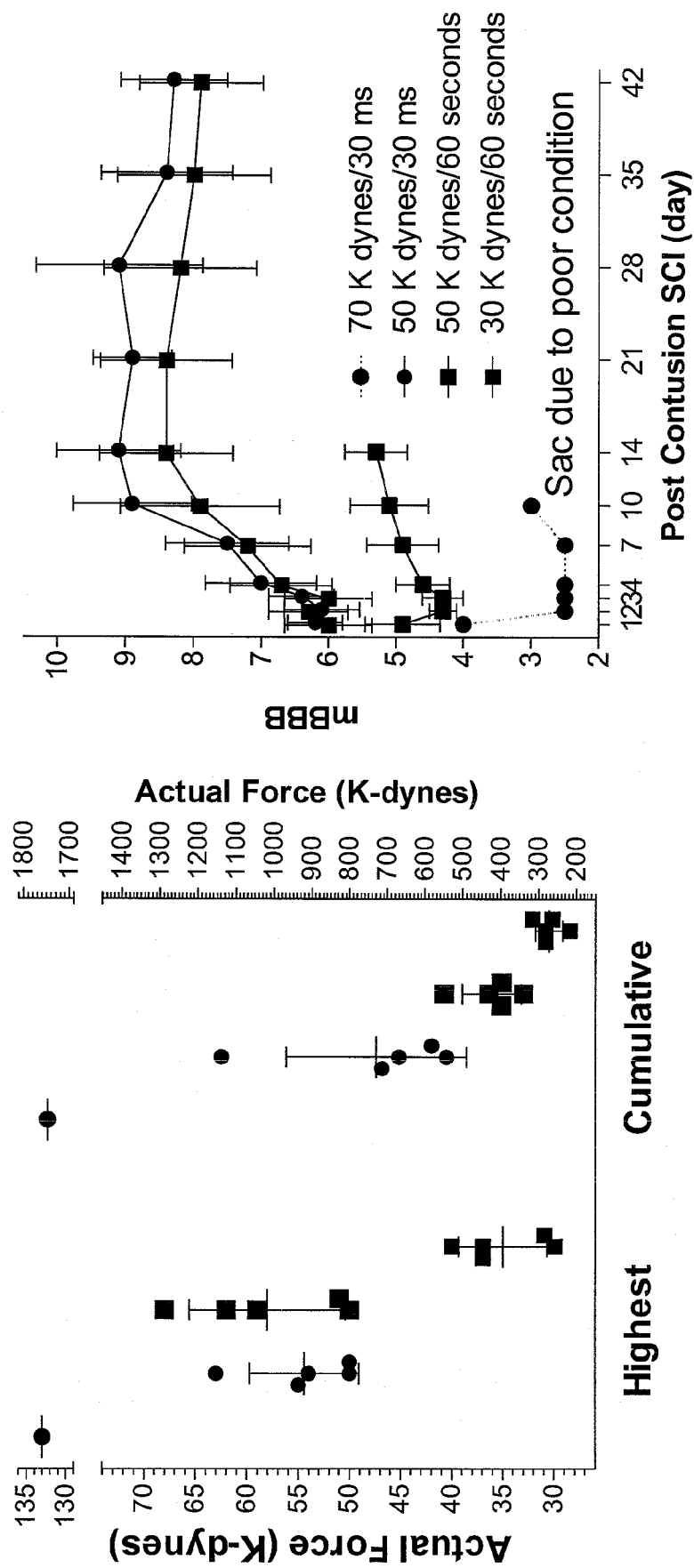

FIGS. 11A and 11B illustrate the effect of force and time of contusion on contusive spinal cord injury. FIG. 11A illustrates the force delivered by programmable contusive injury device (IH device); maximal force generated (highest) and integrated force (cumulative). Data are the means±SD, N=5 except the 70 K-dynes group (n=1). FIG. 11B illustrates the recovery of locomotor function after contusion injury. Injury produced by 50 K dynes/60 sec is greater (small score) that the injury cause for 30 K dynes/60 sec or 50 K dynes/30 msec as assessed by two way ANOVA analysis with Bonferonni post testing. In subsequent experiments 50 K dynes/30 msec was used to produce spinal cord injury.

Figure 12:
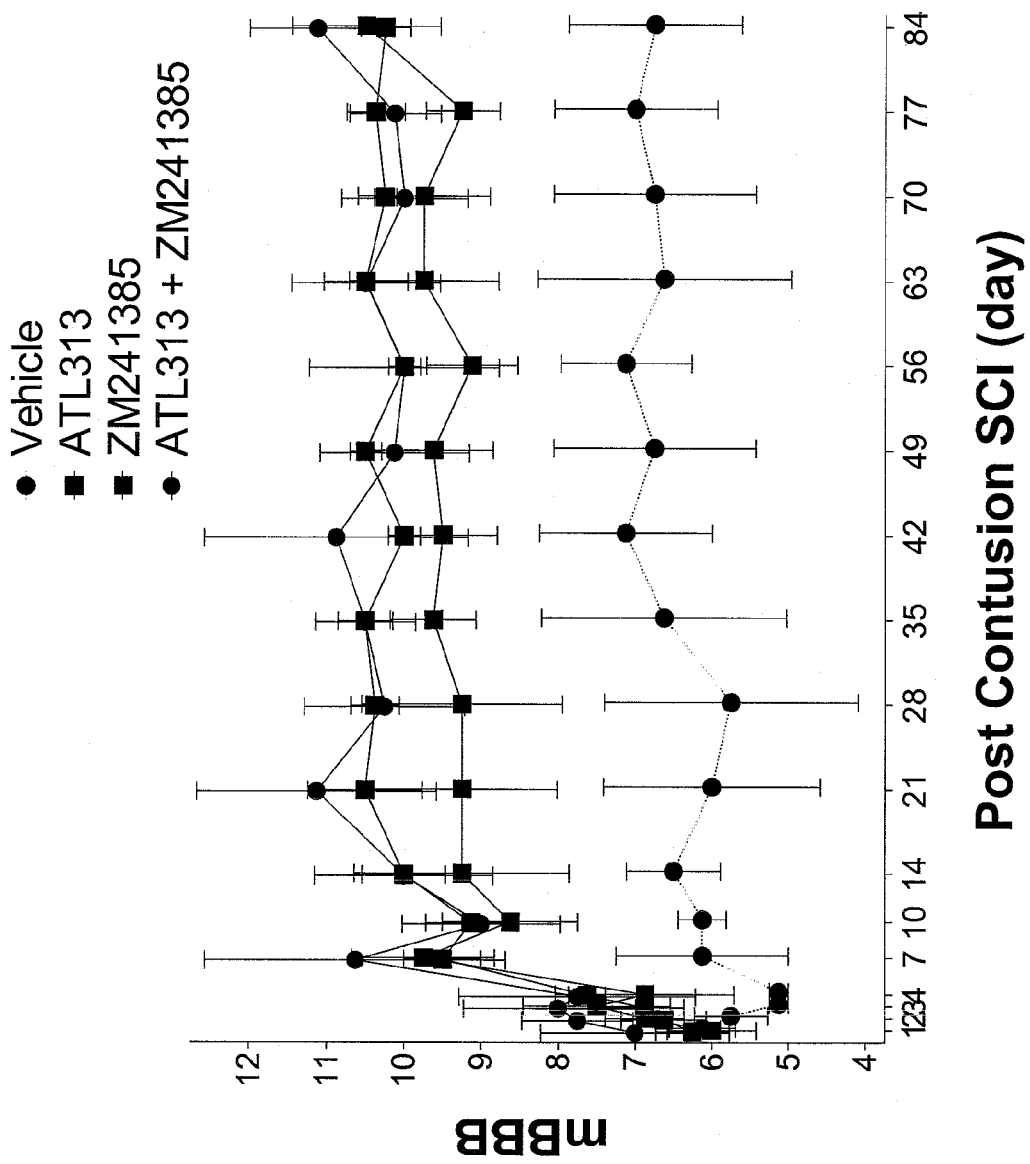

FIG. 12. illustrates the protective effect from contusive spinal cord injury by an $A_{2A}$ receptor agonist, an $A_{2A}$ receptor antagonist, or both. All drug-treated animas had less locomotor dysfunction than vehicle control. No significant differences were noted between the drug treatment groups.

Figure 13:
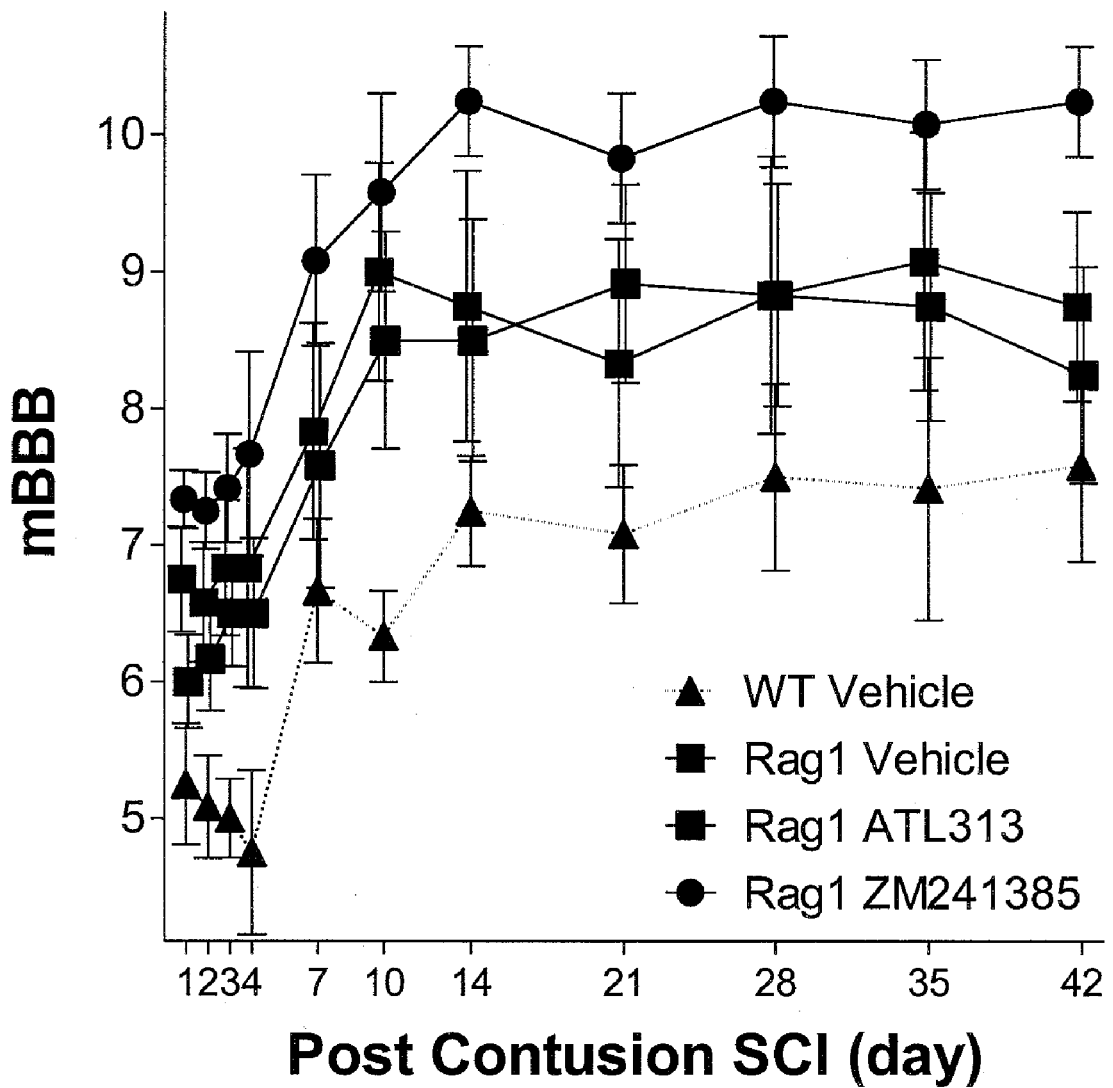

FIG. 13. illustrates the protective effect from contusive spinal cord injury in Rag1 KO mice that lack mature lymphocytes. Compared to vehicle controls, there was a trend toward improved locomotor function after contusive injury in Rag1 KO mice (P=0.08) but no evidence of additional protection by ATL313. Compared to vehicle, ZM241385 in Rag1 KO mice produced significant protection (P=0.0015), but did not significantly improve protection compared to Rag1 KO vehicle (P=0.23).

DETAILED DESCRIPTION

The invention provides a therapeutic method for treating a nerve injury in a mammal where the injury may be caused by a traumatic or ischemic event. Such events include direct trauma such as head injuries, compression of nerves, blunt force trauma to the nerve cells and the like; ischemic events such as stroke, heart attack, hypoxia and the like. The method includes administration to a mammal in need of such therapy, of an effective amount of an $A_{2A}$ adenosine receptor modulating compound of formula I, or a pharmaceutically acceptable salt thereof to prevent damage to promote healing of the nerve cells.

The following definitions are used, unless otherwise described. Halo is fluoro, chloro, bromo, or iodo. Alkyl, alkenyl, alkynyl, alkoxy, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl includes a radical attached via a ring carbon of a monocyclic aromatic ring containing five or six ring atoms consisting of carbon and one to four heteroatoms each selected from non-peroxide oxygen, sulfur, and amine (—N(Y)—), wherein Y is absent or is hydrogen, O, $(C_1\text{-}C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The terms "a," "an," "the," "at least one," and "one or more" are used interchangeably. Thus, for example, a composition that comprises "an" element means one element or more than one element.

A condition or disorder is "alleviated" if the severity of a symptom of the condition or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A tissue "normally comprises" a cell if one or more of the cell are present in the tissue in an animal not afflicted with a disease, condition or disorder.

The word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "derivative" of a compound refers to a chemical compound that may be produced from another compound of similar structure in one or more steps, as in replacement of hydrogen by an alkyl, acyl, or amino group.

An "effective amount" means an amount sufficient to produce a selected or desired effect. For example, an effective amount of an $A_{2A}$ receptor antagonist is an amount that decreases the cell signaling activity of the $A_{2A}$ receptor.

The term "inhibit" refers to the ability of a disclosed compound to reduce of impede a described function. Preferably, inhibition is by at least 10%, more preferably by at least 25%, even more preferably by at least 50%, and most preferably, the function is inhibited by at least 75%.

A "therapeutically effective amount" of a compound is that amount of compound which is sufficient to provide a beneficial effect to the subject to which the compound is administered.

The term "treating" includes prophylaxis of the specific disease, disorder, or condition, or alleviation of the symptoms associated with a specific disease, disorder or condition or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

The term "parenteral" means not through the alimentary canal but by some other route such as subcutaneous, intramuscular, intrathecal, or intravenous.

The term "pharmaceutically acceptable carrier" includes any of the standard pharmaceutical carriers, such as a phosphate buffered saline solution, water and emulsions such as an oil/water or water/oil emulsion, and various types of wetting agents. The term also encompasses any of the agents approved by a regulatory agency of the U.S. Federal government or listed in the U.S. Pharmacopeia for use in animals, including humans.

The term "sample," refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

The term "modulator" refers to "$A_{2A}$ receptor agonists" or "$A_{2A}$ receptor antagonists". "$A_{2A}$ receptor agonists" are compounds that mimic the action of adenosine at the $A_{2A}$ receptors but may have differing potency or efficacy. "$A_{2A}$ receptor antagonists" are compounds that either 1) lack intrinsic agonist activity, 2) block agonist (e.g., adenosine) activation of adenosine receptor(s) or 3) both, often in a manner that is both fully surmountable and reversible ('competitive antagonist').

An $A_{2A}$ receptor agonist is "selective" if it has a preference for the $A_{2A}$ receptor over other adenosine receptor subtypes. Preferably the $A_{2A}$ receptor agonist will have an affinity preference for the $A_{2A}$ receptor greater than 3-fold, preferably greater than 10-fold and more preferably greater than 25-fold, than an affinity preference for other adenosine receptor types.

An $A_{2A}$ receptor antagonist is "selective" if it has a preference for the $A_{2A}$ receptor over other adenosine receptor subtypes. Preferably the $A_{2A}$ receptor antagonist will have an affinity preference for the $A_{2A}$ receptor greater than 3-fold, preferably greater than 10-fold and more preferably greater than 25-fold, than an affinity preference for other adenosine receptor types.

The term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also includes any of the agents approved by a regulatory agency of the US Federal government or listed in the US Pharmacopeia for use in animals, including humans.

The "term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

"Instructional material" includes a publication, a recording, a diagram, or any other medium of expression that can be used to communicate the usefulness of the disclosed compositions in the kit for effecting alleviation of the various diseases, disorders or conditions recited herein. Optionally, or alternately, the instructional material may describe one or more methods of alleviating the diseases or disorders in a cell or a tissue in a mammal. The instructional material of the kit may, for example, be affixed to a container that contains a disclosed compound or be shipped together with a container that contains the identified compound. Alternatively, the instructional material may be shipped separately from the container with the intention that the instructional material and the compound be used cooperatively by the recipient.

The method of the invention includes a kit comprising an inhibitor identified in the invention and an instructional material which describes administering the inhibitor or a composition comprising the inhibitor to a cell or an animal. This should be construed to include other embodiments of kits that are known to those skilled in the art, such as a kit comprising a (preferably sterile) solvent suitable for dissolving or suspending the composition of the invention prior to administering the compound to a cell or an animal. Preferably the animal is a human.

The disclosed compounds are generally named according to the IUPAC or CAS nomenclature system. Abbreviations that are well known to one of ordinary skill in the art may be used (e.g., "Ph" for phenyl, "Me" for methyl, "Et" for ethyl, "h" for hour or hours, "rt" for room temperature, and "rac" for racemic mixture).

The carbon atom content of various hydrocarbon-containing moieties is indicated by a prefix designating the minimum and maximum number of carbon atoms in the moiety, e.g., the prefix $C_i$-$C_j$ indicates a moiety of the integer "i" to the integer "j" carbon atoms, inclusive. Thus, for example, $(C_1-C_8)$alkyl refers to alkyl of one to eight carbon atoms, inclusive. The compounds herein are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. For example, "($C_1$-$C_{10}$)alkyl" refers to a branched or linear alkyl group having from one to ten carbons. Non-limiting examples include, but are not limited to, methyl, ethyl, n-propyl, iso-propyl, butyl, iso-butyl, sec-butyl, tert-butyl, pentyl, hexyl, heptyl, octyl and the like. The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl or trifluoromethyl and the like. The term "($C_2$-$C_6$)alkenyl", refers to an olefinically unsaturated branched or linear group having from two to six carbon atoms and at least one double bond. Typically, ($C_2$-$C_6$)alkenyl groups include, but are not limited to, 1-propenyl, 2-propenyl, 1,3-butadienyl, 1-butenyl, hexenyl, pentenyl, hexenyl, and the like. The term "aryl($C_1$-$C_8$)alkylene" includes benzyl, phenethyl, 3-phenylpropyl, naphthylmethyl and the like. The term ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like. The carbon atoms of the alkenyl or alkynyl groups that are not multiply bonded are considered alkyl carbon atoms for purposes of substitution or replacement. The term "($C_1$-$C_{10}$)alkoxy" refers to an alkyl group attached through an oxygen atom. Examples of ($C_1$-$C_{10}$)alkoxy can be methoxy, ethoxy, propoxy, isopropoxy, butoxy, iso-butoxy, sec-butoxy, pentoxy, 3-pentoxy, or hexyloxy and the like. The term "($C_3$-$C_8$)cycloalkyl", can be cyclopropyl, cyclobutyl, cyclopentyl, cyclohexyl, cycloheptyl, cyclooctyl and the like.

The term "($C_6$-$C_{10}$)aryl" denotes a phenyl radical or an ortho-fused bicyclic carbocyclic radical having about nine to ten ring atoms in which at least one ring is aromatic. Non-limiting examples of aryl groups include phenyl, naphthyl, tetrahydronaphthyl, indanyl, indenyl, and the like. "Optionally substituted aryl" includes aryl compounds having from zero to four substituents, and "substituted aryl" includes aryl compounds having one or more substituents. The term "($C_7$-$C_{16}$)arylalkyl" or "($C_7$-$C_{16}$)aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, and the like.

The term "optionally substituted aryl" includes aryl compounds having zero, one, two, three or four substituents, and a substituted aryl includes aryl compounds having one, two, three or four substituents, wherein the substituents include groups such as, for example, alkyl, halo, or amino substituents.

Heteroaryl denotes a radical of an optionally substituted mono- or bicyclic aromatic ring system containing five or six ring atoms consisting of carbon and 1, 2, 3, or 4 heteroatoms selected from non-peroxide oxygen, sulfur, and amine (—N(Y)—) wherein Y is absent or is hydrogen, O, ($C_1$-$C_8$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Non-limiting examples of heteroaryl include furyl, thienyl, pyridyl and the like.

The term "heterocycle" generally represents an optionally substituted mono- or bicyclic-carbocyclic ring system, having from 3 to about 10 ring atoms, which can be saturated or partially unsaturated, containing from one to three heteroatoms wherein the heteroatoms are selected from the group consisting of oxygen, sulfur, and nitrogen. Exemplary, "heterocycle" groups include monocyclic, bicyclic, or tricyclic groups containing one or more heteroatoms selected from oxygen, nitrogen, and sulfur. A "heterocycle" group also can include one or more oxo groups (=O) attached to a ring atom. Non-limiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "optionally substituted" refers to zero, one, two, three or four substituents, wherein the substituents are each independently selected. Each of the independently selected substituents may be the same or different than other substituents.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

is understood to represent a mixture of the structures:

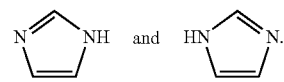

The present invention is also directed to pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art. For example, a pharmaceutical composition comprising a compound of the invention, or analog, derivative, or modification thereof, as described herein, is used to administer the appropriate compound to a subject.

Pharmaceutical compositions comprising the a compound of the invention are administered to a subject in need thereof by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means. The oral route is typically employed for most conditions requiring the compounds of the invention. Preference is given to intravenous injection or infusion for the acute treatments. For maintenance regimens, the oral or parenteral, e.g. intramuscular or subcutaneous, route is preferred.

Pharmaceutically acceptable carriers which are useful include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

In one embodiment the $A_{2A}$ adenosine receptor agonist can be administered 2-10 hours after an injury to the CNS, and the antagonist is administered beginning 1-2 days after CNS injury. In one embodiment the $A_{2A}$ adenosine receptor agonist can be administered 4-6 hours after an injury to the CNS, and the antagonist is administered beginning 1-2 days after CNS injury.

In one embodiment, agonists of $A_{2A}$ adenosine receptors include compounds having the formula (I):

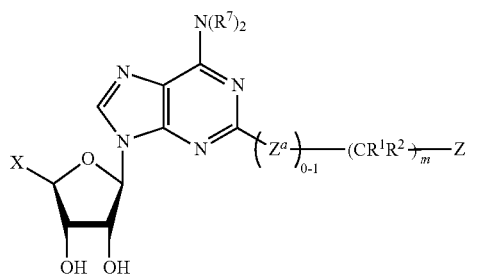

(I)

wherein $Z^a$ is —C≡C—, —O—, —NH—, or —NHN=$CR^{3a}$—;

Z is $CR^3R^4R^5$ or $NR^4R^5$;

each $R^1$ is independently hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, heterocycle, heterocycle($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N($R^b$)—, $R^bR^cNC$(=S)N($R^b$)—, $R^aOC$(=S)—, $R^aC$(=S)—, —$SSR^a$, $R^aS$(=O)—, $R^aS$(=O)$_2$—, or —N=$NR^b$;

each $R^2$ is independently hydrogen, halo, ($C_1$-$C_8$)alkyl, ($C_3$-$C_8$)cycloalkyl, heterocycle, heterocycle($C_1$-$C_8$)alkylene-, aryl, aryl($C_1$-$C_8$)alkylene-, heteroaryl, or heteroaryl($C_1$-$C_8$)alkylene-;

alternatively, $R^1$ and $R^2$ and the atom to which they are attached is C=O, C=S or C=$NR^d$;

$R^4$ and $R^5$ are independently H or ($C_1$-$C_8$)alkyl;

alternatively, $R^4$ and $R^5$ together with the atom to which they are attached form a saturated, partially unsaturated, or aromatic ring that is mono-, bi- or polycyclic and has 3, 4, 5, 6, 7, 8, 9, or 10 ring atoms optionally having 1, 2, 3, or 4 heteroatoms selected from oxy (—O—), S(O)$_{0-2}$, and amine in the ring.

wherein $R^4$ and $R^5$ are independently substituted with 0-3 $R^6$ groups; or any ring comprising $R^4$ and $R^5$ is substituted with from 0 to 14 $R^6$.

groups; wherein each $R^6$ is independently hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, ($C_6$-$C_{12}$)bicycloalkyl, heterocycle, heterocycle ($C_1$-$C_8$)alkylene-, aryl, aryl ($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N($R^b$)—, $R^bR^cNC$(=S)N($R^b$)—, $R^aOC$(=S)—, $R^aC$(=S)—, —$SSR^a$, $R^aS$(=O)—, —$NNR^b$, or two $R^6$ groups and the atom to which they are attached is C=O or C=S; or two $R^6$ groups together with the atom or atoms to which they are attached can form a carbocyclic or heterocyclic ring comprising from 1 to 6 carbon atoms and 1, 2, 3, or 4 heteroatoms selected from oxy (—O—), thio (—S—), sulfinyl (—SO—), sulfonyl (—S(O)$_2$—) and amine (—$NR^b$—) in the ring;

$R^3$ is hydrogen, halo, —$OR^a$, —$SR^a$, ($C_1$-$C_8$)alkyl, cyano, nitro, trifluoromethyl, trifluoromethoxy, ($C_3$-$C_8$)cycloalkyl, heterocycle, heterocycle($C_1$-$C_8$)alkylene-, aryl, aryl($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC$(=O)—, $R^aC$(=O)N($R^b$)—, $R^bR^cNC$(=O)N($R^b$)—, $R^bR^cNC$(=S)N($R^b$)—, $R^aOC$(=S)—, $R^aC$(=S)—, —$SSR^a$, $R^aS$(=O)—, $R^aS$(=O)$_2$—, —$NNR^b$; or if the ring formed from $CR^3R^4R^5$ is aryl or heteroaryl or partially unsaturated then $R^3$ can be absent;

$R^{3a}$ is hydrogen, ($C_1$-$C_8$)alkyl, or aryl;

each $R^7$ is independently hydrogen, ($C_1$-$C_8$)alkyl, ($C_3$-$C_8$)cycloalkyl, aryl, aryl($C_1$-$C_8$)alkylene, heteroaryl, or heteroaryl($C_1$-$C_8$)alkylene-;

X is —$CH_2OR^a$, —$CO_2R^a$, —$CH_2OC(O)R^a$, —$C(O)NR^bR^c$, —$CH_2SR^a$, —$C(S)OR^a$, —$CH_2OC(S)R^a$, —$C(S)NR^bR^c$, or —$CH_2N(R^b)(R^c)$;

alternatively, X is an aromatic ring of the formula:

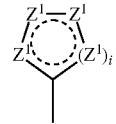

each $Z^1$ is non-peroxide oxy (—O—), S(O)$_{0-2}$, —C($R^8$)—, or amine (—$NR^8$—), provided that at least one $Z^1$ is non-peroxide oxy (—O—), thio (—S—), sulfinyl (—SO—), sulfonyl (—S(O)$_2$—) or amine (—$NR^8$—);

each $R^8$ is independently hydrogen, ($C_1$-$C_8$)alkyl, ($C_1$-$C_8$)alkenyl, ($C_3$-$C_8$)cycloalkyl, ($C_3$-$C_8$)cycloalkyl($C_1$-$C_8$)alkylene, ($C_3$-$C_8$)cycloalkenyl, ($C_3$-$C_8$)cycloalkenyl($C_1$-$C_8$)alkylene, aryl, aryl($C_1$-$C_8$)alkylene, heteroaryl, or heteroaryl($C_1$-$C_8$)alkylene, wherein any of the alkyl or alkenyl groups of $R^8$ are optionally interrupted by —O—, —S—, or —N($R^a$)—;

wherein any of the alkyl, cycloalkyl, heterocycle, aryl, or heteroaryl, groups of $R^1$, $R^2$, $R^3$, $R^{3a}$, $R^6$, $R^7$, and $R^8$ is optionally substituted on carbon with one or more (e.g. 1, 2, 3, or 4) substituents, where the substituents are halo, —$OR^a$, —$SR^a$, ($C_1$-$C_8$)alkyl, cyano, nitro, trifluoromethyl, trifluoromethoxy, ($C_3$-$C_8$)cycloalkyl, ($C_6$-$C_{12}$)bicycloalkyl, heterocycle, heterocycle($C_1$-$C_8$)alkylene-, aryl, aryloxy, aryl($C_1$-$C_8$)alkylene-, heteroaryl, heteroaryl($C_1$-$C_8$)alkylene-, —$CO_2R^a$, $R^aC$(=O)O—, $R^aC$(=O)—, —$OCO_2R^a$, $R^bR^cNC$(=O)O—, $R^aOC$(=O)N($R^b$)—, $R^bR^cN$—, $R^bR^cNC(=O)—$, $R^aC(=O)N(R^b)—$, $R^bR^cNC(=O)N(R^b)—$, $R^bR^cNC(=S)N(R^b)—$, $R^aOC(=S)—$, $R^aC(=S)—$, $—SSR^a$, $R^aS(=O)_p—$, $R^bR^cNS(O)_p—$, or $—N=NR^b$;

wherein any $(C_1-C_8)$alkyl, $(C_3-C_8)$cycloalkyl, $(C_6-C_{12})$bicycloalkyl, $(C_1-C_8)$alkoxy, $(C_1-C_8)$alkanoyl, $(C_1-C_8)$alkylene, or heterocycle, is optionally partially unsaturated;

each $R^a$, $R^b$, and $R^c$ is independently hydrogen, $(C_1-C_{12})$alkyl, $(C_1-C_8)$alkoxy-$(C_1-C_8)$alkyl-, $(C_3-C_8)$cycloalkyl, $(C_1-C_8)$alkylthio-$(C_1-C_8)$alkyl-, amino acid, aryl, aryl$(C_1-C_8)$alkylene, heteroaryl, or heteroaryl$(C_1-C_8)$alkylene;

alternatively $R^b$ and $R^c$, together with the nitrogen to which they are attached, form a pyrrolidino, piperidino, morpholino, or thiomorpholino ring;

$R^d$ is hydrogen or $(C_1-C_6)$alkyl; i is 1 or 2; m is 0 to 8; and p is 0 to 2; or a pharmaceutically acceptable salt thereof.

Additional exemplary compounds having formula (I) include compounds having the formula (Ia):

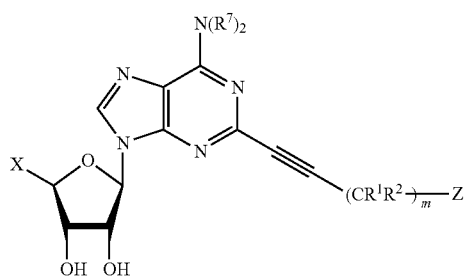

(Ia)

wherein $R^1$ is hydrogen, —OH, —CH$_2$OH, —OMe, —OAc, —NH$_2$, —NHMe, —NMe$_2$ or —NHAc;

$R^2$ is hydrogen, $(C_1-C_8)$alkyl, cyclopropyl, cyclohexyl or benzyl;

Z is $CR^3R^4R^5$ or $NR^4R^5$;

$R^3$ is hydrogen, OH, OMe, OAc, NH$_2$, NHMe, NMe$_2$ or NHAc;

$CR^3R^4R^5$ or $NR^4R^5$ is cyclopentane, cyclohexane, piperidine, dihydro-pyridine, tetrahydro-pyridine, pyridine, piperazine, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, or pyrazolidine; and is optionally substituted with 0-2 $R^6$ groups;

alternatively, the ring $CR^3R^4R^5$ or $NR^4R^5$ is:

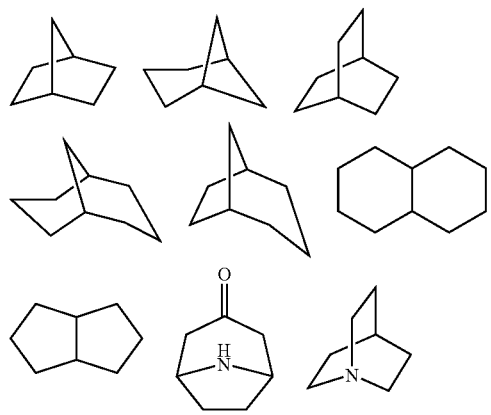

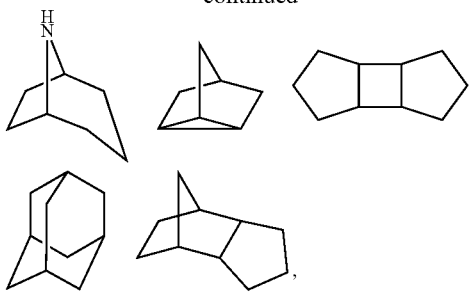

and is optionally substituted with 0-2 $R^6$ groups; where $R^6$ is hydrogen, $(C_1-C_8)$alkyl, —OR$^a$, —CO$_2$R$^a$, $R^aC(=O)—$, $R^aC(=O)O—$, $R^bR^cN—$, $R^bR^cNC(=O)—$, or aryl;

$R^a$ and $R^b$ are independently hydrogen, $(C_3-C_4)$-cycloalkyl, $(C_1-C_8)$alkyl, aryl or aryl$(C_1-C_8)$alkylene;

$R^7$ is hydrogen, $(C_1-C_8)$alkyl, aryl, aryl$(C_1-C_8)$alkylene, or heteroaryl$(C_1-C_8)$alkylene;

$R^8$ is methyl, ethyl, propyl, 2-propenyl, cyclopropyl, cyclobutyl, cyclopropylmethyl, —(CH$_2$)$_2$CO$_2$CH$_3$, or —(CH$_2$)$_{2-3}$OH;

X is —CH$_2$OR$^a$, —CO$_2$R$^a$, —CH$_2$OC(O)R$^a$, or —C(O)NR$^b$R$^c$;

alternatively, X is:

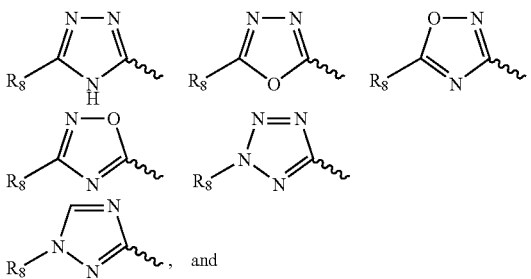

, and m is 0, 1, or 2; or a pharmaceutically acceptable salt thereof.

Additional exemplary compounds having formula (I) include compounds having the formula (Ia), wherein:

$R^1$ is hydrogen, OH, OMe, or NH$_2$;

$R^2$ is hydrogen, methyl, ethyl or propyl;

the ring $CR^3R^4R^5$ or $NR^4R^5$ is:

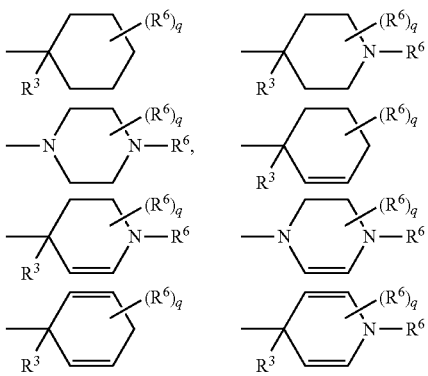

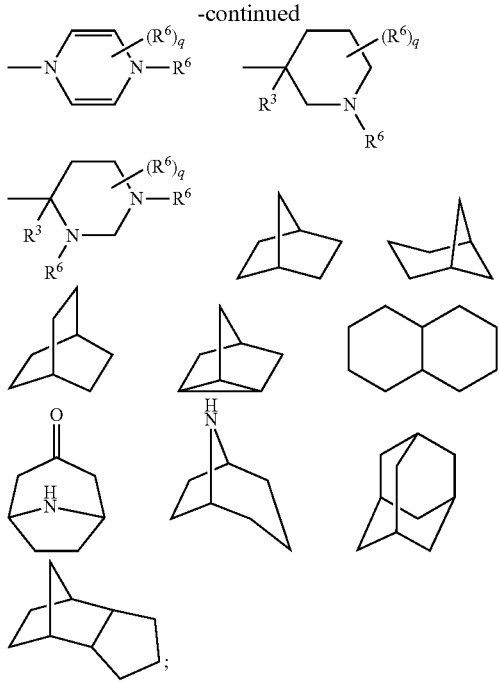

$R^3$ is hydrogen, OH, OMe, or $NH_2$;

q is 0, 1, or 2;

$R^6$ is hydrogen, $(C_1-C_8)$alkyl, $-OR^a$, $-CO_2R^a$, $R^aC(=O)-$, $R^aC(=O)O-$, $R^bR^cN-$, $R^bR^cNC(=O)-$, or aryl;

$R^a$ and $R^b$ are independently hydrogen, methyl, ethyl, propyl, butyl, ethylhexyl, cyclopropyl, cyclobutyl, phenyl or benzyl;

$N(R^7)_2$ is amino, methylamino, dimethylamino; ethylamino; pentylamino, diphenylethylamino, (pyridinylmethyl)amino, (pyridinyl)(methyl)amino, diethylamino or benzylamino; and, $R^8$ is methyl, ethyl, propyl, or cyclopropyl;

X is $-CH_2OR^a$ or $-C(O)NR^bR^c$;

alternatively, X is:

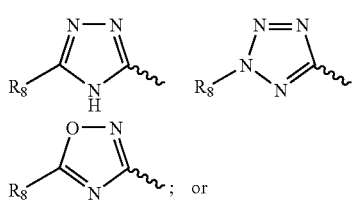

a pharmaceutically acceptable salt thereof.

Additional exemplary values include compounds having the formula (Ia), wherein:

$R^1$ is hydrogen, OH, or $NH_2$; $R^2$ is hydrogen or methyl; $R^3$ is hydrogen, OH, or $NH_2$; the ring $CR^3R^4R^5$ or $NR^4R^5$ is:

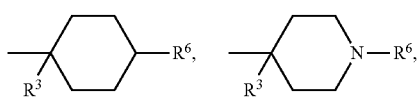

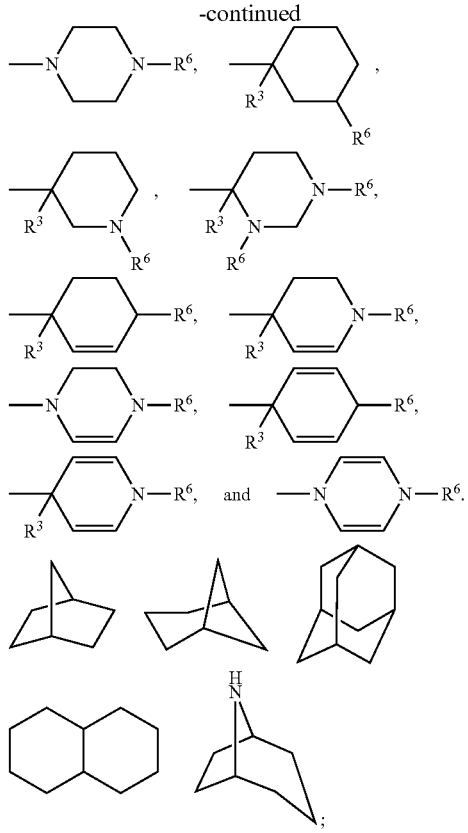

$R^6$ is hydrogen, methyl, ethyl, t-butyl, phenyl, $-CO_2R^a-$ $CONR^bR^c$, or $R^aC(=O)-$; $R^b$ is H; $R^a$ is methyl, ethyl, propyl, butyl, pentyl, ethylhexyl cyclopropyl, or cyclobutyl; $-N(R^7)_2$ is amino, methylamino, dimethylamino, ethylamino, diethylamino or benzylamino; or a pharmaceutically acceptable salt thereof.

Additional exemplary values include compounds having the formula (Ia), wherein $R^1$ is hydrogen or OH; $R^2$ is hydrogen; $R^3$ is hydrogen or OH; the ring $CR^3R^4R^5$ or $NR^4R^5$ is:

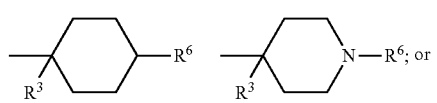

$R^6$ is hydrogen, methyl, ethyl, $-CO_2R^a$, or $-CONR^bR^c$; $R^b$ is H; $R^a$ is methyl, ethyl, iso-propyl, iso-butyl, tert-butyl, or cyclopropyl;

$N(R^7)_2$ is amino, or methylamino;

X is $-CH_2OH$,

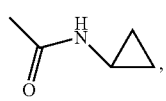

$-C(O)NHCH_3$, or $-C(O)NHCH_2CH_3$; or a pharmaceutically acceptable salt thereof.

Additional exemplary compounds having formula (I) include compounds wherein the ring comprising $R^4$ and $R^5$ is 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-carboxylic acid tert-butyl ester, tert-butylester, 1-piperidine-4-carboxylic acid methyl ester, or 1-piperidine-4-carboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, or 1-piperidine-3-carboxylic acid tert-butyl ester; or a pharmaceutically acceptable salt thereof.

Additional exemplary compounds include compounds 1-33 in Table 1 or pharmaceutically acceptable salts thereof:

TABLE 1

| Compound # | $R^c$ | $R^7$ | —(CHR$^1$)$_m$—Z |
|---|---|---|---|
| 1 | Et | H | 4-(methoxycarbonyl)cyclohexyl-CH$_2$-* |
| 2 | cPr | H | 4-(methoxycarbonyl)piperidin-1-yl-CH$_2$-* |
| 3 | Et | H | 4-(methoxycarbonyl)piperidin-1-yl-CH$_2$-* |
| 4 | Et | H | 4-(ethoxycarbonyl)piperidin-1-yl-CH$_2$-* |
| 5 | Et | H | 4-(isobutoxycarbonyl)piperidin-1-yl-CH$_2$-* |
| 6 (JR-3213) | Et | H | 4-(ethoxycarbonyl)piperazin-1-yl-CH$_2$-* |
| 7 | Et | H | 4-(isobutoxycarbonyl)piperazin-1-yl-CH$_2$-* |
| 8 | Et | H | 4-((methoxycarbonyloxy)methyl)cyclohexyl-CH$_2$-* |
| 9 | Et | H | 4-(tert-butoxycarbonyl)piperidin-1-yl-CH$_2$-* |
| 10 | Et | H | 4-(neopentyloxycarbonyl)piperidin-1-yl-CH$_2$-* |
| 11 | cPr | H | 4-(neopentyloxycarbonyl)piperidin-1-yl-CH$_2$-* |

TABLE 1-continued
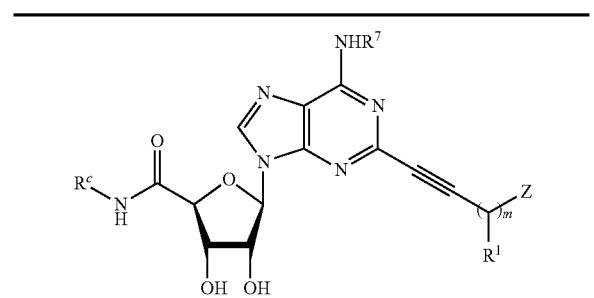
| Compound # | R^c | R^7 | —(CHR^1)_m—Z |
|---|---|---|---|
| 12 | Et | H | 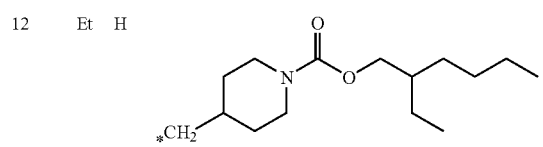 |
| 13 | cPr | H | 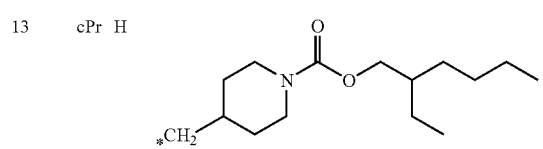 |
| 14 | Et | H | 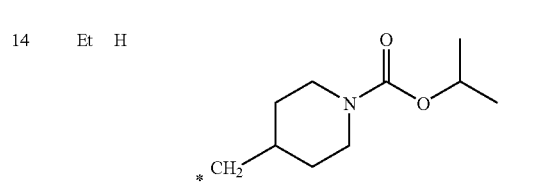 |
| 15 | cPr | H | 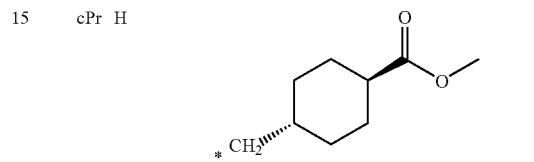 |
| 16 | Et | H | 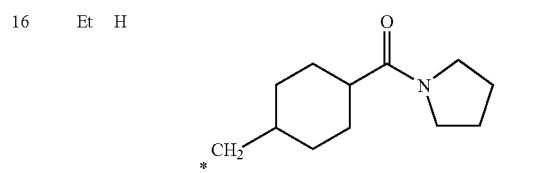 |
| 17 | Et | H | 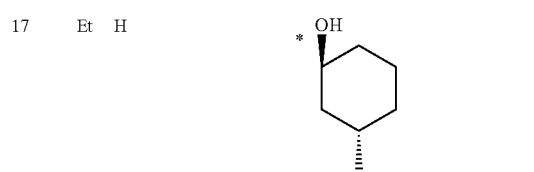 |
| 18 | Et | H | 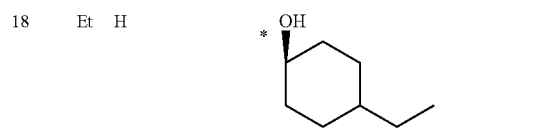 |
TABLE 1-continued
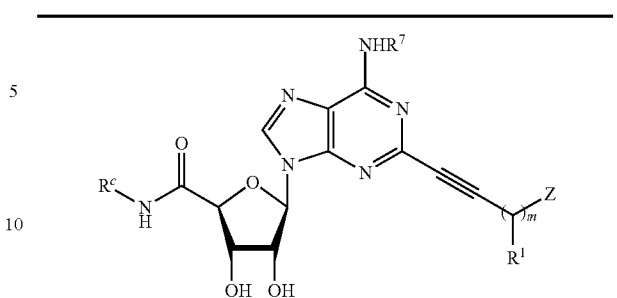
| Compound # | R^c | R^7 | —(CHR^1)_m—Z |
|---|---|---|---|
| 19 | Et | H | 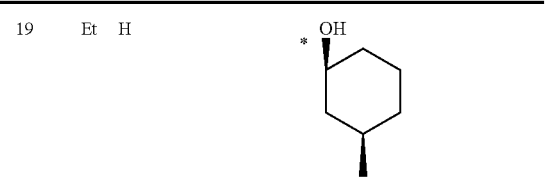 |
| 20 | Et | H |  |
| 21 | Et | H | 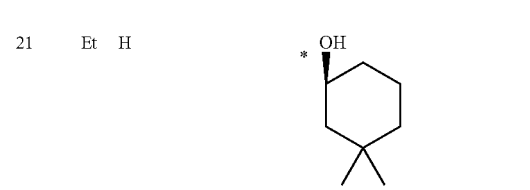 |
| 22 | cPr | H | 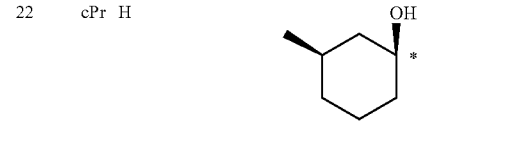 |
| 23 | Et | H | 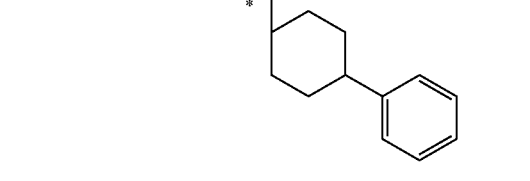 |
| 24 | Et | H |  |
| 25 | cPr | H |  |

TABLE 1-continued

[Structure: adenine-ribose with NHR⁷, alkyne-(CHR¹)ₘ-Z substituent, R^c-C(O)NH- on ribose]

| Compound # | R^c | R⁷ | —(CHR¹)ₘ—Z |
|---|---|---|---|
| 26 | cPr | H | (bornyl-OH group) |
| 27 | Et | H | (2-hydroxyadamantyl) |
| 28 | cPr | H | (2-hydroxyadamantyl) |
| 29 | Et | H | (2-methyl-2-hydroxydecahydronaphthalenyl, *CH₂) |
| 30 | cPr | H | *CH₂-(4-piperidinyl)-C(O)O-phenyl |
| 31 | Et | H | *CH₂-(4-piperidinyl)-C(O)O-phenyl |
| 32 | cPr | H | *CH₂-(4-piperidinyl)-C(O)O-CH₂-phenyl |
| 33 | Et | H | *CH₂-(4-piperidinyl)-C(O)O-CH₂-phenyl |

* signifies the point of attachment.

Additional exemplary values include compounds having the formula (Ib), (Ic), (Id) or a pharmaceutically acceptable salt thereof:

(Ib)

(Ic)

(Id)

A group of exemplary compounds having formula (I) include those wherein each R⁷ is hydrogen, X is ethylaminocarbonyl, R¹ and R² are each hydrogen, and Z is a 4-piperidyl-1-carboxylic acid or ester group, wherein $R^a$ is methyl, ethyl, propyl, isopropyl, isobutyl, or t-butyl, 4.

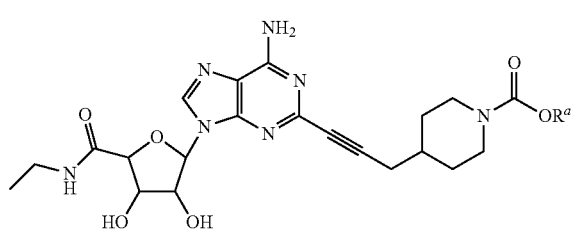

4a, $R^a$ is H
4b, $R^a$ is CH$_3$ $A_{2A}$ adenosine receptor agonists include those described in U.S. Pat. No. 6,232,297 and in U.S. published Patent Application Nos. 2003/0186926 A1, 2006/0040888 A1, 2006/0040889 A1 and 2006/0100169 A1. Exemplary compounds include those wherein each $R^7$ is hydrogen, X is ethylaminocarbonyl and Z is 4-carboxycyclohexylmethyl (DWH-146a), Z is 4-methoxycarbonylcyclohexylmethyl (DWH-146e), Z is 4-isopropylcarbonyl-cyclohexylmethyl (AB-1), Z is 4-acetoxymethyl-cyclohexylmethyl (JMR-193) or Z is 4-pyrrolidine-1-carbonylcyclohexylmethyl (AB-3).

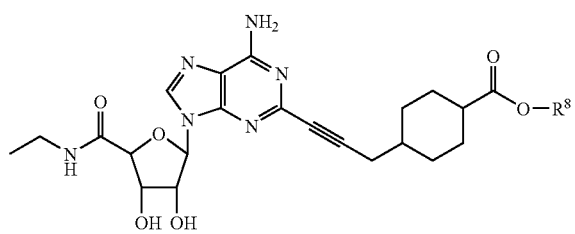

5 ATL-146: $R^8$ = H (ALT-146a) or Me(ATL-146e).
AB-1: $R^8$ = iPr, and

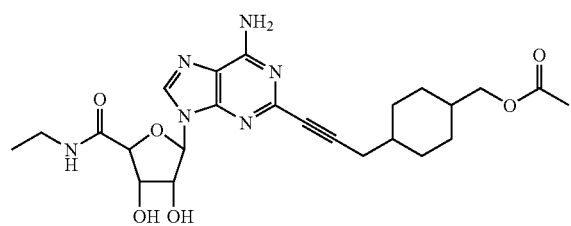

JMR-193 (ATL-193)

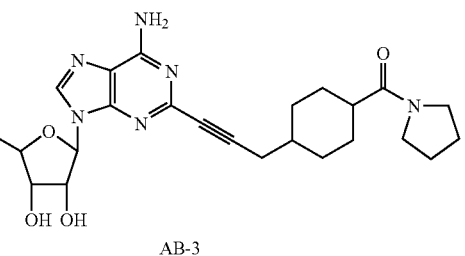

AB-3

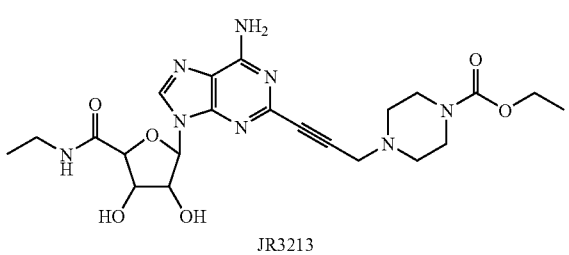

JR3213

Additional exemplary compounds having formula (I) include compounds having formula (Ie):

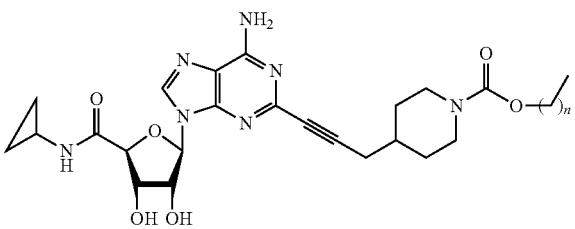

(Ie)

In formula (Ie) n is 0, 1, 2, 3, 4, 5, 6, 7, 8, 9, 10, 11, 12, 13, 14, 15, 16, 17, or 18. Another group of exemplary compounds n is, 5, 6, 7, 8, 9, 10, 11, 12, 13, 14, 15, 16, 17, or 18.

Additional exemplary compounds having formula (I) include compounds having formula (If):

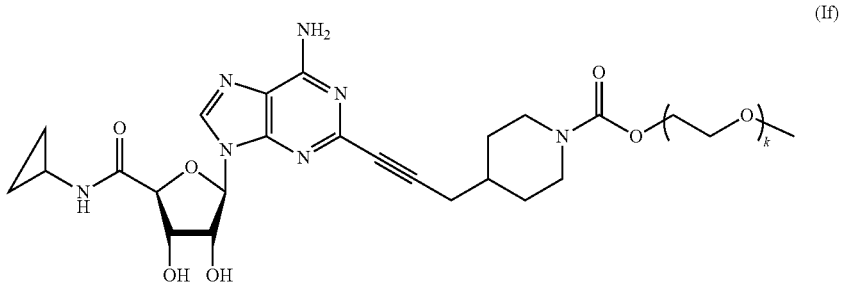

(If)

In formula (If) k is 1, 2, 3, 4, 5, 6, 7, 8, 9, 10, 11, 12, 13, 14, 15, 16, 17, or 18.
Additional exemplary compounds having formula (I) include compounds having formula (Ig):
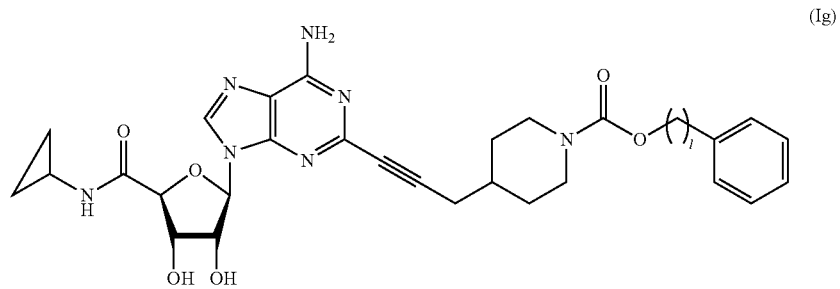
(Ig)
In formula (Ig) l is 0, 1, 2, 3, or 4.
Additional exemplary compounds having formula (I) include compounds having the formulas:
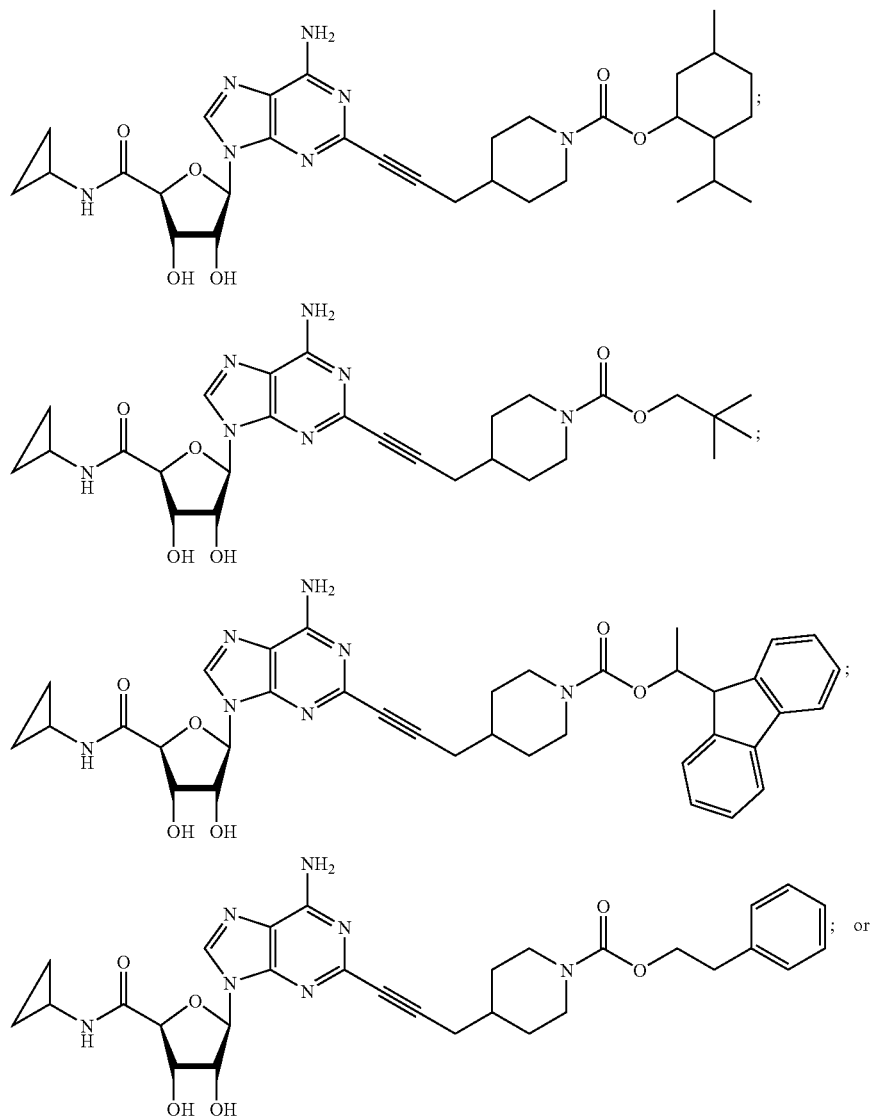

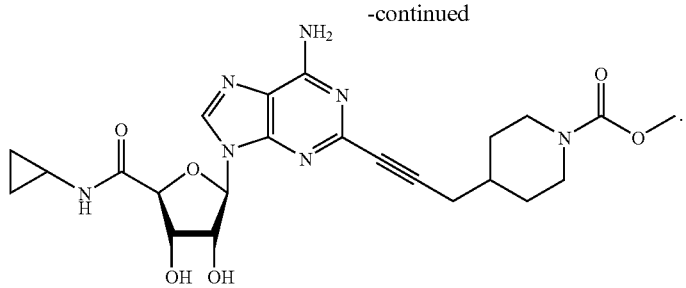

The structures of three novel high affinity $A_{2A}R$ agonists.

TABLE 2

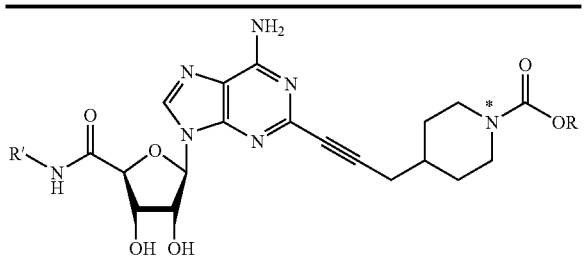

| Compound | R Group | R' Group |
|---|---|---|
| ATL202 | —CH$_3$ | —CH$_2$CH$_3$ |
| ATL210 | —CH$_2$CH(CH$_3$)CH$_3$ | —CH$_2$CH$_3$ |
| ATL313 | —CH$_3$ | —CH(CH$_2$)(CH$_2$) |

Additional examples of useful compounds are illustrated in Tables 3, 4, and 5, below:

TABLE 3

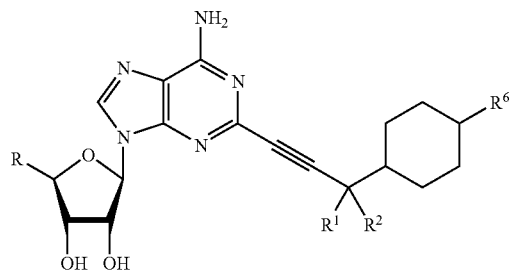

| Compound | R | R$^1$ | R$^2$ | R$^6$ |
|---|---|---|---|---|
| ATL2037 | NECA | H | H | CH$_2$OH |
| MP9056 | NECA | OH | H | CH$_2$OH |
| ATL146a | NECA | H | H | CO$_2$H |
| MP9057 | NECA | OH | H | CO$_2$H |
| ATL146e | NECA | H | H | CO$_2$Me |
| MP9058 | NECA | OH | H | CO$_2$Me |
| JR2145 | CH$_2$OH | H | H | CO$_2$Me |
| MP9059 | CH$_2$OH | OH | H | CO$_2$Me |
| ATL193 | NECA | H | H | CH$_2$OAc |
| MP9060 | NECA | OH | H | CH$_2$Oac |
| JR2147 | CH$_2$OH | H | H | CH$_2$Oac |
| MP9061 | CH$_2$OH | OH | H | CH$_2$Oac |
| JR3023 | NECA | H | H | CH$_2$N(CH$_3$)$_2$ |
| MP9062 | NECA | OH | H | CH$_2$N(CH$_3$)$_2$ |
| JR3021 | NECA | H | H | COOCH$_2$CH$_2$NHBoc |
| MP9063 | NECA | OH | H | COOCH$_2$CH$_2$NHBoc |
| JR3033 | NECA | H | H | COOCH$_2$CH$_2$NH$_2$ |
| MP9064 | NECA | OH | H | COOCH$_2$CH$_2$NH$_2$ |
| JR3037 | NECA | H | H | CONHCH$_2$CH$_3$ |
| MP9065 | NECA | OH | H | CONHCH$_2$CH$_3$ |

TABLE 3-continued

| Compound | R | R$^1$ | R$^2$ | R$^6$ |
|---|---|---|---|---|
| JR3055 | NECA | H | H | CONH$_2$ |
| MP9072 | NECA | OH | H | CONH$_2$ |
| JR3065 | NECA | H | H | CONHMe |
| MP9066 | NECA | OH | H | CONHMe |
| JR3067B | NECA | H | H | Me, cis CO$_2$Me |
| MP9067 | NECA | OH | H | Me, cis CO$_2$Me |
| JR3067A | NECA | H | H | Me, trans CO$_2$Me |
| MP9068 | NECA | OH | H | Me, trans CO$_2$Me |
| JR3087 | NECA | H | H | CH$_2$CH$_3$ |
| MP9069 | NECA | OH | H | CH$_2$CH$_3$ |
| JR3159A | NECA | H | H | H |
| JR3159B | NECA | OH | H | H |
| JR3119 | NECA | H | H | COCH$_3$ |
| MP9070 | NECA | OH | H | COCH$_3$ |
| JR3121 | NECA | H | H | CHCH$_3$(OH) |
| MP9071 | NECA | OH | H | CHCH$_3$(OH) |
| JR3139 | NECA | OH | C$_6$H$_{11}$ | H |

NECA = CH$_3$CH$_2$N(H)C(O)—

TABLE 4

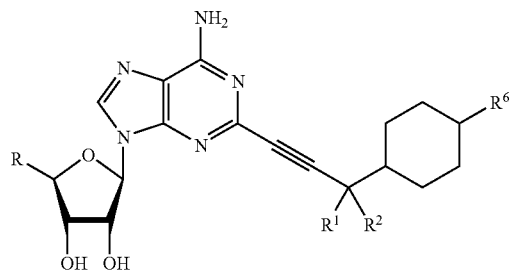

(Note: structure shown with ethyl amide and piperidine N-R$^6$)

| Compound | R$^1$ | R$^2$ | R$^6$ |
|---|---|---|---|
| JR3261 | H | H | H |
| JR3259 | H | H | CO$_2$tBu |
| JR3269 | H | H | CO$_2$Et |
| JR4011 | H | H | CO$_2$iBu |
| JR4009 | H | H | CO$_2$iPr |
| JR4007 | H | H | COMe |
| JR4051 | H | H | COC(CH$_3$)$_3$ |
| JR4047 | H | H | COCH$_2$(CH$_3$)$_3$ |
| MP9047 | H | H | COCH$_3$ |

TABLE 4-continued

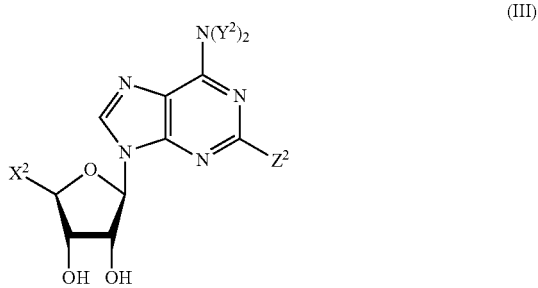

| Compound | $R^1$ | $R^2$ | $R^6$ |
|---|---|---|---|
| MP9048 | H | H | $C(O)N(CH_3)_2$ |
| MP9049 | H | H | $C(O)N(CH_3)Et$ |
| MP9050 | H | H | $C(O)N(CH_3)iPr$ |
| MP9051 | H | H | $C(O)N(CH_3)iBu$ |
| MP9052 | H | H | $C(O)NH(CH_3)$ |
| MP9053 | H | H | $C(O)NH(Et)$ |
| MP9054 | H | H | $C(O)NH(iPr)$ |
| MP9055 | H | H | $C(O)NH(iBu)$ |
| TX3261 | OH | H | H |
| TX3259 | OH | H | $CO_2tBu$ |
| TX3269 | OH | H | $CO_2Et$ |
| TX4011 | OH | H | $CO_2iBu$ |
| TX4009 | OH | H | $CO_2iPr$ |
| TX4007 | OH | H | COMe |
| TX4051 | OH | H | $COC(CH_3)_3$ |
| TX4047 | OH | H | $COCH_2(CH_3)_3$ |
| TX9047 | OH | H | $COCH_3$ |
| TX9048 | OH | H | $C(O)N(CH_3)_2$ |
| TX9049 | OH | H | $C(O)N(CH_3)Et$ |
| TX9050 | OH | H | $C(O)N(CH_3)iPr$ |
| TX9051 | OH | H | $C(O)N(CH_3)iBu$ |
| TX9052 | OH | H | $C(O)NH(CH_3)$ |
| TX9053 | OH | H | $C(O)NH(Et)$ |
| TX9054 | OH | H | $C(O)NH(iPr)$ |
| TX9055 | OH | H | $C(O)NH(iBu)$ |

TABLE 5

| Compound | N | $R^3$ | $R^6$ |
|---|---|---|---|
| JR3135 | 1 | OH | H |
| JR3089 | 2 | OH | H |
| JR3205 | 2 | $NH_2$ | H |
| JR3177A | 2 | OH | $2-CH_3$ |
| JR3177B | 2 | OH | $2-CH_3$ |
| JR3181A | 2 | OH | $2-CH_3$ |
| JR3181B | 2 | OH | $2-CH_3$ |
| JR3227 | 2 | OH | $2-C(CH_3)_3$ |
| JR9876 | 2 | OH | $2-C_6H_5$ |
| JR3179 | 2 | OH | $3-CH_3$ |
| JR3221 | 2 | OH (R) | $3-CH_3$ (R) |
| ATL 203 | 2 | OH (S) | $3-CH_3$ (R) |
| MP9041 | 2 | OH (R) | $3-CH_3$ (S) |
| MP9042 | 2 | OH (S) | $3-CH_3$ (S) |
| JR3201B | 2 | OH | $3-(CH_3)_2$ |
| MP9043 | 2 | OH (R) | $3-CH_2CH_3$ (R) |
| MP9044 | 2 | OH (S) | $3-CH_2CH_3$ (R) |
| MP9045 | 2 | OH (R) | $3-CH_2CH_3$ (S) |
| MP9046 | 2 | OH (S) | $3-CH_2CH_3$ (S) |

TABLE 5-continued

| Compound | N | $R^3$ | $R^6$ |
|---|---|---|---|
| JR3163 | 2 | OH | $3-(CH_3)_2, 5-(CH_3)_2$ |
| JR9875 | 2 | OH | $4-CH_3$ |
| JR3149 | 2 | OH | $4-C_2H_5$ |
| JR3203 | 2 | OH | $4-C(CH_3)_3$ |
| JR3161 | 2 | OH | $4-C_6H_5$ |

Another exemplary group of agonists of $A_{2A}$ adenosine receptors include compounds having general formula (III):

(III)

wherein $Z^2$ is a $—OR^{12}$, $—NR^{13}R^{14}$, a $—C≡C-Z^3$, or $—NH—N=R^{17}$;

each $Y^2$ is individually hydrogen, $C_1$-$C_6$ alkyl, $C_3$-$C_7$ cycloalkyl, phenyl or phenyl $C_1$-$C_3$ alkyl;

$R^{12}$ is $C_{1-4}$-alkyl; $C_{1-4}$-alkyl substituted with one or more $C_{1-4}$-alkoxy groups, halogens (fluorine, chlorine or bromine), hydroxy groups, amino groups, mono($C_{1-4}$-alkyl)amino groups, di($C_{1-4}$-alkyl)amino groups or $C_{6-10}$-aryl groups wherein the aryl groups may be substituted with one or more halogens (fluorine, chlorine or bromine), $C_{1-4}$-alkyl groups, hydroxy groups, amino groups, mono($C_{1-4}$-alkyl)amino groups, di($C_{1-4}$-alkyl)amino groups), $C_{6-10}$-aryl, or $C_{6-10}$-aryl substituted with one or more halogens (fluorine, chlorine or bromine), hydroxy groups, amino groups, mono($C_{1-4}$-alkyl)amino groups, di($C_{1-4}$-alkyl)amino groups or $C_{1-4}$-alkyl groups;

one of $R^{13}$ and $R^{14}$ has the same meaning as $R^{12}$ and the other is hydrogen; and $R^{17}$ is a group having the formula (i)

(i)

wherein each of $R^{15}$ and $R^{16}$ independently may be hydrogen, ($C_3$-$C_7$)cycloalkyl or any of the meanings of $R^{12}$, provided that $R^{15}$ and $R^{16}$ are not both hydrogen;

$X^2$ is $CH_2OH$, $CH_3$, $CO_2R^{20}$ or $C(=O)NR^{21}R^{22}$ wherein $R^{20}$ has the same meaning as $R^{13}$ and wherein $R^{21}$ and $R^{22}$ have the same meanings as $R^{15}$ and $R^{16}$ or $R^{21}$ and $R^{22}$ are both H;

$Z^3$ has one of the following meanings:

$C_6$-$C_{10}$ aryl, optionally substituted with one to three halogen atoms, $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino $C_1$-$C_3$ monoalkylamino, $C_2$-$C_6$ dialkylamino, methylenedioxy or aminocarbonyl; a group of formula —$(CH_2)_q$-Het wherein q is 0 or an integer from 1 to 3 and Het is 5 or 6 membered heterocyclic aromatic or non-aromatic ring, optionally benzocondensed, containing 1 to 3 heteroatoms selected from non-peroxide oxygen, nitrogen and sulphur, linked through a carbon atom or through a nitrogen atom; $C_3$-$C_7$ cycloalkyl optionally containing unsaturation or $C_2$-$C_4$ alkenyl;

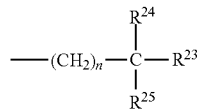
(ii)

wherein $R^{23}$ is hydrogen, methyl or phenyl;

$R^{24}$ is hydrogen, $C_1$-$C_6$ linear or branched alkyl, $C_5$-$C_6$ cycloalkyl or $C_3$-$C_7$ cycloalkenyl, phenyl-$C_1$-$C_2$-alkyl or $R^{23}$ and $R^{24}$, taken together, form a 5- or 6-membered carbocyclic ring or $R^{25}$ is hydrogen and $R^{23}$ and $R^{24}$, taken together, form an oxo group or a corresponding acetalic derivative;

$R^{25}$ is OH, $NH_2$ dialkylamino, halogen, cyano; $C_1$-$C_{16}$ alkyl, optionally comprising 1-2 double bonds, O, S or $NY^2$; where n is 0, 1, 2, 3, or 4; or a pharmaceutically acceptable salt thereof.

Preferably, in the compound of formula (III), $Z^2$ is a group of the formula (iii)

—O—$(CH_2)_n$—Ar (iii)

wherein n is an integer from 1-4, preferably 2, and Ar is a phenyl group, tolyl group, naphthyl group, xylyl group or mesityl group. Most preferably Ar is a para-tolyl group and n=2.

Preferably, in the compound of formula (III), $Z^2$ is a group of the formula (iv)

—NH—N=CHCy (iv)

wherein Cy is a $C_{3-7}$-cycloalkyl group, preferably cyclohexyl or a $C_{1-4}$ alkyl group, preferably isopropyl.

Preferably, in the compound of formula (III), $Z^2$ is a group of the formula (vii)

—C≡C-$Z^3$ (v)

wherein $Z^3$ is $C_3$-$C_{16}$ alkyl, hydroxy $C_2$-$C_6$ alkyl or (phenyl) (hydroxymethyl).

exemplary examples of compounds having formula (III) include those shown below:

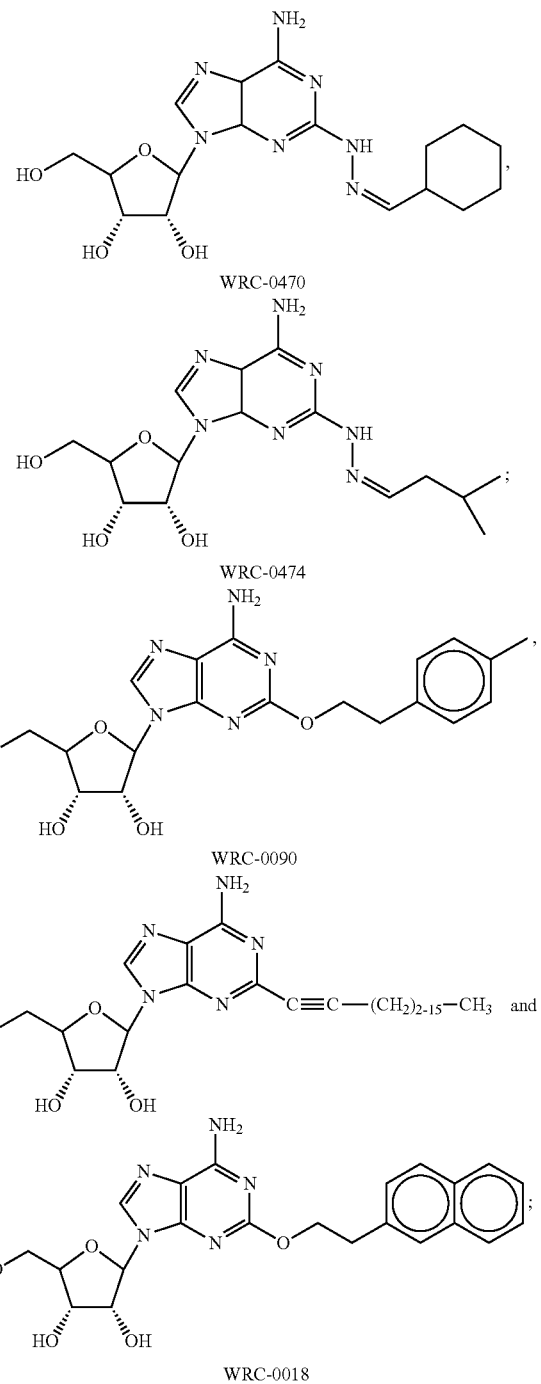

wherein the H on $CH_2OH$ can optionally be replaced by ethylaminocarbonyl and where WRC-0474[SHA 211] and WRC-0470 are particularly preferred.

Such compounds may be synthesized as described in: Olsson et al. (U.S. Pat. Nos. 5,140,015 and 5,278,150); Cristalli (U.S. Pat. No. 5,593,975); Miyasaka et al. (U.S. Pat. No. 4,956,345); Hutchinson, A. J. et al., *J. Pharmacol. Exp. Ther.*, 251, 47 (1989); Olsson, R. A. et al., *J. Med. Chem.*, 29, 1683 (1986); Bridges, A. J. et al., *J. Med. Chem.*, 31, 1282 (1988); Hutchinson, A. J. et al., *J. Med. Chem.*, 33, 1919 (1990); Ukeeda, M. et al., *J. Med. Chem.*, 34, 1334 (1991); Francis, J. E. et al., *J. Med. Chem.*, 34, 2570 (1991); Yoneyama, F. et al., Eur. J. Pharmacol., 213, 199-204 (1992); Peet, N. P. et al., J. Med. Chem., 35, 3263 (1992); and Cristalli, G. et al., J. Med. Chem., 35, 2363 (1992).

Another embodiment includes compounds having formula (III) where $Z^2$ is a group having formula (vi):

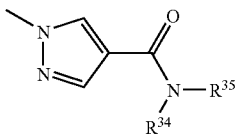

(vi)

wherein $R^{34}$ and $R^{35}$ are independently hydrogen, $C_1$-$C_6$ alkyl, $C_3$-$C_7$ cycloalkyl, phenyl, phenyl $C_1$-$C_3$ alkyl or $R^{34}$ and $R^{35}$ taken together with the nitrogen atom are a 5- or 6-membered heterocyclic ring containing 1-2 heteroatoms selected from non-peroxide oxygen, nitrogen (—N($R^{13}$)—) and sulphur atoms. Preferably one of $R^{34}$ and $R^{35}$ is hydrogen and the other is ethyl, methyl or propyl. More preferably one of $R^{34}$ and $R^{35}$ is hydrogen and the other is ethyl or methyl.

The 2-(pyrazol-1-yl)adenosine compounds, wherein $Z^2$ is a group having formula (vi), can be prepared by reacting a 2-chloro- or 2-iodo adenosine derivative with an 1H-pyrazole-4-carboxamides compound having formula (vii):

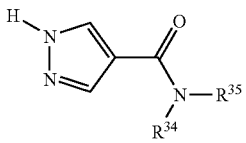

(vii)

where $R^{34}$ and $R^{35}$ are as described above, wherein selective protection/deprotection of the amido group is used as needed. An exemplary pyrazole is a compound having the formula:

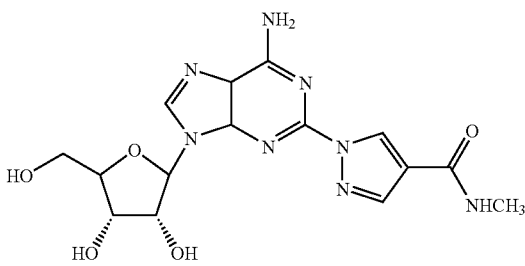

The 1H-pyrazole-4-carboxamides can be prepared starting with 1H-pyrazole-4-carboxylic acid, available from Aldrich Chemical Co. In the first step, the acid is converted to an ester, e.g., a methyl or ethyl ester. The ester converted to the amide via aminolysis, e.g., with methylamine to form the methyl amide. The pyrazole-4-carboxamide will react with the 2-halopurines in the presence of a strong base to provide the 2-(pyrazol-1-yl)adenosine compounds having formula (III).

Another exemplary group of agonists of $A_{2A}$ adenosine receptors include compounds having general formula (IV):

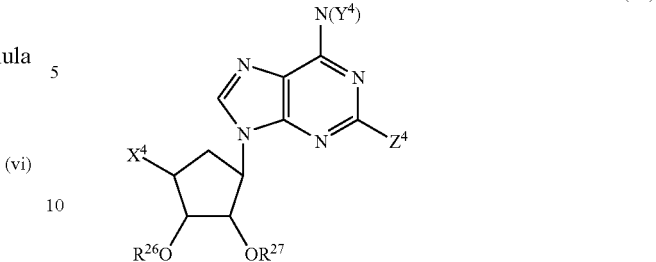

(IV)

wherein $Z^4$ is —$NR^{28}R^{29}$;
$R^{28}$ is hydrogen or ($C_1$-$C_4$) alkyl; and $R^{29}$ is
(a) ($C_1$-$C_4$) alkyl;
(b) ($C_1$-$C_4$) alkyl substituted with one or more ($C_1$-$C_4$) alkoxy, halogen, hydroxy, amino, mono(($C_1$-$C_4$) alkyl)amino, di(($C_1$-$C_4$) alkyl)amino or ($C_6$-$C_{10}$) aryl wherein aryl is optionally substituted with one or more halogen, hydroxy, amino, ($C_1$-$C_4$)alkyl, $R^{30}$OOC—(($C_1$-$C_4$) alkyl)-, $R^{31}R^{32}$NC(=O)—(($C_1$-$C_4$)alkyl)-, mono(($C_1$-$C_4$)alkyl)amino or di(($C_1$-$C_4$)alkyl)amino;
(c) ($C_6$-$C_{10}$)aryl; or
(d) ($C_6$-$C_{10}$)aryl substituted with one or more halogen, hydroxy, amino, mono(($C_1$-$C_4$)alkyl)amino, di(($C_1$-$C_4$) alkyl)amino or ($C_1$-$C_4$)alkyl;
wherein each $Y^4$ is independently hydrogen, ($C_1$-$C_6$)alkyl, ($C_3$-$C_7$)cycloalkyl, phenyl or phenyl($C_1$-$C_3$)alkyl; and $X^4$ is —C(=O)$NR^{31}R^{32}$, —COO$R^{30}$, or —CH$_2$O$R^{30}$;
wherein each of $R^{31}$ and $R^{32}$ are independently; hydrogen; $C_{3-7}$-cycloalkyl; ($C_1$-$C_4$)alkyl; ($C_1$-$C_4$)alkyl substituted with one or more ($C_1$-$C_4$)alkoxy, halogen, hydroxy, —COO$R^{33}$, amino, mono(($C_1$-$C_4$)alkyl)amino, di(($C_1$-$C_4$)alkyl)amino or ($C_6$-$C_{10}$)aryl wherein aryl is optionally substituted with one or more halogen, ($C_1$-$C_4$)alkyl, hydroxy, amino, mono(($C_1$-$C_4$)alkyl)amino or di(($C_1$-$C_4$)alkyl)amino; ($C_6$-$C_{10}$)aryl; or ($C_6$-$C_{10}$)aryl substituted with one or more halogen, hydroxy, amino, mono(($C_1$-$C_4$)alkyl)amino, di(($C_1$-$C_4$)alkyl)amino or ($C_1$-$C_4$)alkyl;
$R^{26}$ and $R^{27}$ independently represent hydrogen, lower alkanoyl, lower alkoxy-lower alkanoyl, aroyl, carbamoyl or mono- or di-lower alkylcarbamoyl; and $R^{30}$ and $R^{33}$ are independently hydrogen, ($C_1$-$C_4$)alkyl, ($C_6$-$C_{10}$)aryl or ($C_6$-$C_{10}$) aryl(($C_1$-$C_4$)alkyl); or a pharmaceutically acceptable salt thereof.

Additional exemplary compounds having formula (IV) include compounds where at least one of $R^{28}$ and $R^{29}$ is ($C_1$-$C_4$)alkyl substituted with one or more ($C_1$-$C_4$)alkoxy, halogen, hydroxy, amino, mono(($C_1$-$C_4$)alkyl)amino, di(($C_1$-$C_4$)alkyl)amino or ($C_6$-$C_{10}$)aryl wherein aryl is optionally substituted with one or more halogen, hydroxy, amino, ($C_1$-$C_4$)alkyl, $R^{30}$OOC—($C_1$-$C_4$)alkyl, mono(($C_1$-$C_4$)alkyl) amino or di(($C_1$-$C_4$)alkyl)amino.

Additional exemplary compounds having formula (IV) include compounds where at least one of $R^{31}$ and $R^{32}$ is $C_{1-4}$-alkyl substituted with one or more ($C_1$-$C_4$)alkoxy, halogen, hydroxy, amino, mono(($C_1$-$C_4$)alkyl)amino, di(($C_1$-$C_4$) alkyl)amino or $C_{6-10}$-aryl wherein aryl is optionally substituted with one or more halogen, hydroxy, amino, ($C_1$-$C_4$) alkyl, $R^{30}$OOC—($C_1$-$C_4$)alkylene-, mono(($C_1$-$C_4$)alkyl) amino or di(($C_1$-$C_4$)alkyl)amino.

Additional exemplary compounds having formula (IV) include compounds where at least one of $R^{28}$ and $R^{29}$ is $C_{6-10}$-aryl substituted with one or more halogen, hydroxy, amino, mono(($C_1$-$C_4$)alkyl)amino, di(($C_1$-$C_4$)alkyl)amino or ($C_1$-$C_4$)alkyl.

Additional exemplary compounds having formula (IV) include compounds where at least one of $R^{31}$ and $R^{32}$ is $C_{6-10}$-aryl substituted with one or more halogen, hydroxy, amino, mono(($C_1$-$C_4$)alkyl)amino, di(($C_1$-$C_4$)alkyl)amino or ($C_1$-$C_4$)alkyl.

In an exemplary combination, $R^{31}$ is hydrogen and $R^{32}$ is ($C_1$-$C_4$)alkyl, cyclopropyl or hydroxy-($C_2$-$C_4$)alkyl. $R^{28}$ group is ($C_1$-$C_4$)alkyl substituted with ($C_6$-$C_{10}$)aryl that is in turn substituted with $R^{30}O(O)C$—($C_1$-$C_4$)alkylene-.

An exemplary compound having formula (IVa) is:

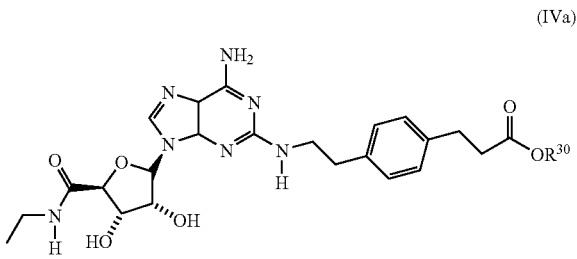

(IVa)

wherein $R^{30}$ is hydrogen, methyl, ethyl, n-propyl or isopropyl. More preferred is a compound wherein the $R^{30}$ group is methyl or ethyl. The most preferred $R^{30}$ group is methyl.

Two additional useful compounds have the formula (IVa) wherein $R^{30}$ is hydrogen (acid, CGS21680) or $R^{30}$ is methyl (ester, JR2171). The compounds having formula (IVa) may be synthesized as described in: U.S. Pat. No. 4,968,697 or *J. Med. Chem.*, 33 1919-1924, (1990).

Additional compounds having $A_{2A}$ agonist activity include IB-MECA, and Cl-IB-MECA shown below.

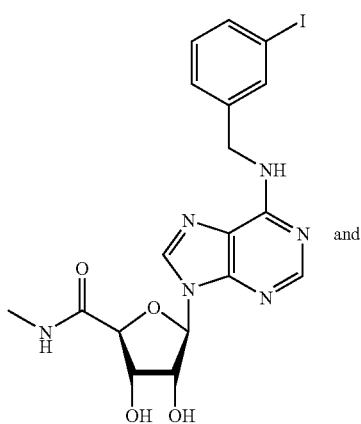

and

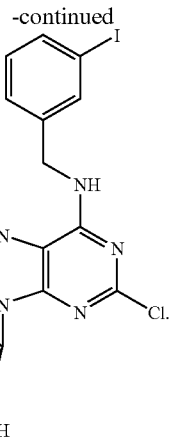

Also preferred are compounds having formula (I), (III), or (IV) that are selective $A_{2A}$ adenosine receptor agonists.

It will be appreciated by those skilled in the art that compounds having formula (I), (III), or (IV) may have more than one chiral center and may be isolated in optically active and racemic forms. Preferably, the riboside moiety of the compounds is derived from D-ribose, e g., the 3N,4N-hydroxyl groups are alpha to the sugar ring and the 2N and 5N groups are beta (3R, 4S, 2R, 5S). When the two groups on the cyclohexyl group are in the 1- and 4-position, they are preferably trans. Some compounds may exhibit polymorphism. It is to be understood that the present invention encompasses any racemic, optically-active, polymorphic, or stereoisomeric compounds, or mixtures thereof, which possess the useful properties described below, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described, or using other similar tests which are well known in the art.

Exemplary $A_{2A}$ adenosine receptor antagonists include 2,7-disubstituted-5-amino-pyrazolo[4,3-e]-[1,2,4]-triazolo [1,5-c]pyrimidines (See e.g., International Patent Application No. WO 01/92264), 2,7-disubstituted-5-amino-[1,2,4]triazolo[1,5-c]pyrimidines (See e.g. International Patent Application No. WO 03/048163), 2,5-disubstituted-7-amino-[1,2,4]triazolo[1,5-a][1,3,5]triazines (See e.g., J. Med. Chem. 2004, 47(17), 4291-4299), 9-substituted-2-(substituted-ethyn-1-yl)-adenines (See e g., U.S. Pat. No. 7,217,702), 7-methyl-8-styrylxanthine derivatives (See e.g., published U.S. Patent Application No. 2006/0128708), pyrazolo [4,3-e)1,2,4-triazolo[1,5-c]pyrimidines (See e.g., published U.S. Patent Application No. 2006/0128708), and 5-amino-imidazolo-[4,3-e]-1,2,4-triazolo[1,5-c]pyrimidines (See e.g., published U.S. Patent Application No. 2006/0128708).

Non-limiting examples of $A_{2A}$ adenosine receptor antagonists include 4-(2-[7-Amino-2-[2-furyl][1,2,4]triazolo[2,3-a][1,3,5]triazin-5-yl-amino]ethyl)phenol (ZM2141385), 8-[2-(3,4-dimethoxy-phenyl)-vinyl]-7-methyl-1,3-dipropyl-3,7-dihydro-purine-2,6-dione (istradefylline, KW6002), 2-furan-2-yl-7-phenethyl-7H-pyrazolo[4,3-e][1,2,4]triazolo [1,5-c]pyrimidin-5-ylamine (SCH58261), VR2006, (−)-R,S)-mefloquine, 3,7-Dimethyl-1-propargylxanthine (DMPX), 3-(3-hydroxypropyl)-7-methyl-8-(m-methoxystyryl)-1-propargylxanthine (MX2), 3-(3-hydroxypropyl)-8-(3-methoxystyryl)-7-methyl-1-propargylxanthine phosphate disodium salt (MSX-3), KW-6002, 8-chlorostyrylcaffeine, KF17837, VER-11135, VER-6409, VER 6440, VER 6489, VER 6623, VER 6947, VER 7130, VER 7146, VER 7448, VER 7835, VER 8177, a pharmaceutically acceptable salt or mixture thereof.

The structure of ZM241385, istradefylline (KW6002) and SCH58261 are respectively:

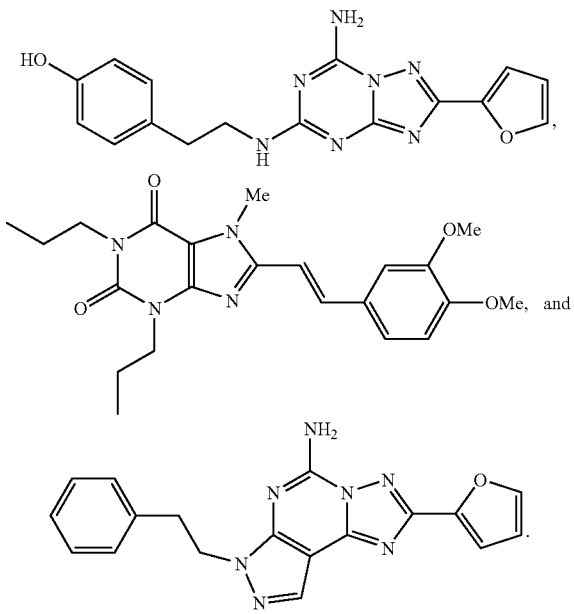

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Exemplary inorganic salts that may also be formed, include hydrochloride, sulfate, nitrate, bicarbonate, and carbonate salts.

Pharmaceutically acceptable salts may be obtained using standard procedures well known in the art, for example by reacting a sufficiently basic compound such as an amine with an acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

The $A_{2A}$ compounds can conveniently be administered in a pharmaceutical composition containing the compound in combination with an excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides.

For topical administration, the present compounds may be applied in pure form, e g., when they are liquids. However, it will generally be desirable to administer them to the skin as compositions or formulations, in combination with a dermatologically acceptable carrier, which may be a solid or a liquid.

In accordance with one embodiment, a composition is provided that comprises a compound of the invention, or an analog, derivative, or modification thereof, and albumin, more particularly, the composition comprises a compound of the present invention, a pharmaceutically acceptable carrier and 0.1-1.0% albumin. Albumin functions as a buffer and improves the solubility of the compounds. In one aspect, albumin is not added.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of compounds having formula (I), (III) or (IV) can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

In one embodiment, the pharmaceutical compositions useful for practicing the invention may be administered to deliver a dose of between 10 ng/kg/day and 10 mg/kg/day. In another embodiment, the pharmaceutical compositions useful for practicing the invention may be administered to deliver a dose of between 100 ng/kg/day and 1 mg/kg/day.

The compositions can conveniently be administered orally, sublingually, transdermally, or parenterally at dose levels of about 0.01 to about 150 μg/kg, preferably about 0.1 to about 50 μg/kg, and more preferably about 0.1 to about 10 μg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The preparation of the $A_{2A}$ modulator compounds are disclosed, erg., in U.S. patent application Ser. No. 10/263,379, filed Oct. 1, 2002, published as U.S. Application No. 2003/0186926 on Oct. 2, 2003 and can generally be prepared as illustrated in Schemes 1A and 1B below. Star ting materials can be prepared by procedures described in these schemes, procedures described in the General methods below or by procedures that would be well known to one of ordinary skill in organic chemistry. The variables used in Schemes 1A and Scheme 1B are as defined above or as in the claims.

The preparation of alkynyl cycloalkanols is illustrated in Scheme 1A. A solution of an appropriate cycloalkanone (where j is from 0-5) is prepared in a solvent such as THF. A solution of an ethynylmagnesium halide compound in a solvent is added to the cycloalkanone. After addition, the solution is allowed to stir at about 20° C. for about 20 hours. The reaction is monitored via TLC until the starting material is consumed. The reaction is quenched with water, filtered over a plug of sand and silica, washed with a solvent, such as EtOAc, and evaporated to provide the product. Two products can be formed, the isomers formed by the axial/equatorial addition of the alkyne (where m is as defined above, and the sum of m1 and m2 is from 0 to about 7) to the ketone. The compounds are purified via flash chromatography using EtOAc/Hexanes to provide the product.

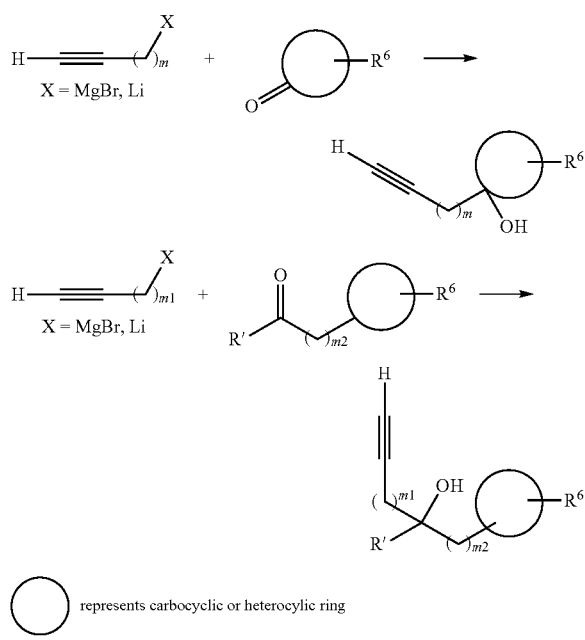

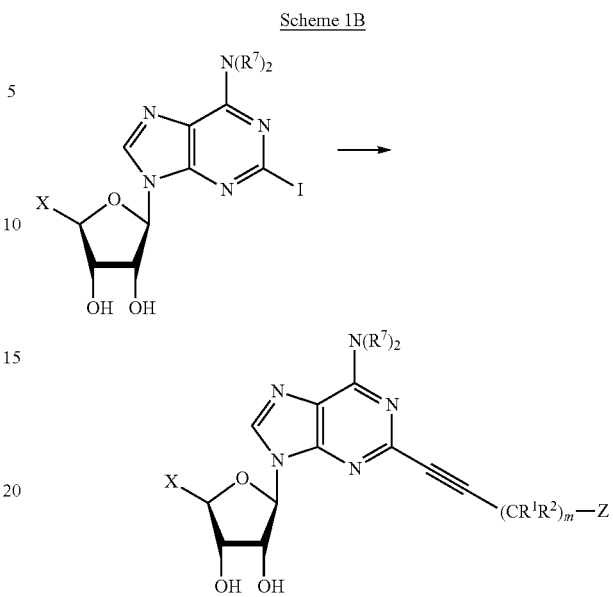

Scheme 1B

The following abbreviations have been used:

| | |
|---|---|
| 2-Aas | 2-alkynyladenosines; |
| $A_{2A}R$ | adenosine $A_{2A}$ receptor; |
| $A_{2A}R$ −/− or KO | $A_{2A}R$ gene deletion or knockout mice; |
| ADA | Adenosine deaminase; |
| ATL202 | 4-{3-[6-amino-9-(5-ethylcarbamoyl-3,4-dihydroxy-tetrahydro-furan-2-yl)-9H-purin-2-yl]-prop-2-ynyl}-piperidine-1-carboxylic acid methyl ester; |
| ATL210 | 4-{3-[6-amino-9-(5-ethylcarbamoyl-3,4-dihydroxy-tetrahydro-furan-2-yl)-9H-purin-2-yl]-prop-2-ynyl}-piperidine-1-carboxylic acid isobutyl ester; |
| ATL313 | $A_{2A}$ agonist, 4-{3-[6-amino-9-(5-cyclopropylcarbamoyl-3,4-dihydroxy-tetrahydro-furan-2-yl)-9H-purin-2-yl]-prop-2-ynyl}-piperidine-1-carboxylic acid methyl ester; |
| BMDC | bone marrow derived cells; EC, Eriochrome Cyanine Staining; |
| HE | Hematoxylin & Eosin Staining; |
| KO/WT, WT/KO, or WT/WT | bone marrow chimeric donor/recipient mice, knockout mice, BBB, mouse BBB locomotor scoring system; |
| SCI | spinal cord injury; |
| SEM | standard error of mean; |
| tBBB | transformed BBB scale; |
| WT | wild type mice; |
| $^{125}$I-ABA | $N^6$-(4-amino-3-$^{125}$iodo-benzyl)adenosine |
| APCI | Atmospheric pressure chemical ionization |
| ATL146e | 4-{3-[6-Amino-9-(5-ethylcarbamoyl-3,4-dihydroxy-tetrahydro-furan-2-yl)-9H-purin-2-yl]-prop-2-ynyl}cyclo-hexanecarboxylic acid methyl ester; |
| CCPA | 2-chloro-$N^6$-cyclopentyladenosine; |
| CGS21680 | 2-[4-(2-carboxyethyl)phenethylamino]-5'-N-ethylcarboxamido-adenosine; |
| Cl-IB-MECA | $N^6$-3-iodo-2-chlorobenzyladenosine-5'-N-methyluronamide, |
| CPA | $N^6$-cyclopentyladenosine |
| DMF | dimethylformamide |
| DMSO | dimethylsulfoxide |
| DMSO-$d_6$ | deuterated dimethylsulfoxide |
| EtOAc | ethyl acetate |
| eq | equivalent |
| GPCR | G protein coupled receptor; h$A_{2A}$AR, Recombinant human $A_{2A}$ adenosine receptor; |
| IADO | 2-Iodoadenosine |
| $^{125}$I-APE | 2-[2-(4-amino-3-[$^{125}$I]iodophenyl)ethylamino]adenosine; |
| NECA | 5'-N-ethylcarboxamidoadenosine; |
| IB-MECA | $N^6$-3-iodobenzyladenosine-5'-N-methyluronamide; |

The preparation of 2-alkynyladenosines is illustrated in Scheme 1B. A flame-dried round bottom under nitrogen is charged with 5-(6-amino-2-iodo-purin-9-yl)-3,4-dihydroxy-tetrahydrofuran-2-carboxylic acid ethylamide (NECA 2-Iodoadenosine) and a solvent such as DMF. The appropriate alkyne, wherein R is a —(CR$^1$R$^2$)$_m$ Z group, is dissolved in acetonitrile followed by TEA, 5 mole % Pd(PPh$_3$)$_4$, and CuI. All solvents are thoroughly degassed.

The solution is allowed to stir for about 24 hours at room temperature, and monitored until complete by HPLC. If the reaction is not complete after this time, additional catalyst, CuI, and TEA are added. After the reaction is complete, the solvents are removed under high-vacuum and the residue taken up in a small amount of DMF. This product is isolated using preparative silica TLC. The product is purified by RP-HPLC.

| | -continued |
|---|---|
| 2-Iodoadenosine | 5-(6-amino-2-iodo-purin-9-yl)-3,4-dihydroxytetra-hydro-furan-2carboxylic acid ethylamide |
| HPLC | high-performance liquid chromatography |
| HRMS | high-resolution mass spectrometry |
| ZM241385 | $A_{2A}$ antagonist, 4-(2-[7-Amino-2-[2-furyl][1,2,4]triazolo[2,3-a][1,3,5]triazin-5-yl-amino]ethyl)phenol; |
| $^{125}$I-ZM241385 | $^{125}$I-4-(2-[7-amino-2-[2-furyl][1,2,4]triazolo[2,3-a][1,3,5]-triazin-5-yl-amino]ethyl)phenol; |
| INECA | 2-iodo-N-ethylcarboxamidoadenosine |
| LC/MS | liquid chromatography/mass spectrometry |
| m.p. | melting point |
| MHz | megahertz |
| MRS 1220 | N-(9-chloro-2-furan-2-yl-[1,2,4]triazolo[1,5-c]quinazolin-5-yl)-2-phenylacetamide ; |
| MS | mass spectrometry |
| NECA | N-ethylcarboxamidoadenosine |
| NMR | nuclear magnetic resonance |
| RP-HPLC | reverse phase high-performance liquid chromatography |
| TBAF | tetrabutylammonium fluoride |
| TBS | tert-butyldimethylsilyl |
| TBDMSCl | tert-butyldimethylsilylchloride |
| TEA | triethylamine |
| TFA | trifluoroacetic acid |
| THF | tetrahydrofuan |
| TLC | thin layer chromatography |
| p-TSOH | para-toluenesulfonic acid |
| XAC | 8-(4-((2-a-minoethyl)aminocarbonyl-methyloxy)-phenyl)-1-3-dipropylxanthine. |

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out some embodiments of the present invention, and are not to be construed as limiting in any way the remainder of the disclosure. Therefore, the examples should be construed to encompass any and all variations which become evident as a result of the teaching provided herein.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

Reagents

Adenosine deaminase (ADA) was purchased from Roche. 5'-N-ethylcarbox-amidoadenosine (NECA) was purchased from Sigma-Aldrich. 4-{3-[6-amino-9-(5-ethyl-carbamoyl-3,4-dihydroxy-tetrahydro-furan-2-yl)-9H-purin-2-yl]-prop-2-ynyl}-piperidine-1-carboxylic acid methyl ester (ATL202), 4-{3-[6-amino-9-(5-ethylcarbamoyl-3,4-dihydroxy-tetrahydro-furan-2-yl)-9H-purin-2-yl]-prop-2-ynyl}-piperidine-1-carboxylic acid isobutyl ester (ATL210), and 4-{3-[6-amino-9-(5-cyclopropylcarbamoyl-3,4-dihydroxy-tetrahydro-furan-2-yl)-9H-purin-2-yl]-prop-2-ynyl3-piperidine-1-carboxylic acid methyl ester (ATL313) were gifts from Adenosine Therapeutics, LLC. Some of the chemical structures are shown in Table 2. 4-(2-[7-Amino-2-[2-furyl][1,2,4]triazolo[2,3-a][1,3,5]triazin-5-yl-amino]ethyl)phenol (ZM241385) was purchased from Tocris.

Animals

Female C57BL/6 mice between 6-18 weeks of age were purchased from Jackson Laboratory (Bar Harbor, Me.). $A_{2A}R$ −/− mice from Jiang-Fan Chen of Boston University were selectively bred with the aid of microsatellite markers to be congenic with C57BL/6 and were age- and sex-matched to wild type controls. Food and water were provided ad libitum before and after the experiments. Animals were housed in a pathogen-free isolation barrier facility with chip bedding.

EXAMPLE 1

Bone Marrow Transplantation (BMT)

Female mice 7-9 weeks of age were irradiated twice with 600 Rads separated by 4 hours. Bone marrow donor mice 12 weeks of age were sacrificed by a lethal injection of sodium pentobarbital. Bone marrow cells were harvested from femurs and tibia by flushing with RPMI-1640 medium (Invitrogen Corporation, Grand Island, N.Y.) in the presence of 10% heat-inhibited fetal bovine serum (FBS). Connective tissue and debris were carefully removed by washing and centrifuging. Red blood cells were lysed by 1× ZAP-OGLO-BIN® II lytic Reagent (Beckman Coulter, Miami, Fla.). Recipient mice were anesthetized intraperitoneally with a mixture of 100 mg/ml ketamine and 20 mg/ml xylazine in saline solution. An aliquot of approximately $2 \times 10^6$ cells in 200 µl RPMI-1640 with 10% FBS was injected intravenously through left or right jugular vein. BMT mice were used for experiments after 6 weeks. We have previously shown that this procedure results in efficient repopulation of BMDC cells to irradiated mice (Day et al., 2005).

EXAMPLE 2

Spinal Cord Compression

Animals were subjected to transient spinal cord compression using a protocol approved by the University of Virginia Animal Care and Use Committee (Li et al., 2006). Briefly, mice were anesthetized with a mixture of ketamine and xylazine and placed on a heating pad in a stereotaxic apparatus. A laminectomy was performed at T12 and two adjustable forceps were applied to the vertebra between T11 to T13 to stabilize the spinal cord. Ischemic injury was produced by gently placing a 15 gram compression rod with 1 mm×2 mm rectangular surface onto the intact durra for 5 minutes. Mice were kept warm until they regained consciousness and were injected IP with $A_{2A}R$ specific agonists (ATL202, ATL210, or ATL313), the antagonist (ZM241385), or vehicle (3% DMSO in PBS) 5 minutes before spinal cord compression, on the evening after surgery, and twice daily for the next 3 days. In some of studies, the administration of ATL313 started right after the injury in a similar treatment paradigm. Injured mice were assessed on post-SCI days 1, 4, 7, 14, 28, and 42. Sham animals received a laminectomy without spinal cord compression. Following SCI, bladders were expressed twice daily until return of normal bladder function.

EXAMPLE 3

Locomotor Assessment

The mouse BBB scale (Li et al., 2006) was used to assess locomotor function after spinal cord compression. Briefly, bar walking (Isaksson et al., 2000; Farooque, 2000) replaced certain elements of the rat BBB scale (Basso et al., 1996;

Basso et al., 1995) that are not applicable to mice. Animals that were able to walk and scored greater than 14 based on rat BBB scoring criteria were further evaluated based on their ability to traverse steel bars without slipping. Mice were placed on bars 500 mm in length and 3 mm in thickness with decreasing widths: 20 mm (score 16), 15 mm (score 17), 10 mm (score 18), 7 mm (score 19), and 5 mm (score 20). A score of 15 was assigned to mice that failed to traverse the widest bar without slipping. Scores obtained from left and right hind limbs were averaged. In some experiments locomotor function was also scored using the tBBB score that has been devised to minimize inter-laboratory scoring differences (Ferguson et al., 2004).

EXAMPLE 4

Spinal Cord Histology

A section of spine between T10 and L1 was removed under anesthesia. The tissue was placed in 4.0% paraformaldehyde in phosphate buffered saline, pH 7.4, and rocked for 4 hours. The disc body, lamina, pedicle, spinous and transverse processes surrounding the cord were carefully removed and the cord trimmed to center the injured area in a 10 mm segment. After incubation at 4° C. overnight, tissues were washed in Dulbecco's phosphate buffered saline (PBS, pH 7.4) twice for 10 minutes, and transferred to cassettes in 70% ethanol for paraffin embedding. Five µm sections were collected at 500 µm intervals using a Leica RM2030 Rotary Microtome. Sections derived from the center of the 2 mm compression zone were stained with hematoxylin & eosin (HE) and eriochrome cyanine (EC) as described below. Slides were examined using an Olympus BX51 light microscope and photographed using an Olympus DP70 digital camera (4080×3072 pixels) with DP70-BSW-V1.2 Capture & Archiving Software.

Hematoxylin & Eosin (HE) Staining. Sections were deparaffinized at 37° C. twice each for 5 minutes in xylene, 100% ethanol, and 95% ethanol, then once for 5 minutes in 70% ethanol and twice for 5 minutes in $dH_2O$. Slides were stained in filtered hematoxylin for 60 seconds and washed in tap water for 3 minutes, stained in Eosin Y for 30 seconds and washed in tap water for 3 minutes. After the slide was dehydrated to xylene, a coverslip was applied.

Eriochrome Cyanine (EC) Staining. The protocol for staining myelin was obtained from the NINDS Spinal Cord Injury Training Course 2004 (The Ohio State University, Columbus, Ohio) and used with minor modifications. Briefly, spinal cord paraffin sections were deparaffinized as described above, rehydrated through graded ethanol solutions (twice each in 100% & 95% ethanol, once in 70% ethanol, and twice in $dH_2O$). After drying for 1-2 hours in a slide warmer at 37° C., slides were placed in acetone at room temperature for 5 minutes, rinsed 5 times in $dH_2O$, stained in EC Solution (0.2% eriochrome cyanine RS, 0.5% sulfuric acid, and 0.4% ferric ammonium sulfate) at room temperature for 30 minutes, gently washed in running tap water for 5 minutes, and further briefly rinsed in $dH_2O$. Slides were differentiated in 5% ferric ammonium sulfate at room temperature for 5-10 minutes, briefly rinsed in $dH_2O$, placed in a mixture of 1% borax and 1.25% potassium ferricyanide at room temperature, rinsed 5 times in $dH_2O$ (deionized water), dehydrated briefly through graded ethanol solutions (two changes each in 70%, 95%, and 100% ethanol), cleared briefly through xylene 3 times, and placed under a coverslip using a permanent mounting medium.

Spinal Cord Cross Sectional Area and Myelin Quantification. Total cross-sectional area was measured to determine the extent of spinal cord atrophy, Cross-sectional area stained with EC was calculated by image analysis to evaluate damage of the sagittal myelinated tracts. White matter in injured cord stained with EC was normalized to white matter in sham control cord accordingly. The loss in white matter of each sample was calculated as % of total area stained in respective areas of control samples.

EXAMPLE 5

Radioligand Binding Assays

Membranes from HEK293 cells stably expressing recombinant mouse $A_{2A}Rs$ or $A_3Rs$ were used for competition binding assays with $[^{125}I]N6$-4-amino-3-iodobenzyladenosine for the $A_3AR$ or $[^{125}I]2$-[2-(4-amino-3-iodophenyl)ethylamino]adenosine for the $A_{2A}R$ as described previously (Lappas et al., 2005a). Radioligand binding experiments were performed with 25 µg of HEK293 cell membrane protein in a total volume of 0,1 ml of 10 MM HEPES with 1 mM EDTA (pH 7.4) supplemented with 2 Unit/ml adenosine deaminase and 5 mM $MgCl_2$. Nonspecific binding was measured in the presence of 100 µM NECA. The incubation time was 120 min at room temperature. Membranes were filtered on Millipore MultiScreen 96-well filtration plates and washed three times with ice-cold buffer (10 mM Tris, 1 mM $MgCl_2$, pH 7,4) using a Brandel 96-well plate washer. The data were fit to a four-parameter logistic equation. $IC_{50}$ values were determined using GraphPad Prism, and Ki values calculated (Linden, 1982).

Statistical Analysis: Statistical analyses were conducted using SAS version 9.1 (SAS Institute Inc, Cary, N.C.). A mixed model (SAS Proc Mixed) was applied to determine the effect of drug treatment over time. Both the experimental condition (mouse genotype and/or drug) and the day were set as categorical variables. An autoregressive correlation structure was assumed for repeated measures in the entire study. Locomotor scores obtained over 42 days were found to reach a plateau in 14 days. Hence, in some experiments, pooled data were averaged from days 14, 28 and 42, as the "plateau response." Differences between experimental groups for the entire experimental period or during the plateau phase were analyzed by ANOVA and Bonferroni post hoc testing.

EXAMPLE 6

Radioligand Binding Assays

Figure 1A:
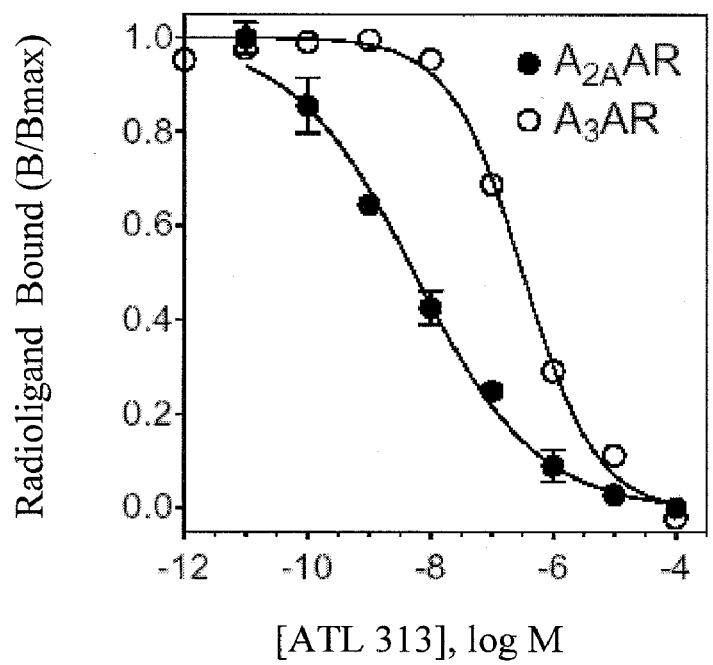
FIG. 1A and FIG. 1B illustrate the binding of adenosine analogs to recombinant mouse adenosine $A_{2A}$ and $A_3$ receptors. Competition by agonist, ATL313 (A) and an antagonist, ZM241385 (B) for radioligand binding to recombinant mouse $A_{2A}$ or $A_3$ receptors. Each point is the mean±SEM of triplicate determinations. $K_i$ determinations from triplicate experiments are summarized in Table 6.
Figure 1B:
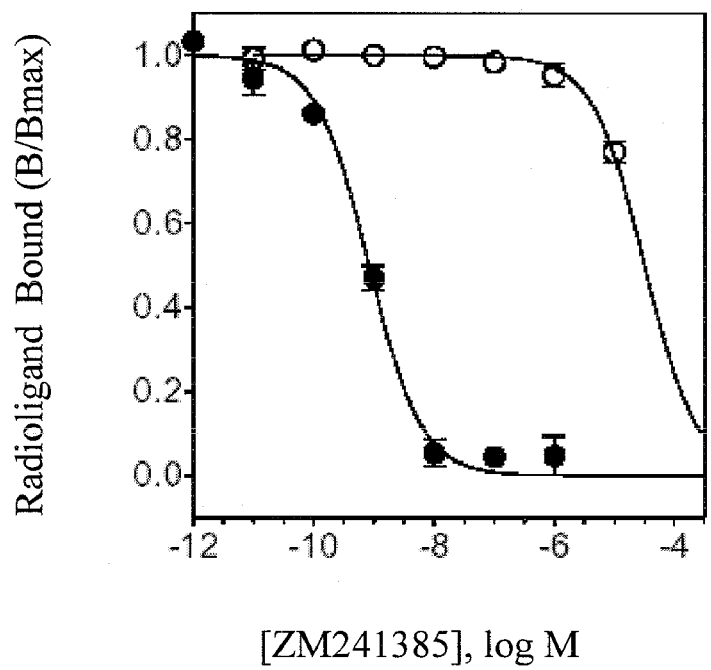

ATL146e and CGS21680 have been widely used as $A_{2A}$ agonists based on their high affinity and selectivity for recombinant human $A_{2A}$ receptors (Rieger et al., 2001). These and other newly synthesized agonist compounds (FIG. 1) and the antagonist, ZM241385 in competition for radioligand binding to recombinant murine adenosine receptor subtypes were examined. All agonists evaluated bind weakly ($K_i$>100 nM) to murine $A_1$ and $A_{2B}$ receptors (data not shown). The binding to murine $A_{2A}$ and $A_3$ receptors is illustrated in FIG. 1 and tabulated in Table 6. It is important to note that unlike human receptors, in the mouse, the selectivity of all of these agonist compounds for the $A_{2A}$ over the $A_3$ receptor is limited, and the administration of these compounds to mice is expected to produce some degree of $A_3$ receptor activation. However, as with human receptors, the antagonist ZM241385 is highly (>40,000 fold) selective for the mouse $A_{2A}$ over the $A_3$ receptor. Activation of the $A_3$ receptor may exacerbate inflammation by enhancing the degranulation of rodent mast cells (Jin et al., 1997; Ramkumar et al., 1993, Reeves et al., 1997);

although tissue protection by $A_3$ receptor activation also has been noted (Rivo et al., 2004). Based on these data, we conclude that ATL313 is superior to ATL146e and CGS21680 as a potent agonist of the mouse $A_{2A}R$, and that ZM241385 is a useful tool for distinguishing between $A_{2A}$- and $A_3$-mediated responses in mice.

TABLE 6

Binding affinity (Ki, nM) of the high affinity conformational states of recombinant mouse $A_{2A}$ and $A_3$ receptors.

| Compound | $A_{2A}R$ | $A_3R$ | $A_3/A_{2A}$ |
|---|---|---|---|
| ATL146e | 1.60 ± 0.50 | 3.3 ± 2.0 | 2.1 |
| ATL202 | 1.50 ± 0.55 | 3.7 ± 0.4 | 2.5 |
| ATL210 | 1.04 ± 0.26 | 5.4 ± 0.7 | 5.2 |
| ATL313 | 1.58 ± 0.48 | 19.3 ± 3.3 | 12.2 |
| CGS21680 | 11.00 ± 3.00 | 160 ± 20 | 14.5 |
| ZM241385 | 0.39 ± 0.10 | 16,100 ± 1,250 | 41,300 |

Values are means ± SEM. Data were derived from at least six experiments, each having of 7 concentrations of competing compound.

EXAMPLE 7

Effects of $A_{2A}R$ Agonists and an Antagonist on Mouse SCI

In initial SCI experiments, the dose-dependence of ATL313 to reduce injury was investigated. An initial dose range 2-20 nmol/kg (1-10 μg/kg) was selected based on prior findings in a mouse liver ischemia-reperfusion injury model (Day et al., 2005). ATL313 administered twice daily for 4 days during and following spinal cord compression injury was found to improve locomotor activity in mice as reflected by a significant and sustained increase in the mBBB locomotor score (p<0.0001). Delaying treatment until just after reperfusion produced equal protection (see below).

Figure 2A:
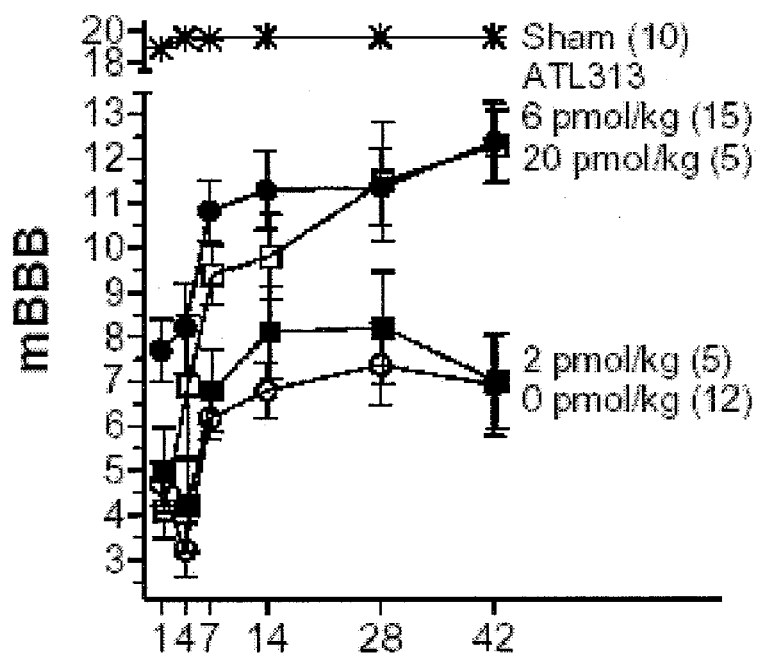
FIG. 2A, FIG. 2B, FIG. 2C and FIG. 2D illustrate the use of $A_{2A}$R agonists protect mice from spinal cord compression. Mice were injected IP with vehicle or $A_{2A}$R agonists and evaluated to assess locomotor function based on the mBBB score where higher scores indicate improved locomotor function. A) Dose-dependence of ATL313 to reduce SCI. B) Results of triplicate experiments with 6 nmol/kg ATL313 run on different days. C) Comparison of 6 nmol/kg ATL313 and another agonist, ATL202. D) Early blockade of 6 nmol/kg ATL313 by equimolar antagonist, ZM241385.
Figure 2B:
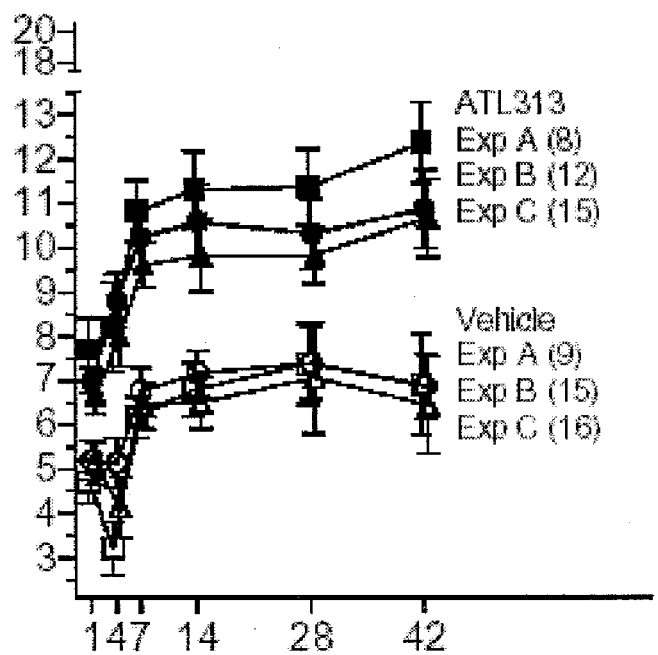
Figure 2C:
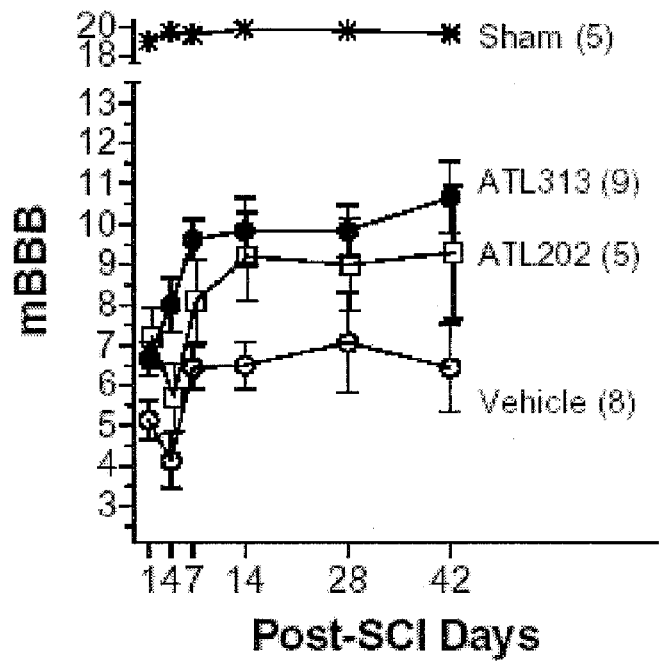

As shown in FIG. 2A, the optimal ATL313 dose is 6 nmol/kg, with no significant protection elicited by 2 nmol/kg. Increasing the dose from 6 to 20 nmol/kg does not produce additional protection. Locomotor function following spinal cord compression injury improves for 1-2 weeks, long after drug treatment has ended, and then reaches a plateau that persists for the entire 42 day duration of the experiment, probably indicative of a permanent improvement in spinal cord function. ATL313 improved locomotor function at all time points between 1 and 42 days after injury. The magnitude of spinal cord protection produced by ATL313 is reproducible, with nearly identical results observed in three independent experiments (FIG. 2B). As compared to ATL313, ATL202 is an agonist with equal affinity for the mouse $A_{2A}$ receptor, but higher affinity for the $A_3$ receptor. ATL202 was found to produce somewhat less protection (p<0.05) than ATL313 (FIG. 2C).

Figure 2D:
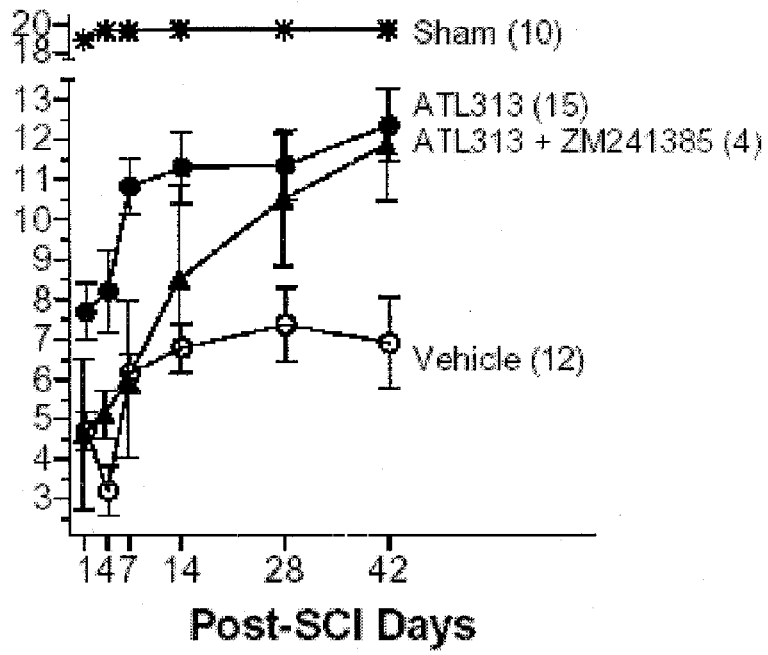

The effect of the adenosine $A_{2A}$ receptor antagonist ZM241385 on spinal cord compression injury was examined. The antagonist ZM241385 produced an improvement in locomotor function that was similar to the effect of the agonist, ATL313. Addition of a combination of the agonist and the antagonist resulted in a transient diminution of locomotor function compared to the effect of either compound alone, but this was followed in time by a gradual improvement (FIG. 2D). The data suggest that activation of $A_{2A}Rs$ influence two or more processes that have opposing effects on locomotor function.

EXAMPLE 8

Morphological Evidence that ATL313 Reduces SCI

Figure 3:
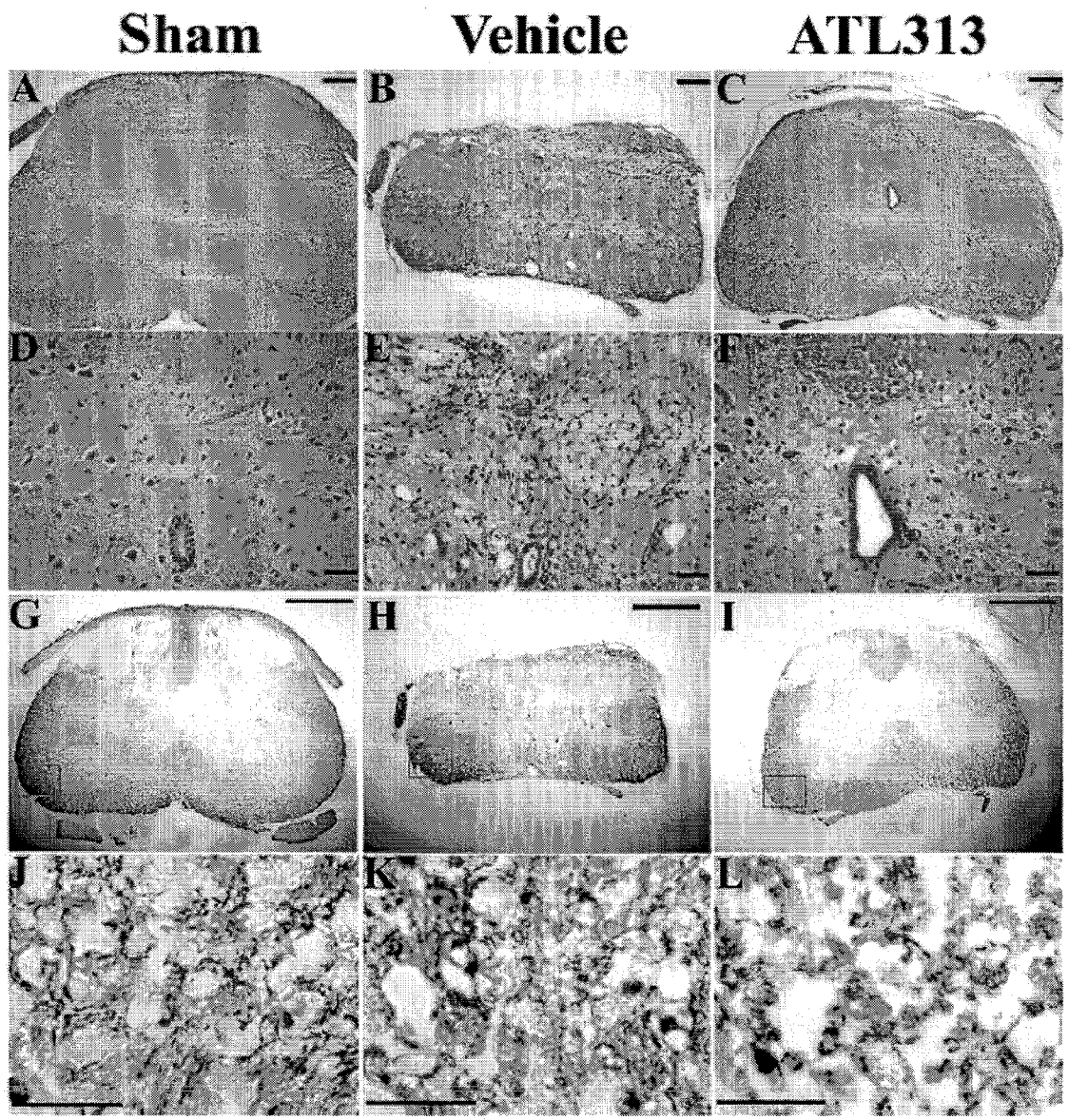
FIG. 3A-FIG. 3L, illustrate morphological evidence of mouse spinal cord protection with the $A_{2A}$ agonist compound ATL313. Mice were treated with either vehicle (n=4) or 6 nmol/kg ATL313 (n=3) following spinal cored compression. Spinal cords were prepared for staining with H&E (FIGS. 3A-3F) or EC (FIGS. 3G-3I) on day 42 after injury.
Figure 4:
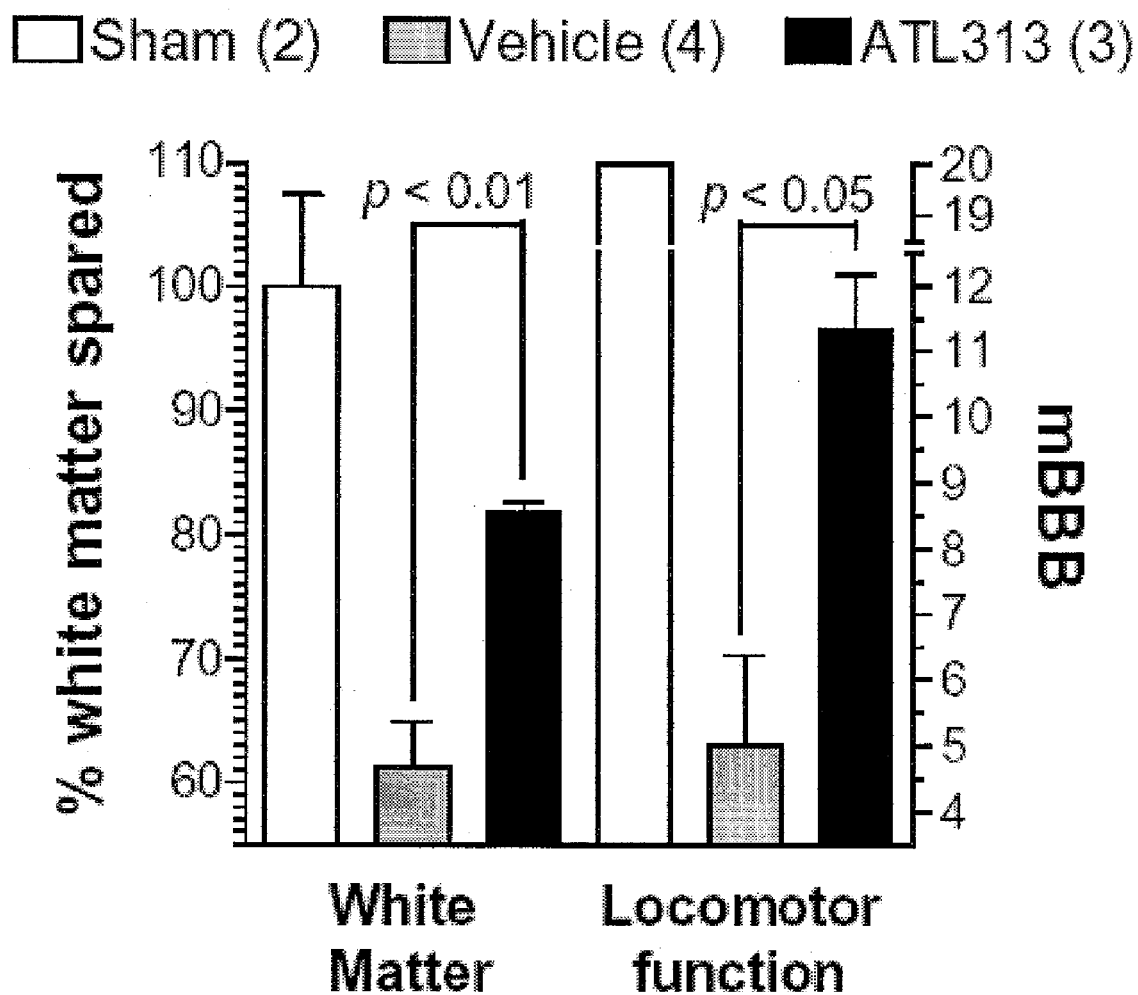
FIG. 4 is an illustration of a comparison of the effects of the compound ATL313 on spinal cord myelin content and locomotor activity following spinal cord compression. EC-stained cross-sections examined under lower magnification (see FIGS. 3G-3I) were analyzed to assess loss of white matter calculated as (blue-stained/total) cord areas normalized to 2 sham animals. Spared myelin in mice treated with vehicle, 61.0%±3.6%, was significantly increased to 81.9±0.9%, n=3, in animals treated with 6 nmol/kg ATL313. In the same animals the mBBB score in mice treated with vehicle (5.0±1.4, n=3) was significantly increased in animals treated with ATL313 (11.3±0.8, n=4).

Histological examination of the spinal cord 42 days after compression injury revealed persistent morphological changes with loss of tissue mass on the dorsal and ventral surfaces compared to uninjured control or ATL313-treated mice (FIG. 3 A-C). The white matter areas of injured spinal cord on day 42 following either vehicle treatment (FIG. 3B) or ATL313 treatment (FIG. 3C) normalized to sham controls processed in parallel (FIG. 3A) was calculated. The average ratio of spinal cord white area (injured/sham) for vehicle and ATL313 treated animals was 61.3±3.6 and 81.9±0.9, respectively, N=3-4, P<0.05. The injured cords appeared disorganized and vacuolated. These effects were reduced by administration of ATL313 (FIG. 3D-F). Myelin (blue staining) was lost, particularly from the dorsal portion of the injured cord, but also from the ventral medial area, but there appeared to be increased myelin at day 42 in the ventral horn of the incurred cord (FIGS. 3G-I). The number of myelinated axons stained pink or white was less in the injured than in the uninjured cord (FIG. 3J-3L), and there was an accumulation of cells that stain darkly with EC, probably oligodendrocytes. All of these manifestations of long-term spinal cord injury were substantially reversed in animals treated with ATL313 (FIGS. 3C, 3F, 3I, and 3L). Demyelination was quantified based on areas of the cord where EC staining was weak or absent (FIG. 3G-3I). The remaining well organized and darkly stained areas were reduced in area to 61.0%±3.6% and 81.9±0.9% of uninjured regions in control ATL313-treated mice, respectively. Locomotor function was well correlated with preservation of myelin (FIG. 4).

EXAMPLE 9

Spinal Cord Protection by $A_{2A}$ Agonists is Mediated by BMDC Cells $A_{2A}R$ agonist-induced spinal cord protection was assessed in bone marrow chimera mice. Responses in chimera mice to spinal cord compression injury over time are plotted in FIGS. 5A-5C, and the plateau phases (pooled from days 14-42) are compared in FIG. 6A and FIG. 6B using both the mBBB and the simplified tBBB scoring systems, with similar results. In all cases, mice that had $A_{2A}Rs$ on BMDC cells (WT, WT/WT, and WT/KO) were protected by ATL313, and mice lacking $A_{2A}Rs$ on BMDC cells (KO/WT) were not protected. Mice in which wild type (WT) marrow was transplanted to WT recipients (WT/WT) were somewhat, but not significantly protected compared to WT controls that were not irradiated. Some protection as a result of BMT could be due to a small immunosuppressive effect of BMT (Kipnis et al., 2004). As in WT mice, ATL313 protected chimeric WT/WT mice.

EXAMPLE 10

Spinal Cord Protection by $A_{2A}R$ Deletion or Blockade

Consistent with the protection from SCI by the antagonist ZM241385 (FIG. 2D) compressive spinal cord injury in global $A_{2A}R$ knock out or WT/KO bone marrow chimera mice was reduced compared to wild type or WT/WT controls (FIGS. 5C and 6). These data suggest that blockade or deletion of $A_{2A}Rs$ on non-BMDC cells (or bone marrow cells that turn over slowly) can produce spinal cord protection. The greatest protection was noted in WT/KO mice treated with AT313, in which the agonist activates receptors on BMDC cells while receptors on non-BMDC cells are selectively deleted. By plotting changes in locomotor function over time in various groups of mice (FIG. 7) illustrates that the effect of $A_{2A}R$ activation of BMDC cells to improve locomotor activity is more rapid (peaks in <4 day) than the effect of $A_{2A}R$ deletion which does not peak until day 14 after compressive spinal cord injury. In addition (FIG. 7) illustrates that there is an additive effects of activating $A_{2A}$ receptors on BMDC cells and deleting $A_{2A}$ receptors on non-BMDC cells.

EXAMPLE 11

Spinal Cord Protection by $A_{2A}R$ Agonist is not Due to Vasodilatation During Compression The results with WT/KO bone marrow chimera also suggest that $A_{2A}$ agonists do not reduce compression injury by effects on blood vessels, since such mice lack $A_{2A}$ receptors on vascular cells. In order to confirm that spinal cord protection is not due to vasodilatation during compression we did a series of experiments in which the administration of ATL313 was postponed until the end of the compression period. This resulted in the same reduction in SCI as starting the agonist prior to reperfusion (FIG. 8). The spinal cord protection by $A_{2A}R$ agonist is not due to vascular effects in the mouse. This agrees with prior observations in the rabbit (Cassada et al., 2002; Reece et al., 2004b; Reece et al., 2004a).

EXAMPLE 12

Signaling by ATL313

Agonists such as CGS21680 and ATL313 are highly selective for human $A_{2A}$ receptor over the other adenosine receptor subtypes, having only moderate selectivity (12-fold) over $A_3$ receptors in the mouse. The $A_{2A}R$ is known to signal by activation of Gs and adenylyl cyclase while the $A_3R$ signals through $G_{i/o}$ to inhibit cyclic AMP production in various cells (Linden, 2001). Three lines of evidence suggest that mouse spinal cord protection is mediated by activation of the $A_{2A}R$ and not the $A_3R$: 1) ATL313 produced as great or greater protection than ATL202 which has similar affinity for the $A_{2A}R$ and higher affinity for the $A_3R$; 2) spinal cord protection by ATL313 is completely absent in mice lacking $A_{2A}$ receptors globally or selectively in BMDCs; and 3) acute spinal cord protection by ATL313 is completely blocked by ZM241385, a weak antagonist of the mouse $A_3$ receptor.

EXAMPLE 13

Effect of Delay in Administering $A_{2A}$ Agonist

Mice were injected IP immediately (0 min), 5, 10, 20, or 60 minutes after SCI with vehicle or $A_{2A}AR$ agonist (ATL313, 3 nmol/kg) then they were treated a second time on the same day and twice daily for 3 additional days (see top of FIG. 9). The mice were evaluated to assess locomotor function as described above. The number of animals was indicated in brackets and 5 mice were taken for sham surgery. Protection on post-injury day 21 was afforded by ATL313 starting 0 to 20 minutes after compression injury (p<0.05). Protection from compression injury was significant with treatment delay for 0, 5 or 20 min, but not 60 min based on two-way ANOVA analysis (matched) with Bonferroni's multiple comparison test. The results are illustrated in FIG. 9

EXAMPLE 14

Effect of Delaying Administration of $A_{2A}$ Antagonist

Mice were injected IP twice daily for 4 days with 6 nol/kg ZM241385 after a delay of 1, 3, 5 or 7 days after compressive injury. Reduction of injury was significant compared to vehicle for all delay periods based on two-way ANOVA analysis (matched) with Bonferroni's multiple comparison test. The results are illustrated in FIG. 10

EXAMPLE 15

Contusion SCI and Locomotor Activity

Female C57BL/6 wild type and Rag-1 KO mice lacking mature lymphocytes between 6-18 weeks of age were purchased from Jackson Laboratory (Bar Harbor, Me.). Adenosine 2A receptor gene deletion ($A_{2A}AR$ −/−, $A_{2A}AR$ knockout) mice were age-matched to their wild types with same genomic background (C57BL/6). Food and water were provided ad libitum before and after experiments. During the experiment period, animals were housed in a pathogen-free isolation barrier region with chip bedding. The protocol is approved by the University of Virginia Animal Care and Use Committee.

Animals were subjected to comtusive spinal cord injury protocol. Briefly, mice were anesthetized with a mixture of ketamine and xylazine and placed on a heating pad in a stereotaxic apparatus. A laminectomy was performed at T12 and two adjustable forceps were applied to the vertebra between T11 to T13 to stabilize the spinal cord. Contusive spinal cord injury (SCI) was produced with an IH device (PSI, Lexington, Ky.) at a defined force from 30 to 100 Kdynes with a dwell time of 30 msec or 60 sec. All mice were kept warm until they regained consciousness. Mice were injected IP with vehicle only (3% DMSO in PBS) or $A_{2A}AR$ specific agonist ATL313 (3 nmol/kg) at 2 min and 2.5 hours after injury. Some mice were dosed with the antagonist ZM241385 (3 nmol/kg) twice daily only on days 2-5 following injury. Injured mice were assessed on days 1, 2, 3, 4, 7, 10, 14, 21, 28, 35, and 42 after injury. Sham animals (n=10) received a laminectomy without spinal cord compression. Following SCI, bladders were expressed twice daily until return of normal reflexive bladder function.

The mouse BBB scale was used to assess locomotor recovery after contusive injury as described previously (Li et al. 2005).

Statistical tests were performed using GraphPad™ Prism version 5 software (GraphPad Software, Inc., San Diego, Calif.). Differences in locomotor scores between groups was analyzed by two-way analysis of variance (ANOVA) employing Bonferroni post-tests for repeated measure comparisons. A P value <0.05 was considered to be significant. The results are illustrated in FIGS. 11A and 11B.

EXAMPLE 16

Dosage Form Preparation

The following illustrate representative pharmaceutical dosage forms, containing a compound of formula I, II ('Compound X'), for therapeutic or prophylactic use in humans.

|  | mg/tablet |
|---|---|
| (i) Tablet 1 | |
| >Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| >Compound X = | 20.0 |
| Microcrystalline cellulose | 410.0 |
| Starch | 50.0 |
| Sodium starch glycolate | 15.0 |
| Magnesium stearate | 5.0 |
| | 500.0 |
| (iii) Capsule | |
| >Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |
| (iv) Injection 1 (1 mg/ml) | |
| >Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |
| (v) Injection 2 (10 mg/ml) | |
| >Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |
| (vi) Aerosol | |
| >Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

BIBLIOGRAPHY

1. Basso D M, Beattie M S, Bresnahan J C, 1995. A Sensitive and Reliable Locomotor Rating-Scale for Open-Field Testing in Rats. Journal of Neurotrauma 12: 1-21.
2. Basso D M, Beattie M S, Bresnahan J C, Anderson D K, Faden A I, Gruner J A, Holford T R, Hsu C Y, Noble L J, Nockels R, Perot P L, Salzman S K, Young W, 1996. MASCIS evaluation of open field locomotor scores: Effects of experience and teamwork on reliability. Journal of Neurotrauma 13: 343-359.
3. Cassada D C, Tribble C G, Young J S, Gangemi J J, Gohari A R, Butler P D, Rieger J M, Kron I L, Linden J, Kern J A, 2002. Adenosine A(2A) analogue improves neurologic outcome after spinal cord trauma in the rabbit. Journal of Trauma-Injury Infection and Critical Care 53: 225-229.
4. Chen J F, Huang Z H, Ma J Y, Zhu J M, Moratalla R, Standaert D, Moskowitz M A, Fink J S, Schwarzschild M A, 1999. A(2A) adenosine receptor deficiency attenuates brain injury induced by transient focal ischemia in mice. Journal of Neuroscience 19: 9192-9200.
5. Day Y J, Huang L P, McDuffie M J, Rosin D L, Ye H. Chen J F, Schwarzchild M A, Fink J S, Linden J, Okusa M D, 2003. Renal protection from ischemia mediated by A(2A) adenosine receptors on bone marrow-derived cells. Journal of Clinical Investigation 112: 883-891.
6. Day Y J, Li Y, Rieger J M, Ramos S I, Okusa M D, Linden J, 2005. $A_{2A}$ adenosine receptors on bone marrow-derived cells protect liver from ischemia-reperfusion injury. Journal of Immunology 174: 5040-5046.
7. Day Y J, Marshall M A, Huang L P, McDuffie M J, Okusa M D, Linden J, 2004. Protection from ischemic liver injury by activation of A(2A) adenosine receptors during reperfusion: inhibition of chemokine induction. American Journal of Physiology-Gastrointestinal and Liver Physiology 286: G285-G293.
8. Dionisotti S, Ferrara S, Molta C, Zocchi C, Ongini E, 1996. Labeling of A(2A) adenosine receptors in human platelets by use of the new nonxanthine antagonist radioligand [H-3]SCH 58261. Journal of Pharmacology and Experimental Therapeutics 278: 1209-1214.
9. Farooque M, 2000. Spinal cord compression injury in the mouse: presentation of a model including assessment of motor dysfunction. Acta Neuropathologica 100: 13-22.
10. Fenster M S, Shepherd R K, Linden J, Duling B R, 2000. Activation of adenosine A(2 alpha) receptors inhibits mast cell degranulation and mast cell-dependent vasoconstriction. Microcirculation 7: 129-135.
11. Ferguson A R, Hook M A, Garcia G, Bresnahan J C, Beattie M S, Grau J W, 2004. A simple post hoc transformation that improves the metric properties of the BBB scale for rats with moderate to severe spinal cord injury. Journal of Neurotrauma 21: 1601-1613.
12. Guertin P A, 2005. Paraplegic mice are leading to new advances in spinal cord injury research. Spinal Cord. 43: 459-461.
13. Huang S, Apasov S, Koshiba M, Sitkovsky M, 1997. Role of A2a extracellular adenosine receptor-mediated signaling in adenosine-mediated inhibition of T-cell activation and expansion. Blood 90: 1600-1610.
14. Isaksson J, Farooque M, Olsson Y, 2000. Spinal cord injury in ICAM-1-deficient mice: Assessment of functional and histopathological outcome. Journal of Neurotrauma 17: 333-344.
15. Isaksson J, Farooque M, Olsson Y, 2005. Improved functional outcome after spinal cord injury in iNOS-deficient mice. Spinal Cord. 43: 167-170.
16. Jin X, Shepherd R K, Duling B R, Linden J, 1997. Inosine binds to A3 adenosine receptors and stimulates mast cell degranulation. J. Clin. Invest. 100: 2849-57.
17. Kipnis J, Avidan H, Markovich Y, Mizrahi T, Hauben E, Prigozhina T B, Slavin S, Schwartz M, 2004. Low-dose gamma-irradiation promotes survival of injured neurons in the central nervous system via homeostasis-driven proliferation of T cells. European Journal of Neuroscience 19: 1191-1198.
18. Koshiba M, Rosin D L, Hayashi N, Linden J, Sitkovsky M V, 1999. Patterns of A(2A) extracellular adenosine receptor expression in different functional subsets of human peripheral T cells. Faseb Journal 13: A944.

19. Lappas C M, Rieger J M, Linden J, 2005a. A(2A) adenosine receptor induction inhibits IFN-gamma production in murine CD4(+) T cells. Journal of Immunology 174: 1073-1080.
20. Lappas C M, Sullivan G W, Linden J. 2005b. Adenosine A2A agonists in development for the treatment of inflammation, Expert Opinion on Investigational Drugs 14: 797-806.
21. Lee Y L, Shih K, Bao P, Ghirnikar R S, Eng L F, 2000. Cytokine chemokine expression in contused rat spinal cord. Neurochemistry International 36: 417-425.
22. Li Y, Oskouian R J, Day Y J, Kern J A, Linden J, 2006. Optimization of a mouse locomotor rating system to evaluate compression-induced spinal cord injury: correlation of locomotor and morphological injury indices. Journal of Neurosurgery-Spine 4: 165-173.
23. Linden J, 2001. Molecular approach to adenosine receptors: Receptor-mediated mechanisms of tissue protection. Annual Review of Pharmacology and Toxicology 41: 775-787.
24. Linden J, 1982. Calculating the dissociation constant of an unlabeled compound from the concentration required to displace radiolabel binding by 50%. Journal of Cyclic Nucleotide Research 8: 163-172.
25. Linden J, 2005. Adenosine in tissue protection and tissue regeneration. Molecular Pharmacology 67: 1385-1387.
26. Link A A, Kino T, Worth J A, McGuire J L, Crane M L, Chrousos G P, Wilder R L, Elenkov I J, 2000. Ligand-activation of the adenosine A2a receptors inhibits IL-12 production by human monocytes. Journal of Immunology 164: 436-442.
27. Lohse M J, Maurer K, Gensheimer H P, Schwabe U, 1987. Dual Actions of Adenosine on Rat Peritoneal Mast-Cells. Naunyn-Schmiedebergs Archives of Pharmacology 335: 555-560.
28. Matute C, SanchezGomez M V, MartinezMillan L, Miledi R, 1997. Glutamate receptor-mediated toxicity in optic nerve oligodendrocytes. Proceedings of the National Academy of Sciences of the United States of America 94: 8830-8835.
29. McAdoo D J, Robak G, Xu G Y, Hughes M G, 2000. Adenosine release upon spinal cord injury. Brain Research 854: 152-157.
30. McAdoo D J, Xu G Y, Robak G, Hughes M G, 1999. Changes in amino acid concentrations over time and space around an impact injury and their diffusion through the rat spinal cord. Experimental Neurology 159: 538-544.
31. McDonald J W, Althomsons S P, Hyrc K L, Choi D W, Goldberg M P, 1998. Oligodendrocytes from forebrain are highly vulnerable to AMPA/kainate receptor-mediated excitotoxicity. Nature Medicine 4: 291-297.
32. McDonald J W, Sadowsky C, 2002. Spinal-cord injury. Lancet 359: 417-425.
33. Narayana P A, Grill R J, Chacko T, Vang R, 2004. Endogenous recovery of injured spinal cord: longitudinal in vivo magnetic resonance imaging. J. Neurosci. Res. 78: 749-759.
34. Okonkwo D O, Reece T B, Laurent J J, Hawkins A S, Ellman P I, Linden J, Kron I L, Tribble C G, Stone J R, Kern J A, 2006. A comparison of adenosine A(2A) agonism and methylprednisolone in attenuating neuronal damage and improving functional outcome after experimental traumatic spinal cord injury in rabbits. Journal of Neurosurgery-Spine 4: 64-70.
35. Okusa M D, Linden J, Macdonald T, Huang L P, 1999. Selective A(2A) adenosine receptor activation reduces ischemia-reperfusion injury in rat kidney. American Journal of Physiology-Renal Physiology 277: F404-F412.
36. Peirce S M, Skalak T C, Rieger J M, Macdonald T L, Linden J, 2001. Selective A(2A) adenosine receptor activation reduces skin pressure ulcer formation and inflammation. American Journal of Physiology-Heart and Circulatory Physiology 281: H67-H74.
37. Pitt D, Werner P, Raine C S, 2000. Glutamate excitotoxicity in a model of multiple sclerosis. Nature Medicine 6: 67-70.
38. Popovich P G, Guan Z, McGaughy V, Fisher L, Hickey W F, Basso D M, 2002. The neuropathological and behavioral consequences of intraspinal microglial/macrophage activation. Journal of Neuropathology and Experimental Neurology 61: 623-633.
39. Ramkumar V, Stiles G L, Beaven M A, Ali H, 1993. The $A_3$ adenosine receptor is the unique adenosine receptor which facilitates release of allergic mediators in mast cells. J. Biol. Chem. 268: 16887-16890.
40. Reece T B, Davis J D, Okonkwo D O, Maxey T S, Ellman P I, Li X, Linden J, Tribble C G, Kron I L, Kern J A, 2004a. Adenosine A2A analogue reduces long-term neurologic injury after blunt spinal trauma. Journal of Surgical Research 121: 130-134.
41. Reece T B, Okonkwo D O, Ellman P I, Warren P S, Smith R L, Hawkins A S, Linden J, Kron I L, Tribble C G, Kern J A, 2004b. The evolution of ischemic spinal cord injury in function, cytoarchitecture, and inflammation and the effects of adenosine A2A receptor activation. Journal of Thoracic and Cardiovascular Surgery 128: 925-932.
42. Reeves J J, Jones C A, Sheehan M J, Vardey C J, Whelan C J, 1997. Adenosine A3 receptors promote degranulation of rat mast cells both in vitro and in vivo. Inflammation Research 46: 180-184.
43. Richter M W, Fletcher P A, Liu J, Tetzlaff W, Roskams A J, 2005. Lamina propria and olfactory bulb ensheathing cells exhibit differential integration and migration and promote differential axon sprouting in the lesioned spinal cord. J. Neurosci. 25: 10700-10711.
44. Rieger J M, Brown M L, Sullivan G W, Linden J, Macdonald T L, 2001. Design, synthesis, and evaluation of novel A(2A) adenosine receptor agonists. Journal of Medicinal Chemistry 44: 531-539.
45. Rivo J, Zeira E, Galun E, Matot I, 2004. Activation of A3 adenosine receptor provides lung protection against ischemia-reperfusion injury associated with reduction in apoptosis. Am. J. Transplant. 4: 1941-1948.
46. Rokkas C K, Cronin C S, Nitta T, Helfrich L R, Lobner D C, Choi D W, Kouchoukos N T, 1995. Profound Systemic Hypothermia Inhibits the Release of Neurotransmitter Amino-Acids in Spinal-Cord Ischemia. Journal of Thoracic and Cardiovascular Surgery 110: 27-35.
47. Smith T, Groom A, Zhu B, Turski L, 2000. Autoimmune encephalomyelitis ameliorated by AMPA antagonists. Nature Medicine 6: 62-66.

48. Sullivan G W, Linden J, Buster B L, Scheld W M, 1999, Neutrophil A2A adenosine receptor inhibits inflammation in a rat model of meningitis: synergy with the type IV phosphodiesterase inhibitor, rolipram. Journal of Infectious Diseases 180: 1550-1560.

49. Tator C H, Koyanagi I, 1997. Vascular mechanisms in the pathophysiology of human spinal cord injury. Journal of Neurosurgery 86: 483-492.

50. Varani K, Gessi S, Dionisotti S, Ongini E, Borea P A, 1998. [H-3]-SCH 58261 labelling of functional A(2A) adenosine receptors in human neutrophil membranes. British Journal of Pharmacology 123: 1723-1731.

51. Walker B A M, Rocchini C, Boone R H, Ip S, Jacobson M A, 1997. Adenosine A(2a) receptor activation delays apoptosis in human neutrophils. Journal of Immunology 158: 2926-2931.

52. Yang Z Q, Day Y J, Toufektsian M C, Ramos S I, Marshall M, Wang X Q, French B A, Linden J, 2005. Infarct-sparing effect of A(2A)-adenosine receptor activation is due primarily to its action on lymphocytes. Circ. 111: 2190-2197.

53. Yu L Q, Huang Z H, Mariani J, Wang Y M, Moskowitz M, Chen J F, 2004. Selective inactivation or reconstitution of adenosine A(2A) receptors in bone marrow cells reveals their significant contribution to the development of ischemic brain injury. Nature Medicine 10: 1081-1087.

All patents, patent applications and literature cited in the specification are hereby incorporated by reference in their entirety. In the case of any inconsistencies, the present disclosure, including any definitions therein will prevail. The invention has been described with reference to various specific and preferred embodiments and techniques. However, it should be understood that many variations and modifications may be made while remaining within the invention.

Having thus described the preferred embodiments of the present invention, those of skill in the art will readily appreciate that the teachings found herein may be applied to yet other embodiments within the scope of the attached claims.

What is claimed is:

1. A therapeutic method for treating a central nervous system injury in a mammal, comprising administering to a mammal in need thereof a therapeutically effective amount of an $A_{2A}$ adenosine receptor modulator, wherein an $A_{2A}$ adenosine receptor agonist is administered first followed by administering an $A_{2A}$ adenosine receptor antagonist wherein the $A_{2A}$ adenosine receptor agonist is a substituted 6-amino-9-(tetrahydrofuran-2'-yl)purine.

2. The method of claim 1, wherein the central nervous system injury is a spinal cord injury.

3. The method of claim 1, wherein the $A_{2A}$ adenosine receptor agonist is administered before or during an injury to the central nervous system, and the antagonist is administered beginning 1-2 days after the central nervous system injury.

4. The method of claim 3, wherein the $A_{2A}$ adenosine receptor agonist is administered from about 1 to about 12 hours after the injury to the central nervous system, and the antagonist is administered beginning 1-2 days after the central nervous system injury.

5. The method of claim 1, wherein the $A_{2A}$ adenosine receptor agonist is a compound having formula (I):

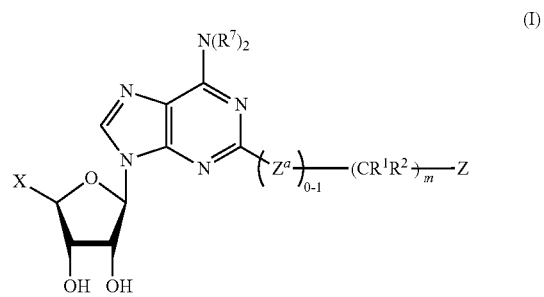

wherein
$Z^a$ is —C≡C—, —O—, —NH—, or —NHN=CR$^{3a}$—; Z is CR$^3$R$^4$R$^5$ or NR$^4$R$^5$;
each R$^1$ is independently hydrogen, halo, —OR$^a$, —SR$^a$, (C$_1$-C$_8$)alkyl, cyano, nitro, trifluoromethyl, trifluoromethoxy, (C$_3$-C$_8$)cycloalkyl, heterocycle, heterocycle(C$_1$-C$_8$)alkylene-, aryl, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$RNC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, R$^a$OC(=S)—, R$^a$C(=S)—, —SSR$^a$, R$^a$S(=O)—, R$^a$S(=O)$_2$—, or —N=NR$^b$;
each R$^2$ is independently hydrogen, halo, (C$_1$-C$_8$)alkyl, (C$_3$-C$_8$)cycloalkyl, heterocycle, heterocycle(C$_1$-C$_8$)alkylene-, aryl, aryl(C$_1$-C$_8$)alkylene-, heteroaryl, or heteroaryl(C$_1$-C$_8$)alkylene-; or R$^1$ and R$^2$ and the atom to which they are attached is C=O, C=S or C=NR$^d$;
R$^4$ and R$^5$ are independently H or (C$_1$-C$_8$)alkyl; or R$^4$ and R$^5$ together with the atom to which they are attached form a saturated, partially unsaturated, or aromatic ring that is mono-, bi- or polycyclic and has 3, 4, 5, 6, 7, 8, 9, or 10 ring atoms optionally having 1, 2, 3, or 4 heteroatoms; wherein the heteroatoms are non-peroxide oxy (—O—), S(O)$_{0-2}$, or amine in the ring;
wherein R$^4$ and R$^5$ are independently substituted with 0-3 R$^6$ or any ring comprising R$^4$ and R$^5$ is substituted with from 0 to 14 R$^6$ groups; wherein each R$^6$ is independently halo, —OR$^a$, —SR$^a$, (C$_1$-C$_8$)alkyl, cyano, nitro, trifluoromethyl, trifluoromethoxy, (C$_1$-C$_8$)cycloalkyl, (C$_6$-C$_{12}$)bicycloalkyl, heterocycle, heterocycle (C$_1$-C$_8$)alkylene-, aryl, aryl (C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, R$^a$OC(=S)—, R$^a$C(=S)—, —SSR$^a$, R$^a$S(=O)—, —NNR$^b$, or two R$^6$ groups and the atom to which they are attached is C=O or C=S; or two R$^6$ groups together with the atom or atoms to which they are attached can form a carbocyclic or heterocyclic ring comprising from 1 to 6 carbon atoms and 1, 2, 3, or 4 heteroatoms; wherein the heteroatoms are non-peroxide oxy (—O—), thio (—S—), sulfinyl (—SO—), sulfonyl (—S(O)$_2$—) or amine (—NR$^b$—) in the ring;
R$^3$ is hydrogen, halo, —OR$^a$, —SR$^a$, (C$_1$-C$_8$)alkyl, cyano, nitro, trifluoromethyl, trifluoromethoxy, (C$_3$-C$_8$)cycloalkyl, heterocycle, heterocycle(C$_1$-C$_8$)alkylene-, aryl, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, R$^a$OC (=S)—, R$^a$C(=S)—, —SSR$^a$, R$^a$S(=O)—, R$^a$S(=O)$_2$—, —NNR$^b$; or if the ring formed from CR$^3$R$^4$R$^5$ is aryl or heteroaryl or partially unsaturated then R$^3$ can be absent;

R$^{3a}$ is hydrogen, (C$_1$-C$_8$)alkyl, or aryl;

each R$^7$ is independently hydrogen, (C$_1$-C$_8$)alkyl, (C$_3$-C$_8$)cycloalkyl, aryl, aryl(C$_1$-C$_8$)alkylene, heteroaryl, or heteroaryl(C$_1$-C$_8$)alkylene-;

X is —CH$_2$OR$^a$, —CO$_2$R$^a$, —CH$_2$OC(O)R$^a$, —C(O)NR$^b$R$^c$, —CH$_2$SR$^a$, —C(S)OR$^a$, —CH$_2$OC(S)R$^a$, —C(S)NR$^b$R$^c$, or —CH$_2$N(R$^b$)(R$^c$); or

X is aromatic ring of the formula:

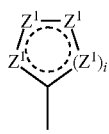

each Z$^1$ is non-peroxide oxy (—O—), S(O)$_{0-2}$, —C(R$^8$)—, or amine (—NR$^8$—), provided that at least one Z$^1$ is non-peroxide oxy (—O—), thio (—S—), sulfinyl (—SO—), sulfonyl (—S(O)$_2$—) or amine (—NR$^8$—);

each R$^8$ is independently hydrogen, (C$_1$-C$_8$)alkyl, (C$_1$-C$_8$)alkenyl, (C$_3$-C$_8$)cycloalkyl, (C$_3$-C$_8$)cycloalkyl(C$_1$-C$_8$)alkylene, (C$_3$-C$_8$)cycloalkenyl, (C$_3$-C$_8$)cycloalkenyl(C$_1$-C$_8$)alkylene, aryl, aryl(C$_1$-C$_8$)alkylene, heteroaryl, or heteroaryl(C$_1$-C$_8$)alkylene, wherein any of the alkyl or alkenyl groups of R$^8$ are optionally interrupted by —O—, —S—, or —N(R$^a$)—;

wherein any of the alkyl, cycloalkyl, heterocycle, aryl, or heteroaryl, groups of R$^1$, R$^2$, R$^3$, R$^{3a}$, R$^6$, R$^7$, and R$^8$ is optionally substituted on carbon with one or more substituents, where the substituents are halo, —OR$^a$, —SR$^a$, (C$_1$-C$_8$)alkyl, cyano, nitro, trifluoromethyl, trifluoromethoxy, (C$_3$-C$_8$)cycloalkyl, (C$_6$-C$_{12}$)bicycloalkyl, heterocycle, heterocycle(C$_1$-C$_8$)alkylene-, aryl, aryloxy, aryl (C$_1$-C$_8$)alkylene-, heteroaryl, heteroaryl-(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, R$^a$OC(=S)—, R$^a$C(=S)—, —SSR$^a$, R$^a$S(=O)$_p$—, R$^b$R$^c$NS(O)$_p$—, or —N=NR$^b$;

wherein any (C$_1$-C$_8$)alkyl, (C$_3$-C$_8$)cycloalkyl, (C$_6$-C$_{12}$)bicycloalkyl, (C$_1$-C$_8$)alkoxy, (C$_1$-C$_8$)alkanoyl, (C$_1$-C$_8$)alkylene, or heterocycle, is optionally partially unsaturated;

each R$^a$, R$^b$, and R$^c$ is independently hydrogen, (C$_1$-C$_{12}$)alkyl, (C$_1$-C$_8$)alkoxy-(C$_1$-C$_8$)alkyl-, (C$_3$-C$_8$)cycloalkyl, (C$_1$-C$_8$)alkylthio-(C$_1$-C$_8$)alkyl-, amino acid, aryl, aryl (C$_1$-C$_8$)alkylene, heteroaryl, or heteroaryl(C$_1$-C$_8$)alkylene; or R$^b$ and R$^c$, together with the nitrogen to which they are attached, form a pyrrolidino, piperidino, morpholino, or thiomorpholino ring;

R$^d$ is hydrogen or (C$_1$-C$_6$)alkyl; i is 1 or 2; m is 0 to 8; and p is 0 to 2; or a pharmaceutically acceptable salt thereof.

6. The method of claim 5, wherein the compound has formula (Ia):

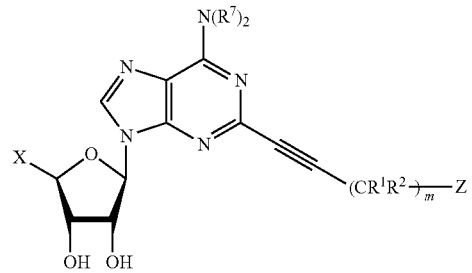

wherein R$^1$ is hydrogen, —OH, —CH$_2$OH, —OMe, —OAc, —NH$_2$, —NHMe, —NMe$_2$ or —NHAc;

R$^2$ is hydrogen, (C$_1$-C$_8$)alkyl, cyclopropyl, cyclohexyl or benzyl;

Z is CR$^3$R$^4$R$^5$ or NR$^4$R$^5$;

R$^3$ is hydrogen, OH, OMe, OAc, NH$_2$, NHMe, NMe$_2$ or NHAc;

CR$^3$R$^4$R$^5$ or NR$^4$R$^5$ is cyclopentane, cyclohexane, piperidine, dihydro-pyridine, tetrahydro-pyridine, pyridine, piperazine, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, or pyrazolidine; and is optionally substituted with 0-2 R$^6$ groups;

the ring CR$^3$R$^4$R$^5$ or NR$^4$R$^5$ is:

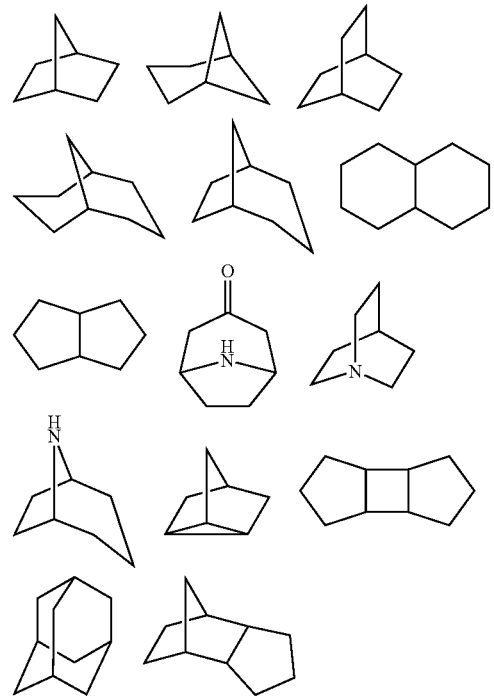

and is optionally substituted with 0-2 R$^6$ groups;

R$^6$ is (C$_1$-C$_8$)alkyl, —OR$^a$, —CO$_2$R$^a$, R$^a$C(=O)—, R$^a$C(=O)O—, R$^b$R$^c$N—, R$^b$R$^c$NC(=O)—, or aryl;

R$^7$ is hydrogen, (C$_1$-C$_8$)alkyl, aryl, aryl(C$_1$-C$_8$)alkylene, or heteroaryl(C$_1$-C$_8$)alkylene;

R$^8$ is methyl, ethyl, propyl, 2-propenyl, cyclopropyl, cyclobutyl, cyclopropylmethyl, —(CH$_2$)$_2$CO$_2$CH$_3$, or —(CH$_2$)$_{2-3}$OH;

$R^a$ and $R^b$ are independently hydrogen, $(C_3-C_4)$-cycloalkyl, $(C_1-C_8)$alkyl, aryl or aryl$(C_1-C_8)$alkylene;

X is —CH$_2$OR$^a$, —CO$_2$R$^a$, —CH$_2$OC(O)R$^a$, or C(O)NR$^b$R$^c$;

or X is:

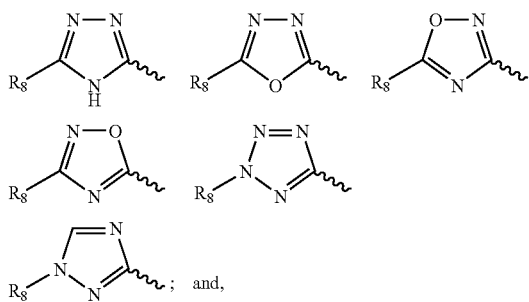

m is 0, 1, or 2; or a pharmaceutically acceptable salt thereof.

7. The method of claim 5, wherein:

$R^1$ is hydrogen, OH, OMe, or NH$_2$;

$R^2$ is hydrogen, methyl, ethyl or propyl;

the ring CR$^3$R$^4$R$^5$ or NR$^4$R$^5$ is:

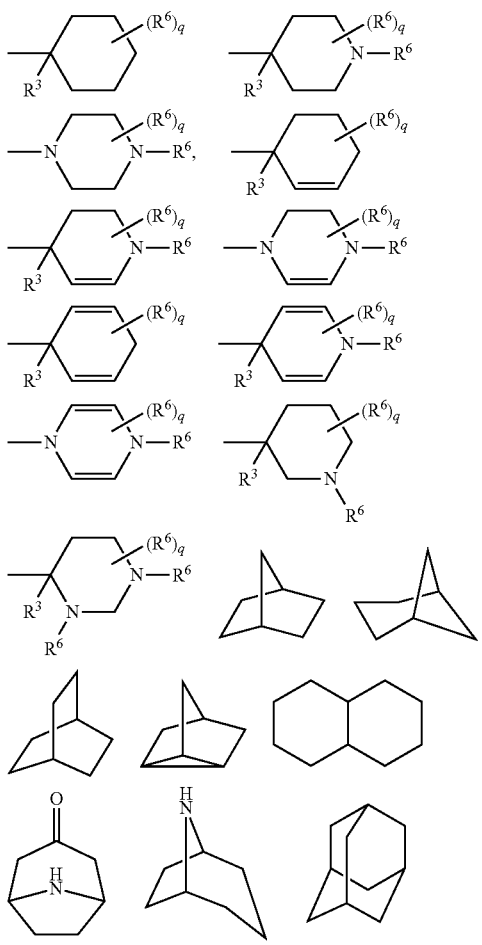

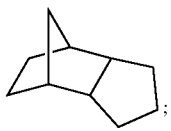

$R^3$ is hydrogen, OH, OMe, or NH$_2$;

q is from 0 to 2;

$R^6$ is $(C_1-C_8)$alkyl, —OR$^a$, —CO$_2$R$^a$, R$^a$C(=O)—, R$^a$C(=O)O—, R$^b$R$^c$N—, R$^b$R$^c$NC(=O)—, or aryl;

$R^a$ and $R^b$ are independently hydrogen, methyl, ethyl, propyl, butyl, ethylhexyl, cyclopropyl, cyclobutyl, phenyl or benzyl;

N(R$^7$)$_2$ is amino, methylamino, dimethylamino; ethylamino; pentylamino, diphenylethylamino, (pyridinylmethyl)amino, (pyridinyl)(methyl)amino, diethylamino or benzylamino; and, $R^8$ is methyl, ethyl, propyl, or cyclopropyl;

X is —CH$_2$OR$^a$ or —C(O)NR$^b$R$^c$;

or X is:

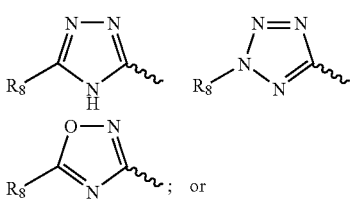

a pharmaceutically acceptable salt thereof.

8. The method of claim 5, wherein $R^1$ is hydrogen, OH, or NH$_2$;

$R^2$ is hydrogen or methyl;

the ring CR$^3$R$^4$R$^5$ or NR$^4$R$^5$ is:

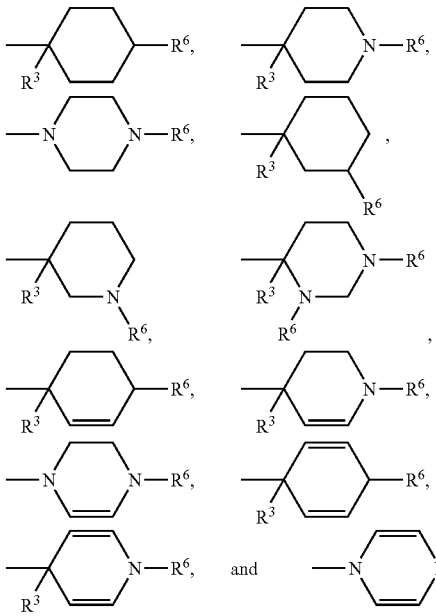

-continued

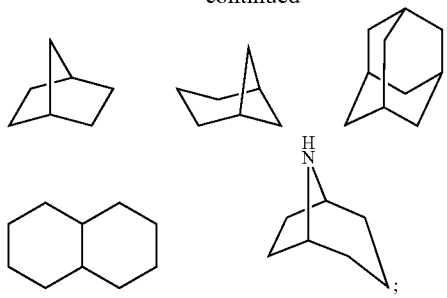

R³ is hydrogen, OH, or NH₂;
R⁶ is methyl, ethyl, t-butyl, phenyl, —CO₂Rᵃ—CONRᵇRᶜ, or RᵃC(=O)—; Rᵇ is H; Rᵃ is methyl, ethyl, propyl, butyl, pentyl, ethylhexyl cyclopropyl, or cyclobutyl; —N(R⁷)₂ is amino, methylamino, dimethylamino; ethylamino; diethylamino or benzylamino; or
a pharmaceutically acceptable salt thereof.

9. The method of claim 5, wherein:
R¹ is hydrogen or OH;
R² is hydrogen;
the ring CR³R⁴R⁵ or NR⁴R⁵ is:

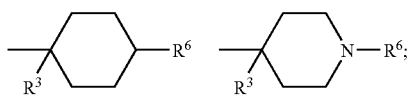

R³ is hydrogen or OH;
R⁶ is methyl, ethyl, —CO₂Rᵃ, or —CONRᵇRᶜ;
Rᵇ is H; Rᵃ is methyl, ethyl, iso-propyl, iso-butyl, tert-butyl, or cyclopropyl; N(R⁷)₂ is amino, or methylamino;
X is —CH₂OH,

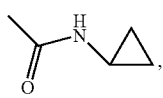

C(O)NHCH₃, or —C(O)NHCH₂CH₃;
or a pharmaceutically acceptable salt thereof.

10. The method of claim 5, wherein the ring comprising R⁴ and R⁵ is 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-carboxylic acid tert-butyl ester, tert-butylester, 1-piperidine-4-carboxylic acid methyl ester, or 1-piperidine-4-carboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, or 1-piperidine-3-carboxylic acid tert-butyl ester;
or a pharmaceutically acceptable salt thereof.

11. The method of claim 5, wherein the A$_{2A}$ adenosine receptor agonist is:

| Compound # | Rᶜ | R⁷ | —(CHR¹)$_m$—Z |
|---|---|---|---|
| 1 | Et | H | cyclohexyl-C(O)OMe |
| 2 | cPr | H | piperidinyl-C(O)OMe |
| 3 | Et | H | piperidinyl-C(O)OMe |
| 4 | Et | H | piperidinyl-C(O)OEt |
| 5 | Et | H | piperidinyl-C(O)O-iBu |
| 6 | Et | H | piperazinyl-C(O)OEt |

61
-continued
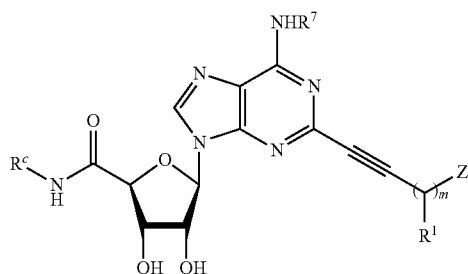
| Compound # | R$^c$ | R$^7$ | —(CHR$^1$)$_m$—Z |
|---|---|---|---|
| 7 | Et | H | 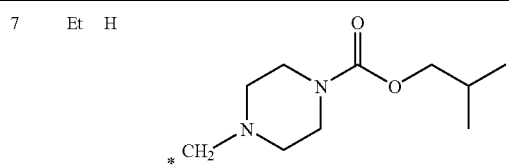 |
| 8 | Et | H | 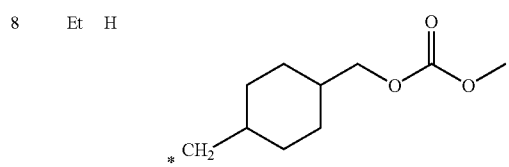 |
| 9 | Et | H | 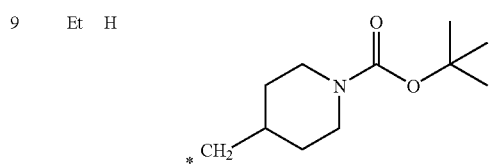 |
| 10 | Et | H | 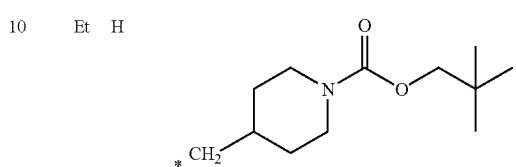 |
| 11 | cPr | H | 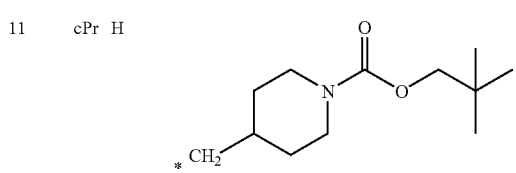 |
| 12 | Et | H | 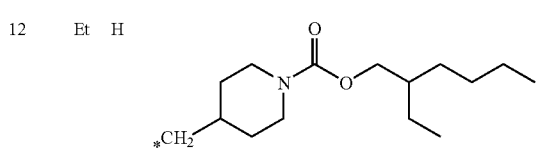 |
| 13 | cPr | H | 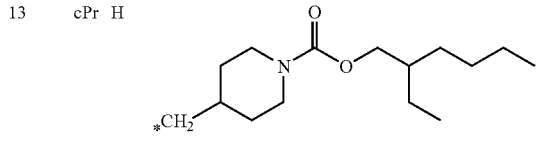 |
62
-continued
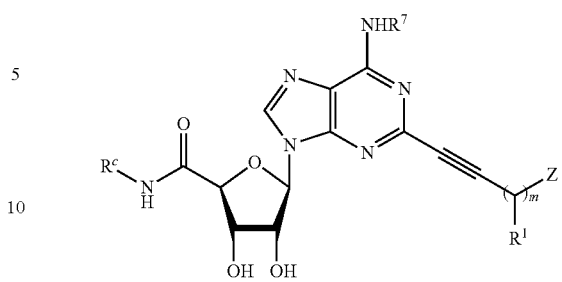
| Compound # | R$^c$ | R$^7$ | —(CHR$^1$)$_m$—Z |
|---|---|---|---|
| 14 | Et | H | 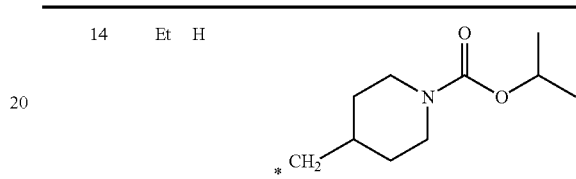 |
| 15 | cPr | H | 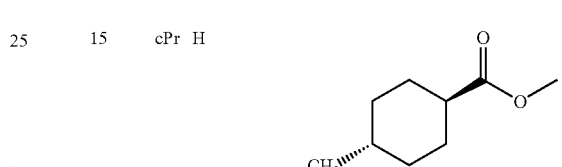 |
| 16 | Et | H | 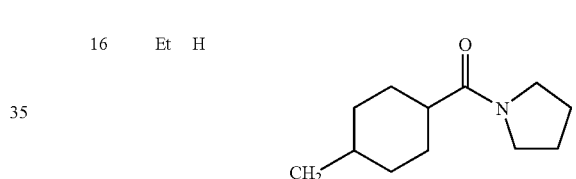 |
| 17 | Et | H | 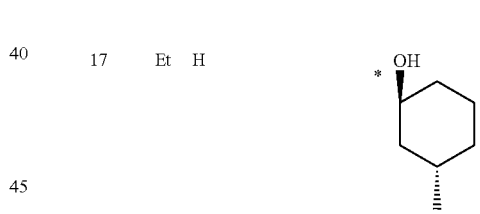 |
| 18 | Et | H | 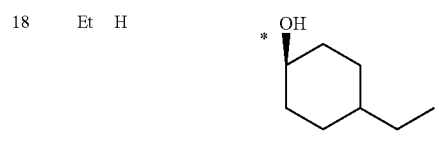 |
| 19 | Et | H |  |
| 20 | Et | H |  |

-continued
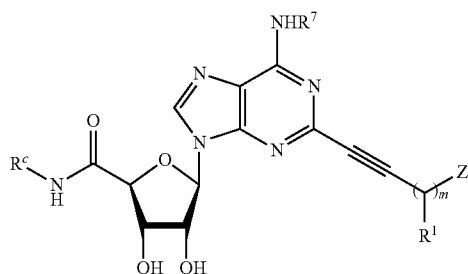
| Compound # | $R^c$ | $R^7$ | —(CHR$^1$)$_m$—Z |
|---|---|---|---|
| 21 | Et | H | 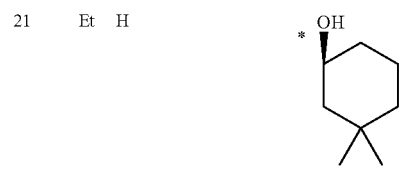 |
| 22 | cPr | H |  |
| 23 | Et | H | 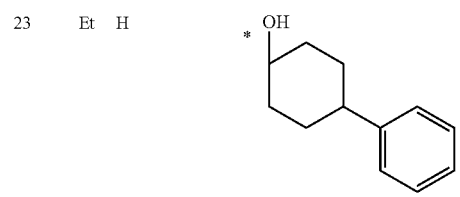 |
| 24 | Et | H | 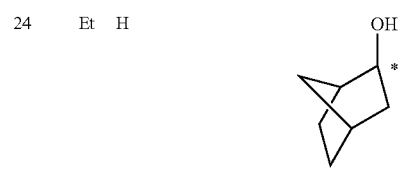 |
| 25 | cPr | H | 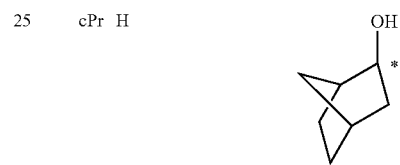 |
| 26 | cPr | H | 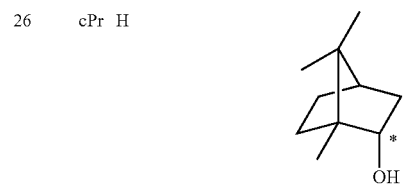 |
| 27 | Et | H |  |
-continued
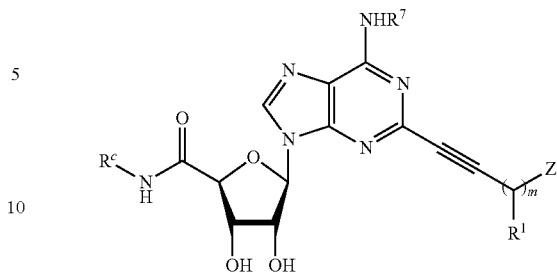
| Compound # | $R^c$ | $R^7$ | —(CHR$^1$)$_m$—Z |
|---|---|---|---|
| 28 | cPr | H |  |
| 29 | Et | H | 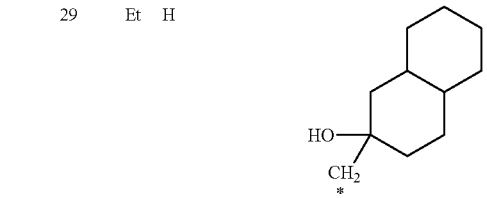 |
| 30 | cPr | H | 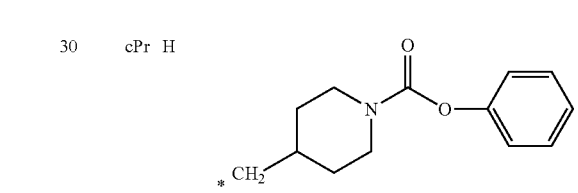 |
| 31 | Et | H | 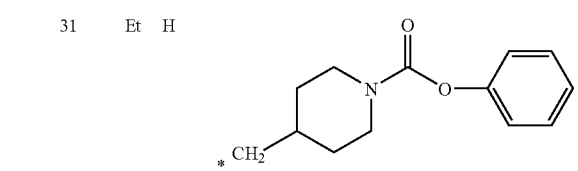 |
| 32 | cPr | H | 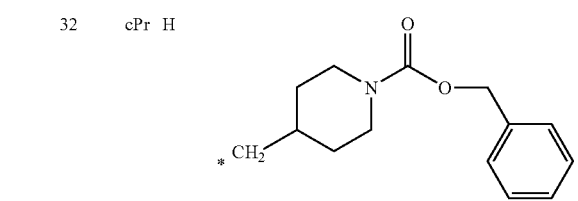 |
| 33 | Et | H | 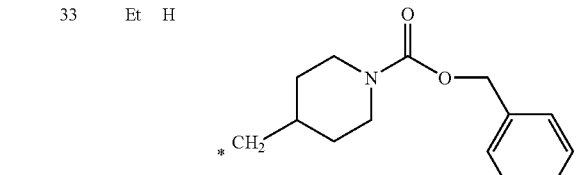 |
where * indicates the point of attachment; or
a pharmaceutically acceptable salt thereof.
12. The method of claim 11, wherein the A$_{2A}$ adenosine receptor agonist has the formula:

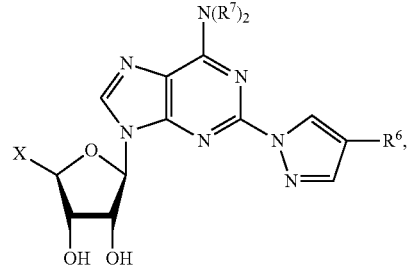
(Ib)
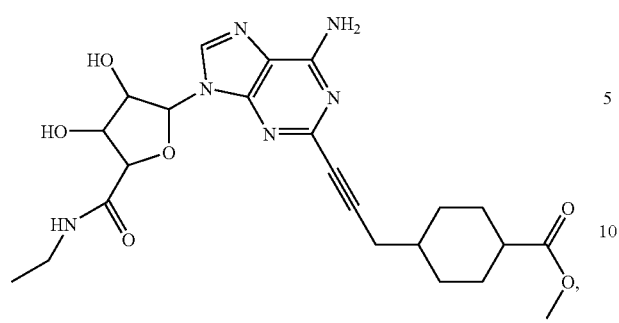
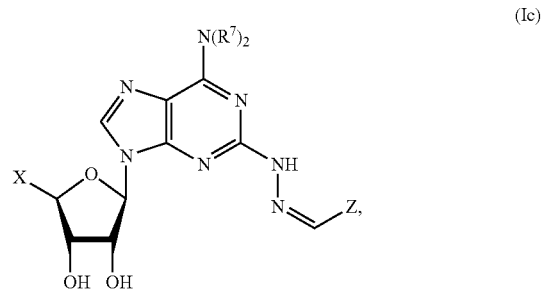
(Ic)
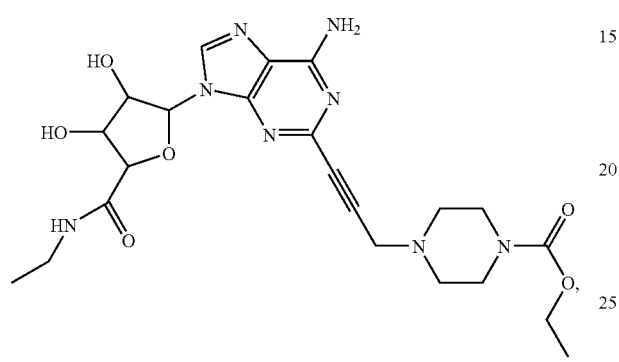
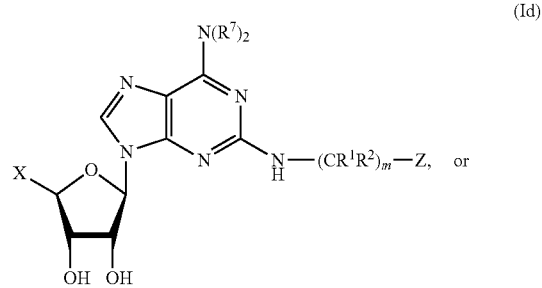
(Id)
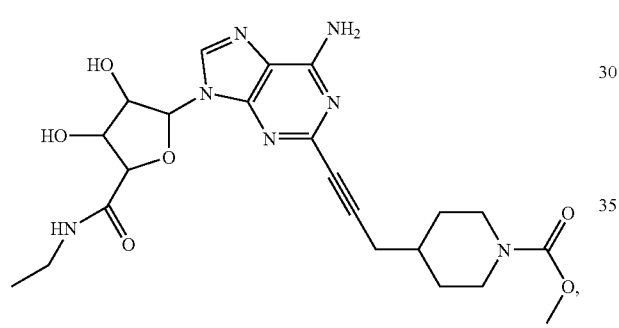
a pharmaceutically acceptable salt thereof.
14. The method of claim 13, wherein the $A_{2A}$ adenosine receptor agonist is:
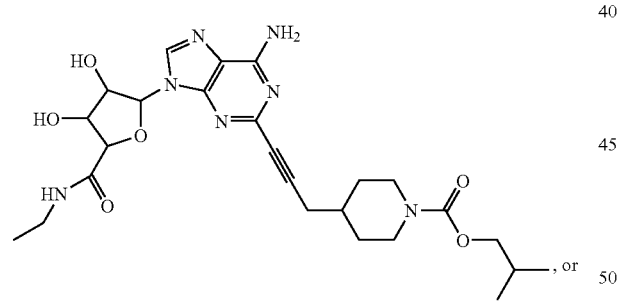
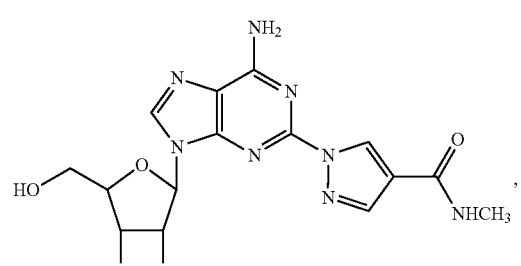
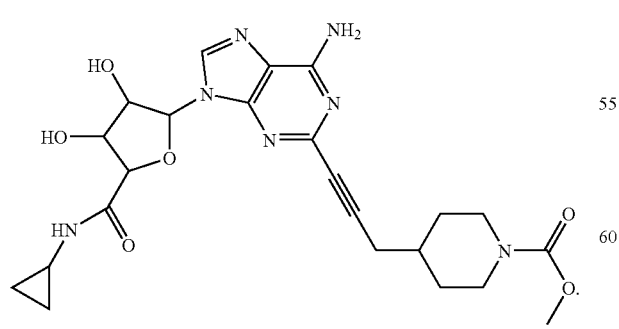
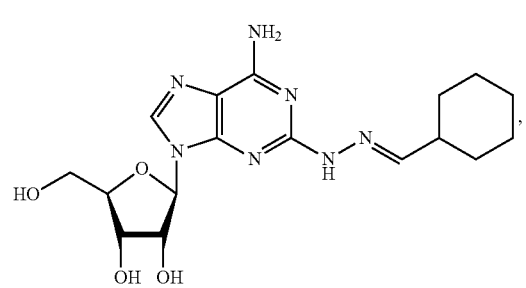
13. The method of claim 5, wherein the $A_{2A}$ adenosine agonist is:

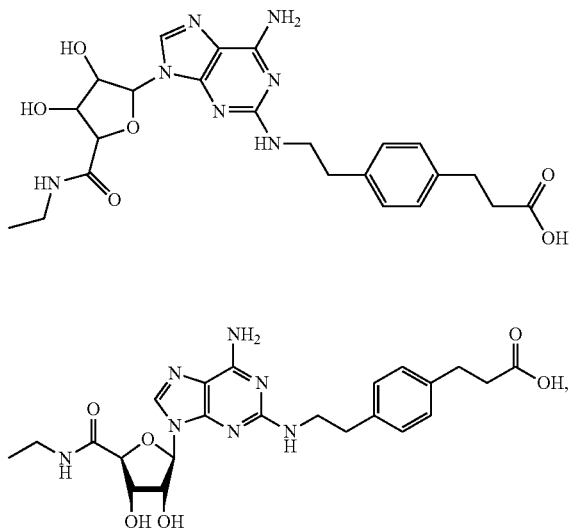

or a pharmaceutically acceptable salt thereof.

15. The method of claim 5, wherein the $A_{2A}$ adenosine receptor agonist has the formula:

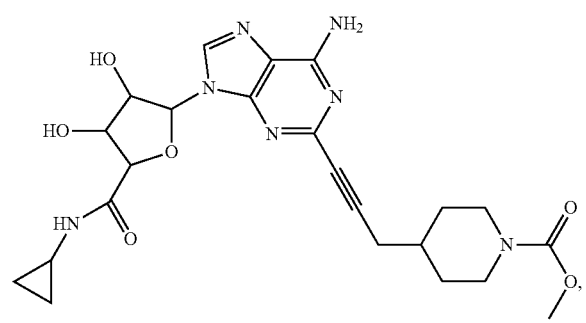

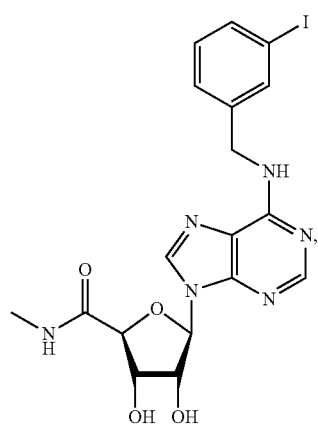

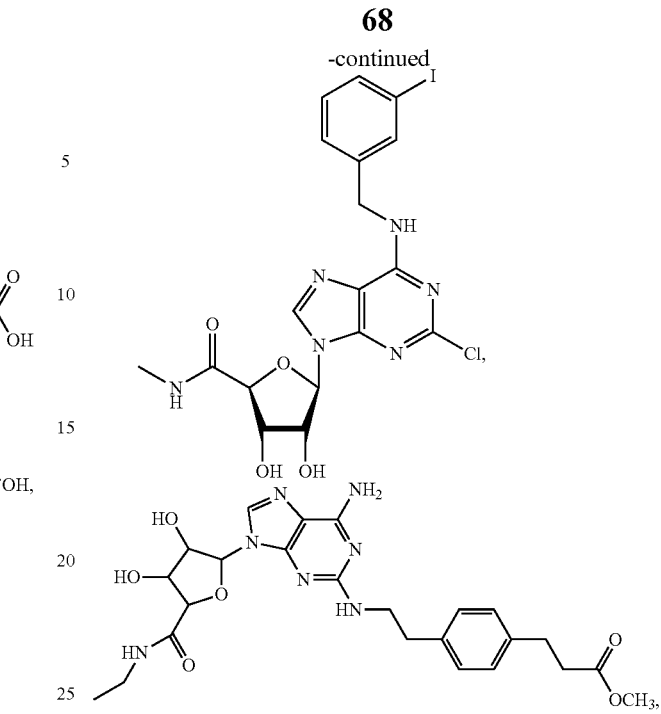

or a pharmaceutically acceptable salt thereof.

16. The method of claim 1, wherein the $A_{2A}$ adenosine receptor antagonist is a 2,7-disubstituted-5-amino-pyrazolo[4,3-e]-[1,2,4]-triazolo[1,5-c]pyrimidine, 2,7-disubstituted-5-amino-[1,2,4]triazolo[1,5-c]pyrimidine, 2,5-disubstituted-7-amino-[1,2,4]triazolo[1,5-a][1,3,5]triazine, 9-substituted-2-(substituted-ethyn-1-yl)-adenine, 7-methyl-8-styrylxanthine derivative, pyrazolo[4,3-e) 1,2,4-triazolo[1,5-c]pyrimidine, 5-amino-imidazolo-[4,3-e]-1,2,4-triazolo[1,5-c]pyrimidine or mixture thereof.

17. The method of claim 16, wherein the $A_{2A}$ adenosine receptor antagonist is ZM241385, KW6002, VR2006, SCH58261, (−)—R,S)-mefloquine, 3,7-Dimethyl-1-propargylxanthine (DMPX), 3-(3-hydroxypropyl)-7-methyl-8-(m-methoxystyryl)-1-propargylxanthine (MX2), 3-(3-hydroxypropyl)-8-(3-methoxystyryl)-7-methyl-1-propargylxanthine phosphate disodium salt (MSX-3), KW-6002, 8-chlorostyrylcaffeine, KF17837, VER-1 1135, VER-6409, VER 6440, VER 6489, VER 6623, VER 6947, VER 7130, VER 7146, VER 7448, VER 7835, VER 8177, a pharmaceutically acceptable salt or mixture thereof.

18. The method of claim 5, wherein the $A_{2A}$ adenosine receptor agonist is a selective $A_{2A}$ adenosine receptor agonist.

19. The method of claim 5, wherein the $A_{2A}$ adenosine receptor antagonist is a selective $A_{2A}$ adenosine receptor antagonist.

20. The method of claim 1, wherein the $A_{2A}$ adenosine receptor modulator is administered using topical, oral, buccal, intravenous, intramuscular, intra arterial, intramedullary, intraventricular, transdermal, subcutaneous, intraperitoneal, intranasal, enteral, topical, sublingual, vaginal, pulmonary, or rectal means.

21. The method of claim 1, wherein the $A_{2A}$ adenosine receptor modulator is administered using ophthalmic means.

* * * * *